United States Patent
Ma et al.

(10) Patent No.: US 10,710,979 B2
(45) Date of Patent: Jul. 14, 2020

(54) EGFR KINASE INHIBITOR AND PREPARATION METHOD AND USE THEREOF

(71) Applicant: ZHEJIANG BOSSAN PHARMACEUTICAL CO. LTD., Hangzhou, Zhejiang (CN)

(72) Inventors: Dawei Ma, Zhejiang (CN); Qiang Yu, Zhejiang (CN); Junying Yuan, Zhejiang (CN); Hongguang Xia, Zhejiang (CN); Dongpo Cai, Zhejiang (CN); Kailiang Wang, Zhejiang (CN); Chen Zhang, Zhejiang (CN); Shanghua Xia, Zhejiang (CN)

(73) Assignee: ZHEJIANG BOSSAN PHARMACEUTICAL CO. LTD., Hangzhou, Zhejiang (CN)

( * ) Notice: Subject to any disclaimer, the term of this patent is extended or adjusted under 35 U.S.C. 154(b) by 10 days.

(21) Appl. No.: 15/763,156

(22) PCT Filed: Jul. 11, 2016

(86) PCT No.: PCT/CN2016/089679
§ 371 (c)(1),
(2) Date: Aug. 8, 2018

(87) PCT Pub. No.: WO2017/049992
PCT Pub. Date: Mar. 30, 2017

(65) Prior Publication Data
US 2018/0346444 A1  Dec. 6, 2018

(30) Foreign Application Priority Data
Sep. 25, 2015  (CN) .................... 2015 1 0622837

(51) Int. Cl.
| | | |
|---|---|---|
| *C07D 401/12* | (2006.01) | |
| *C07D 401/14* | (2006.01) | |
| *C07D 405/14* | (2006.01) | |
| *A61K 31/506* | (2006.01) | |
| *A61P 35/00* | (2006.01) | |
| *C07D 239/48* | (2006.01) | |

(52) U.S. Cl.
CPC .......... *C07D 401/14* (2013.01); *A61K 31/506* (2013.01); *C07D 239/48* (2013.01); *C07D 401/12* (2013.01); *C07D 405/14* (2013.01); *A61P 35/00* (2018.01)

(58) Field of Classification Search
CPC .. C07D 401/04; C07D 403/04; A61K 31/506; A61P 35/00
USPC .................. 544/296, 324; 514/275
See application file for complete search history.

(56) References Cited

U.S. PATENT DOCUMENTS

| | | | | |
|---|---|---|---|---|
| 8,338,439 | B2 * | 12/2012 | Singh .................. | C07D 239/47 514/275 |
| 8,975,249 | B2 * | 3/2015 | Lee ...................... | C07D 403/14 514/211.15 |
| 2012/0149687 | A1 * | 6/2012 | Lee ...................... | C07D 403/14 514/211.15 |
| 2012/0157426 | A1 | 6/2012 | Lee et al. | |

FOREIGN PATENT DOCUMENTS

| | | |
|---|---|---|
| CN | 103269704 A | 8/2013 |
| CN | 104860890 A | 8/2015 |
| CN | 105461640 A | 4/2016 |
| KR | 20130133202 A | 12/2013 |

OTHER PUBLICATIONS

International Search Report and Written Opinion (English and Chinese) issued in PCT/CN2016/089679, dated Oct. 13, 2016, 16 pages provided.

* cited by examiner

*Primary Examiner* — Venkataraman Balasubramanian
(74) *Attorney, Agent, or Firm* — Jun He Law Offices P.C.; James J. Zhu

(57) ABSTRACT

The present invention provides an EGFR kinase inhibitor and a preparation method and use thereof. Specifically, the present invention provides a compound as shown in formula (I), the definition of each group therein being as described in the description. Said compound is an efficient EGFR inhibitor.

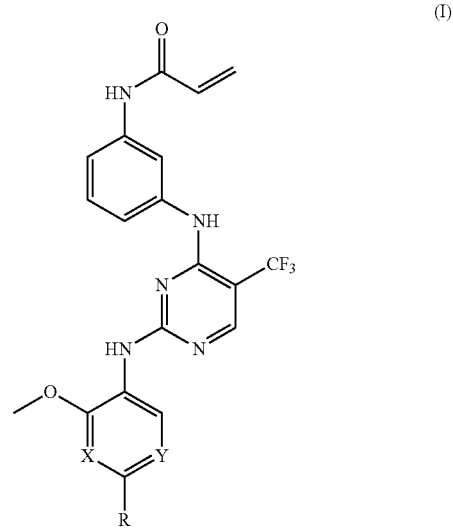

9 Claims, 3 Drawing Sheets

EGFR KINASE INHIBITOR AND PREPARATION METHOD AND USE THEREOF

FIELD OF THE INVENTION

The present invention relates to the field of medicinal chemistry. In particular, the present invention provides an EGFR kinase inhibitor, and a preparation method and application thereof.

BACKGROUND OF THE INVENTION

EGFR (epidermal growth factor receptor, referred to as EGFR, HER1 or ErbB-1) is a member of the epidermal growth factor receptor (HER) family, which play an important role in cell physiology. EGFR is a tyrosine kinase receptor, whose signal pathway plays an important regulatory role in cell proliferation, growth, differentiation, etc., and of which the abnormal expression or mutation usually leads to tumor.

Small molecule tyrosine kinase inhibitors prevent the interaction of ATP and receptor kinases, block the induction of intracellular kinase autophosphorylation led by ligand-receptor binding, and block the cross-phosphorylation triggered by dimerization of EGFR receptors, thereby block downstream signaling pathways, and is highly efficient and specific by the competitive binding of tyrosine kinase phosphorylation sites in the intracellular domain of EGFR.

The use of first-generation reversibly binding tyrosine kinase inhibitors, such as Gefitinib and Erlotinib, are susceptible to acquired resistance. Michael J. Eck et al. has found that this resistance is mainly due to the T790M mutation occurred in the gatekeeper residue of ErbB1, and this mutation produces resistance by enhancing the affinity of ATP and EGFR tyrosine kinases.

In 2009, Wenjun Zhou et al. discovered novel mutant selective small molecule inhibitors, such as WZ4002 and WZ8040:

Emily J. Hanan et al. obtained new kinase inhibitors through the cyclization strategy:

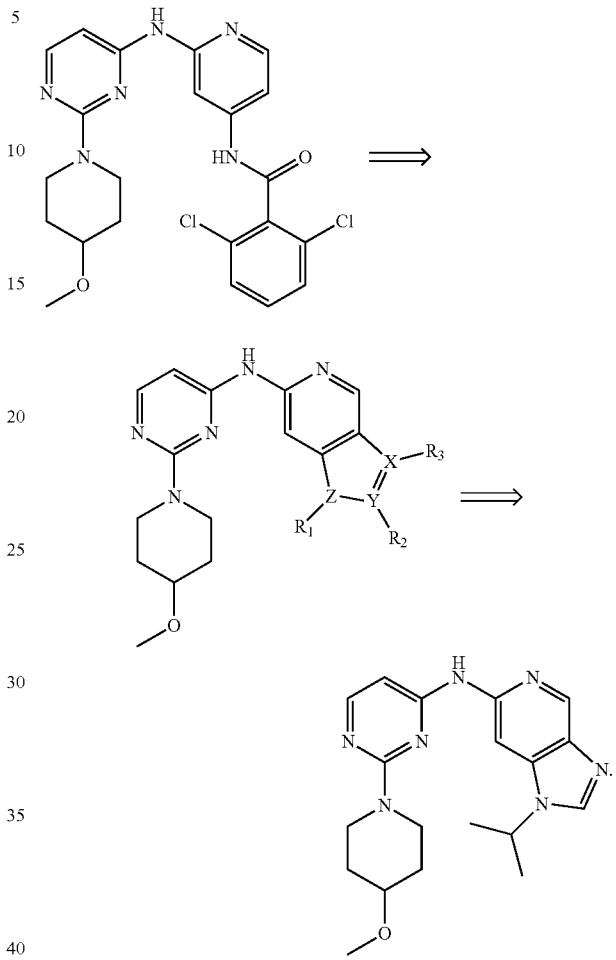

Kwangho Lee et al. also developed a series of EGFR kinase inhibitors (US2012157426) based on this and found that I-1 has very good inhibitory activity:

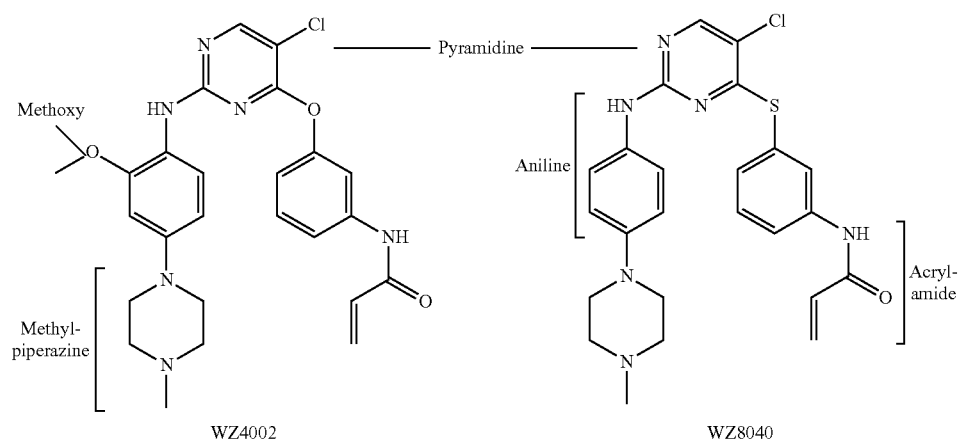

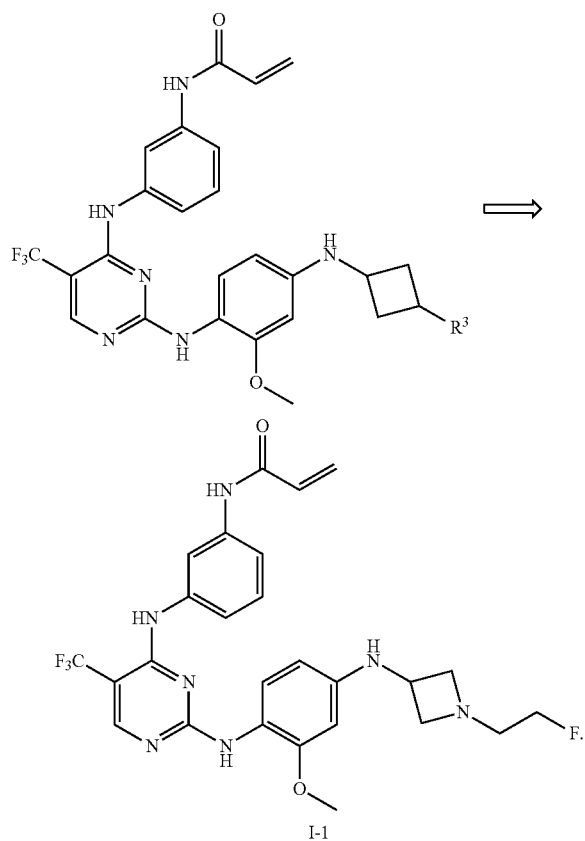

They further designed compound I-4 (KR20130133202, CN103269704):

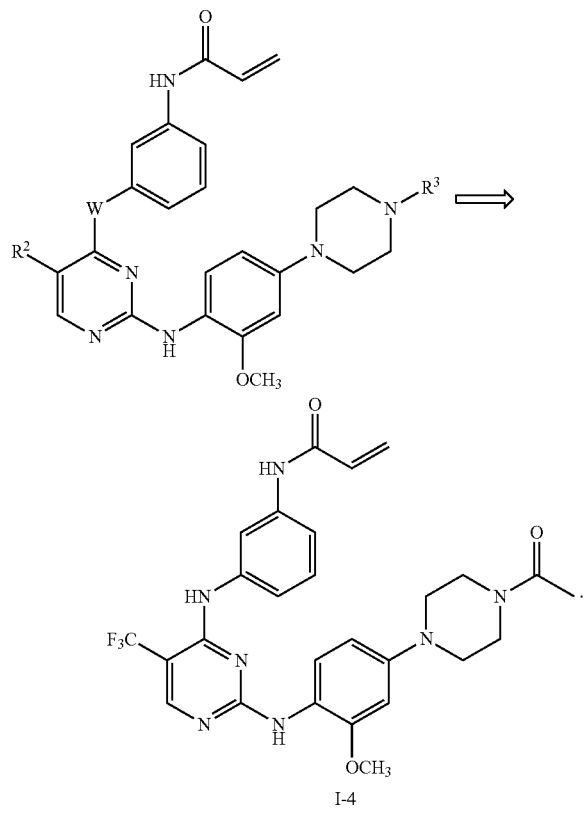

Since EGFR inhibitors have important applications in the treatment of tumors, there is an urgent need in the art to develop drugs having tyrosine kinase inhibitory activity.

SUMMARY OF THE INVENTION

The object of the present invention is to provide a novel tyrosine kinase inhibitory compound. The compound has a higher inhibitory activity than the conventional tyrosine kinase inhibitory compound.

In a first aspect of the present invention, there is provided a compound of formula (I) as follows:

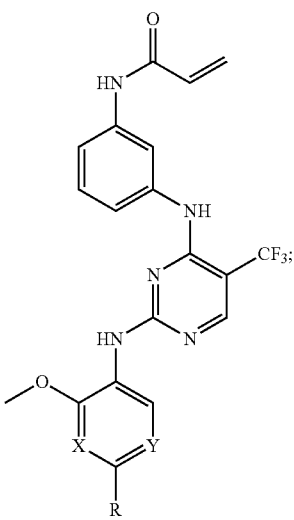

wherein:

X, Y are each independently selected from the group consisting of N, CH; with the proviso that X and Y are not CH at the same time;

R is selected from the group consisting of: unsubstituted 5-7 membered heterocycles or 5-7 membered heterocycles substituted by 1-5 substituents, C1-C6 alkyl-(unsubstituted 5-7 membered heterocycles or 5-7 membered heterocycles substituted by 1-5 substituents), —NH-(unsubstituted 5-7 membered heterocycles or 5-7 membered heterocycles substituted by 1-5 substituents), —N(CH$_3$)-(unsubstituted 5-7 membered heterocycles or 5-7 membered heterocycles substituted by 1-5 substituents), wherein the heterocycle contains at least one heteroatom selected from the group consisting of N, O and S; the substitution means one or more hydrogen atoms on the group are replaced by R$_1$ substituents;

wherein the R$_1$ is selected from the group consisting of: unsubstituted or halogenated C1-C6 alkyl, C3-C8 cycloalkyl, unsubstituted or halogenated C1-C6 alkoxy, C3-C8 cycloalkyloxy, —C(O)—R$_2$, C2-C8 alkylacyl, C2-C8 alkoxyacyl, —S(O)$_2$—R$_2$, —SOR$_2$;

the R$_2$ is selected from the group consisting of unsubstituted or halogenated C1-C6 alkyl, unsubstituted or halogenated C1-C6 alkoxy, C3-C8 cycloalkyl, C3-C8 cycloalkoxy, —CH$_2$—OAc, —NH$_2$, —NH(C1-C6 alkyl), —N(C1-C6 alkyl)$_2$.

In another preferred example, the X is N, and Y is CH.

In another preferred example, R is selected from the group consisting of:

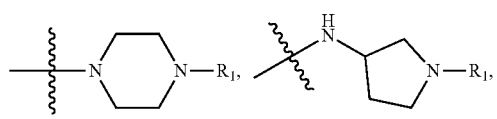

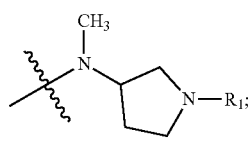

wherein the $R_1$ is selected from the group consisting of: unsubstituted or halogenated C1-C6 alkyl, C3-C8 cycloalkyl, unsubstituted or halogenated C1-C6 alkoxy, C3-C8 cycloalkyloxy, —C(O)—$R_2$, -Boc, —S(O)$_2$—$R_2$, —CH$_2$—OAc;

the $R_2$ is selected from the group consisting of unsubstituted or halogenated C1-C6 alkyl, unsubstituted or halogenated C1-C6 alkoxy, C3-C8 cycloalkyl, C3-C8 cycloalkoxy, —CH$_2$—OAc, —NH$_2$, —NH(C1-C6 alkyl), —N(C1-C6 alkyl)$_2$.

In another preferred embodiment, said compound of formula (I) is selected from the group consisting of:

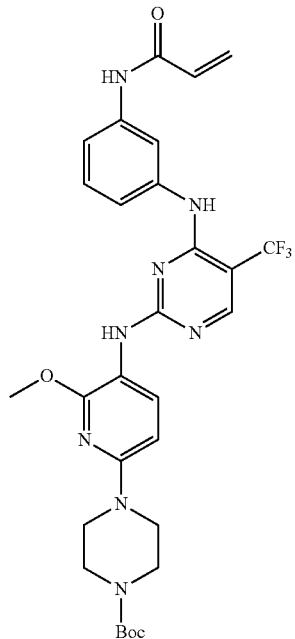

ES-070

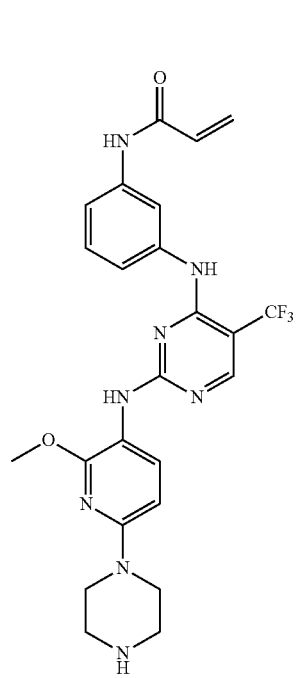

ES-069

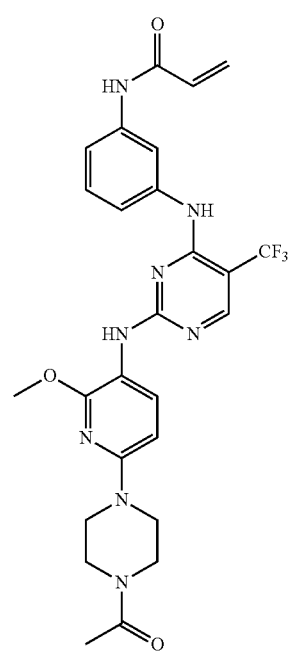

ES-071

ES-072
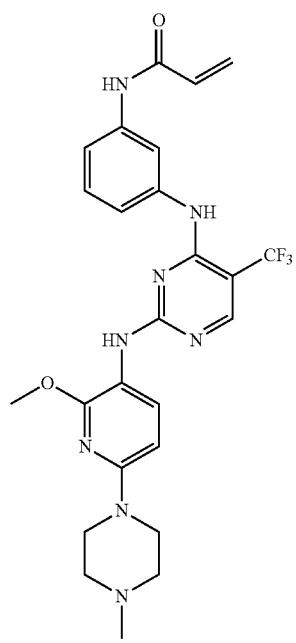
ES-073
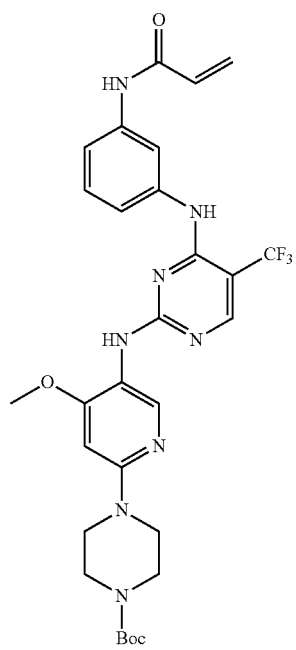
ES-074
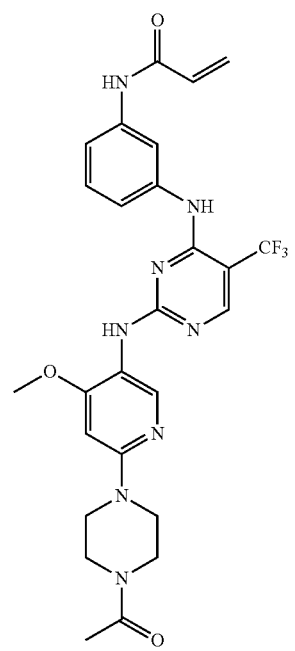
ES-075
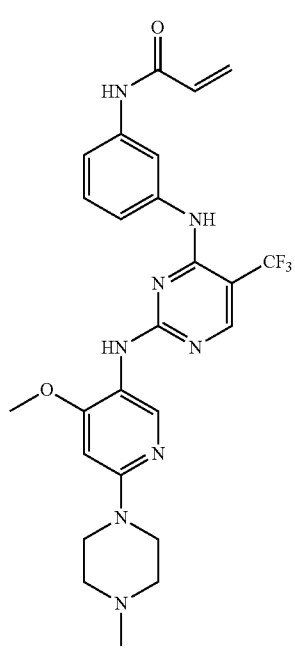

ES-0123
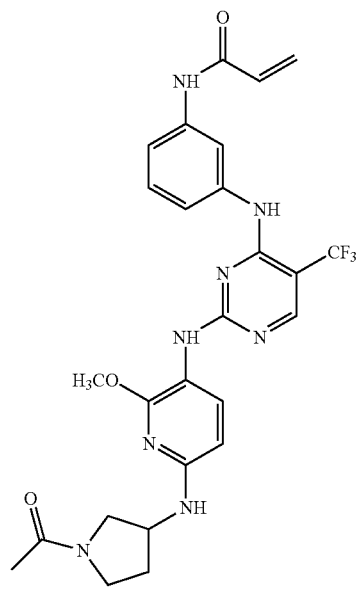
ES-0125
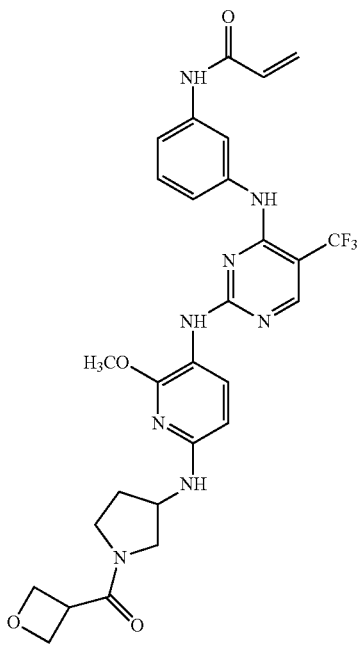
ES-0124
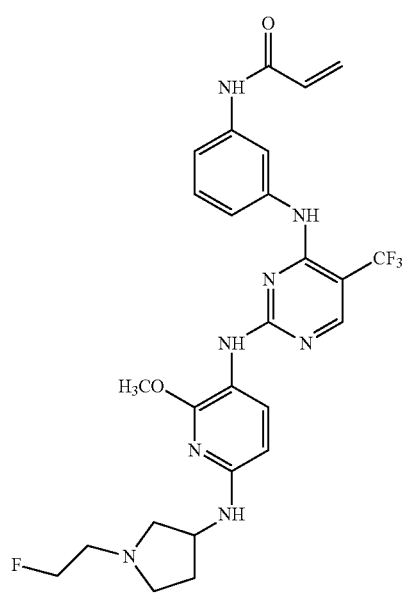
ES-0130
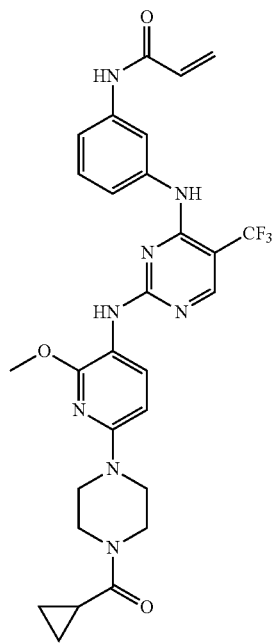

ES-0131
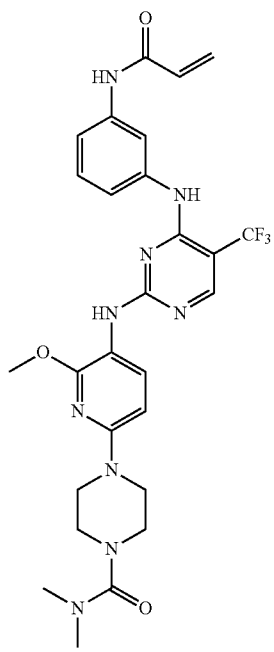
ES-0133
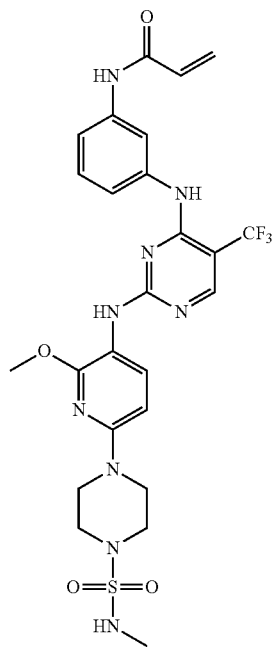
ES-0132
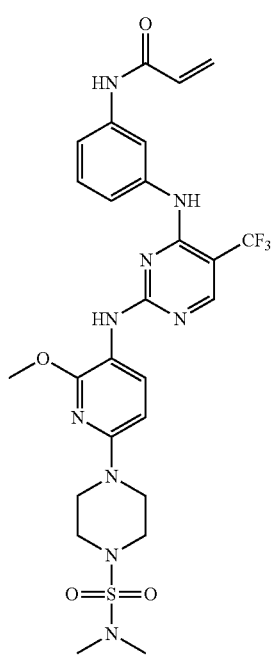
ES-0134
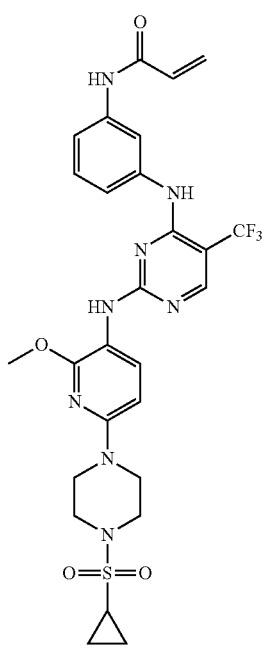

ES-0135
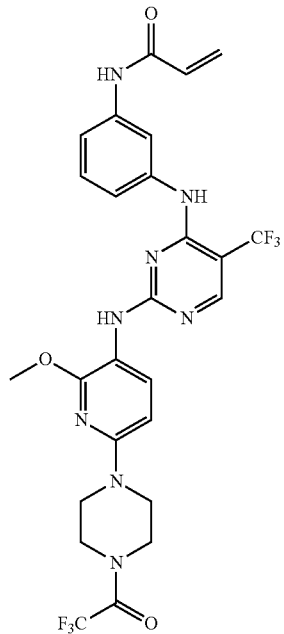
ES-0136
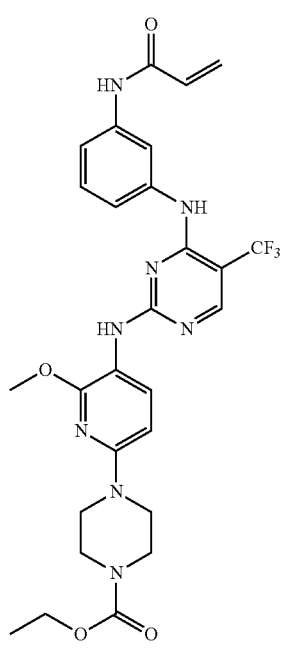
ES-0137
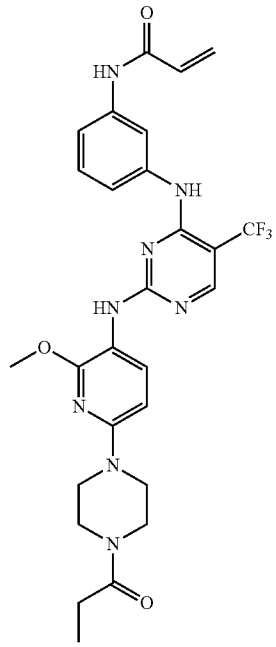
ES-0138
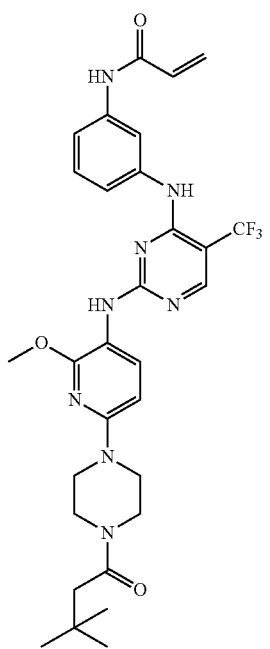

ES-0139
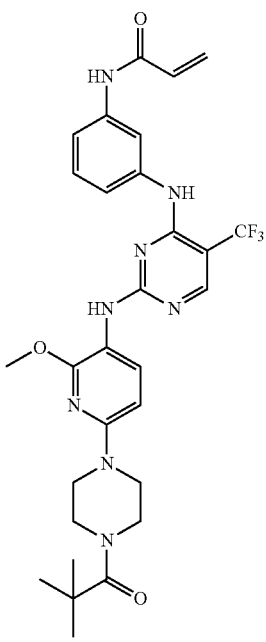
ES-0140
ES-0141
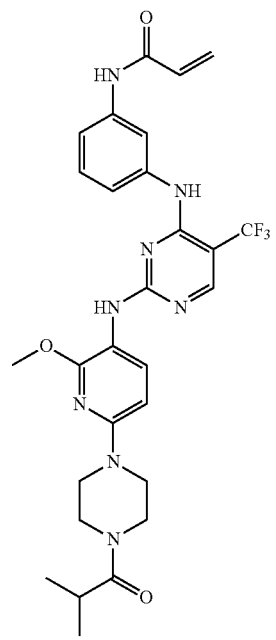
ES-0142

ES-0143
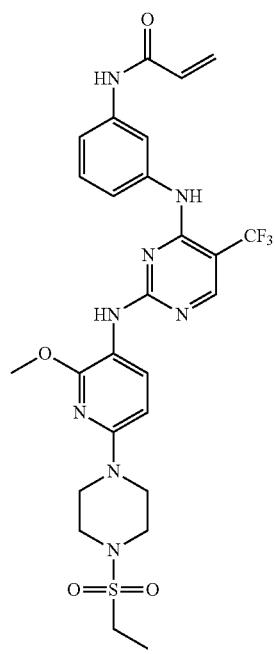
ES-145
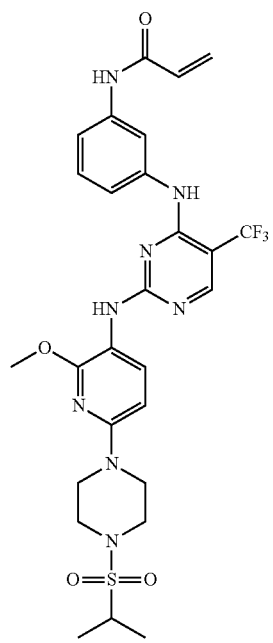
ES-0144
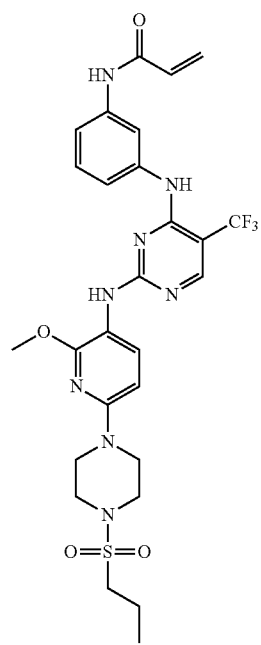
ES-146
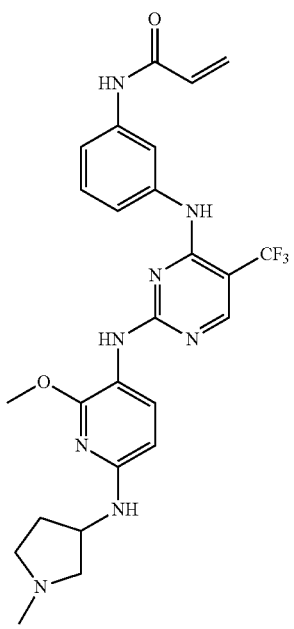

ES-147
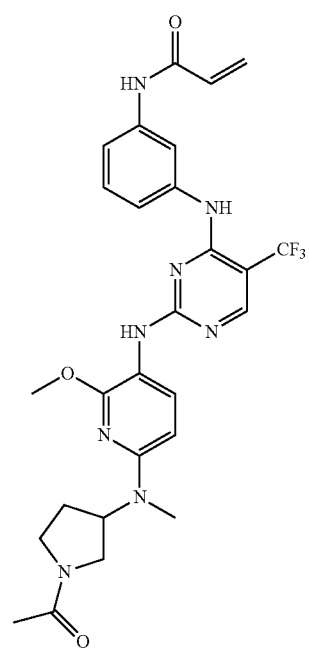
ES-148
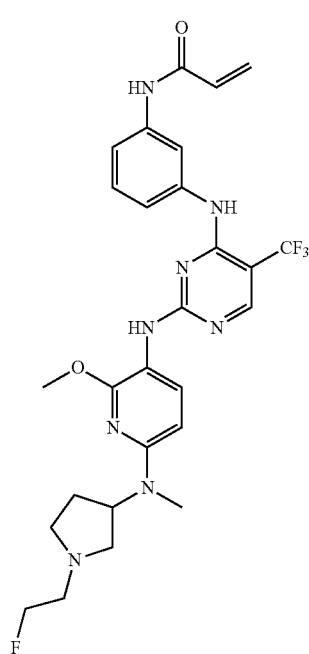
ES-149
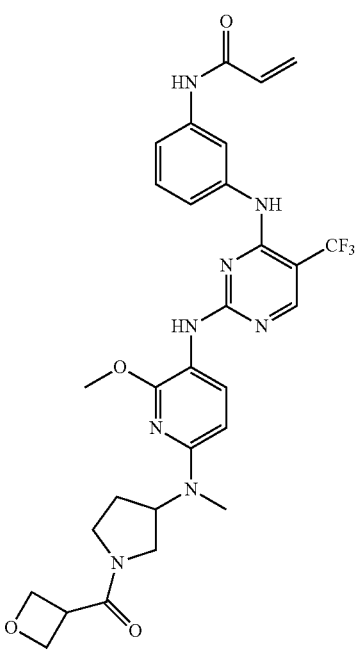
ES-150
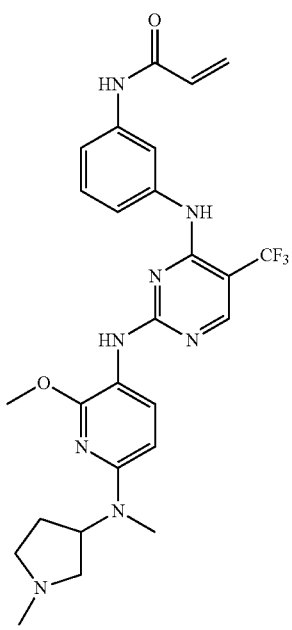

ES-151
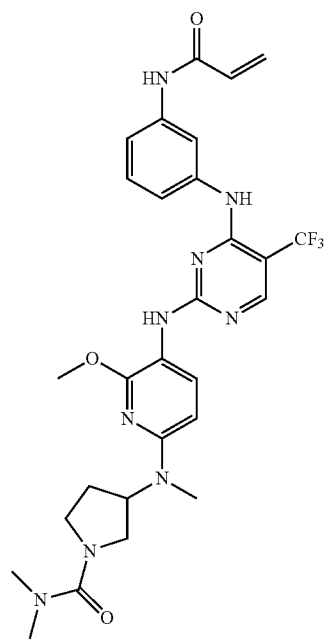
ES-157
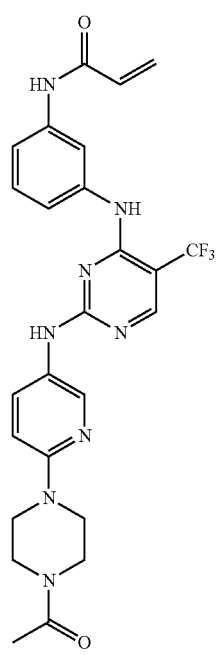
ES-158
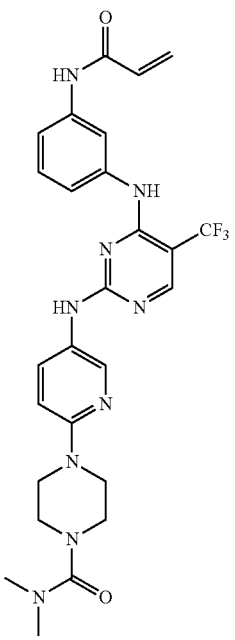
ES-159
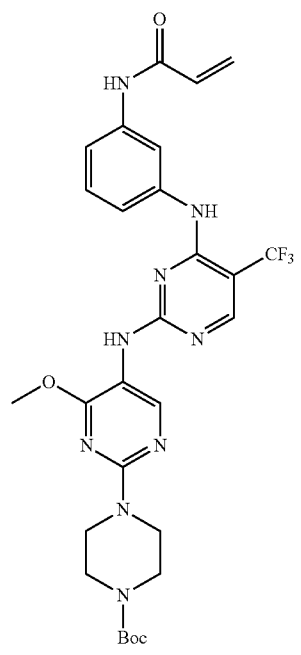

ES-160
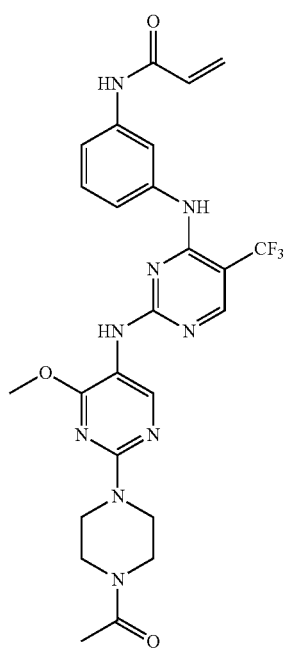
ES-163
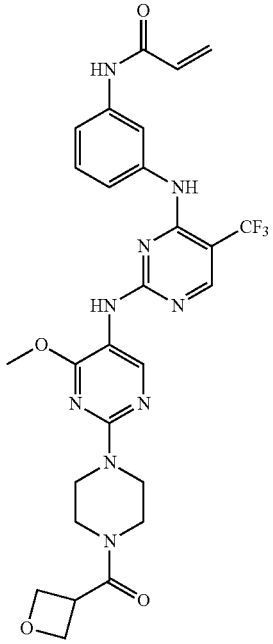
ES-161
ES-164
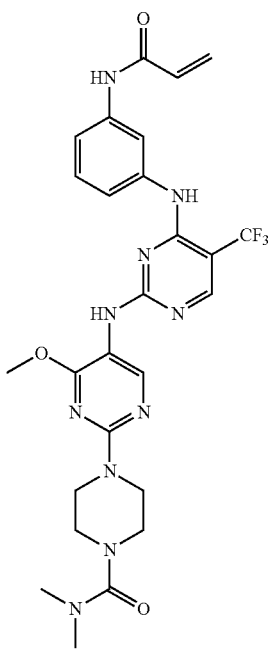
In another preferred embodiment, said compound of formula (I) is selected from the group consisting of:

ES-071
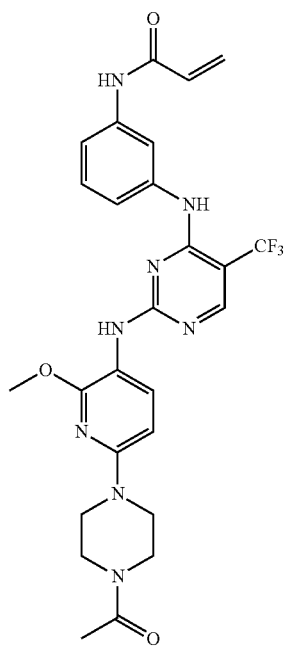
ES-075
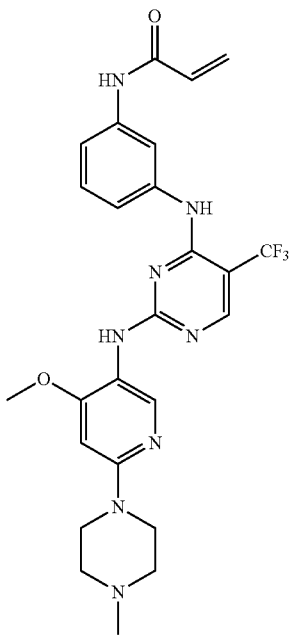
ES-072
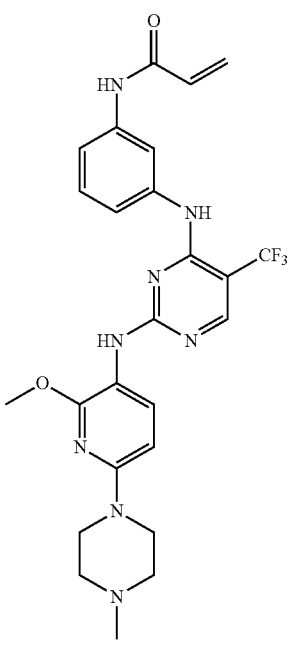
ES-0124
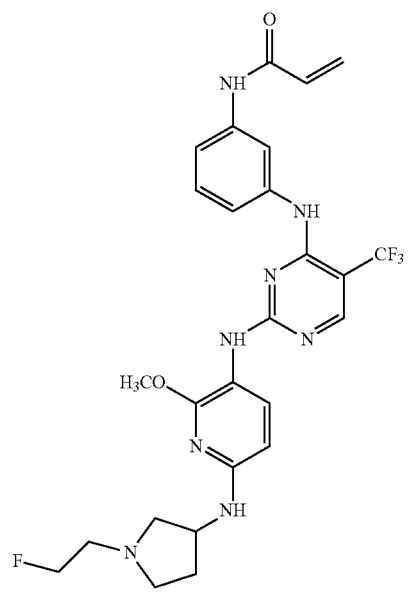

ES-0130
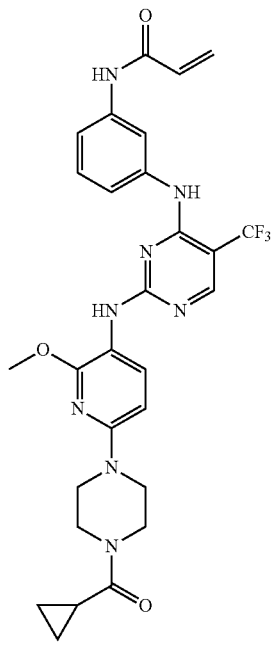
ES-0137
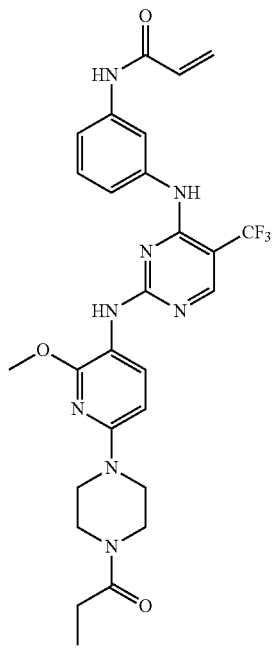
ES-146
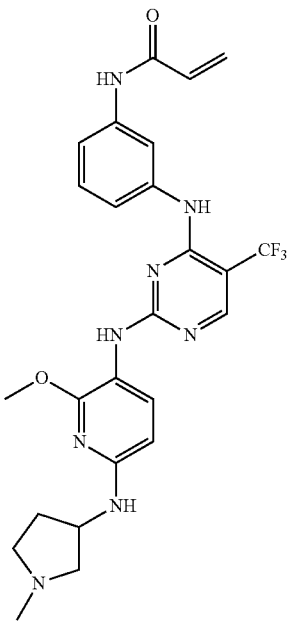
ES-148
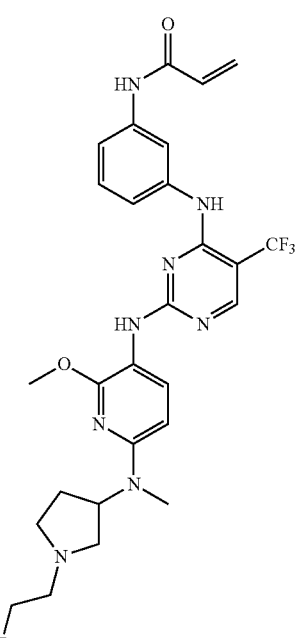

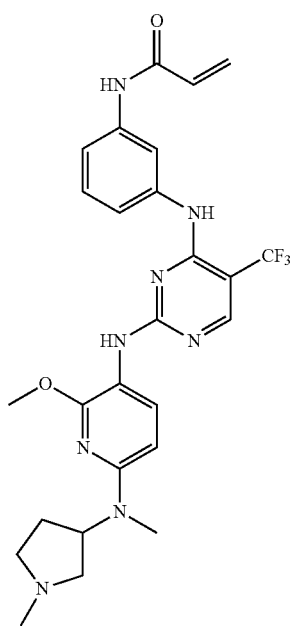
ES-150
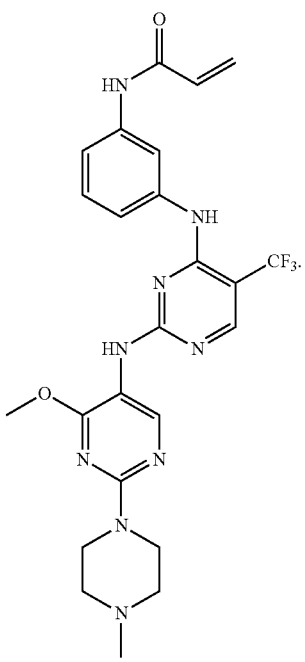
ES-161
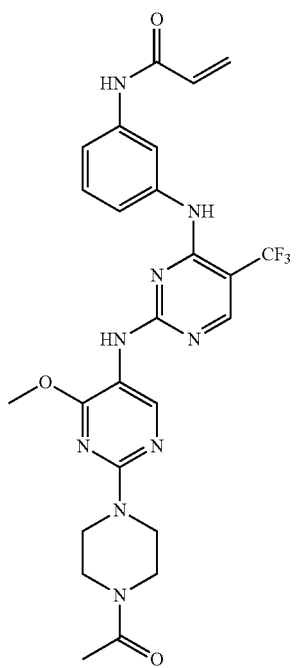
ES-160
In the second aspect of the present invention, a preparation method of compound of the first aspect of the present invention is provided, which comprises the following steps:
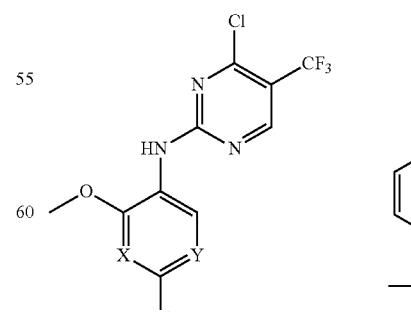
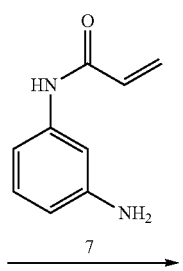

-continued

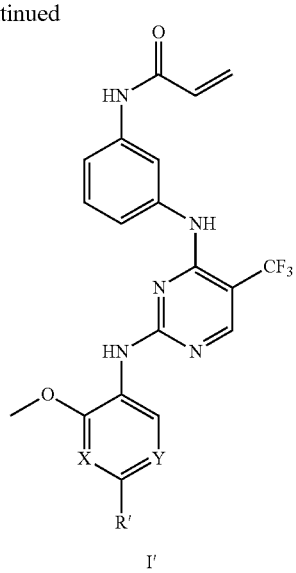

I' in an inert solvent, reacting compound of formula II with compound of formula 7, thus obtaining compound of formula I';

wherein R' is selected from the group consisting of: unsubstituted 5-7 membered heterocycles or 5-7 membered heterocycles substituted by 1-5 substituents, C1-C6 alkyl-(unsubstituted 5-7 membered heterocycles or substituted 5-7 membered heterocycles substituted by 1-5 substituents), —NH-(unsubstituted 5-7 membered heterocycles or 5-7 membered heterocycles substituted by 1-5 substituents), —N(CH$_3$)-(unsubstituted 5-7 membered heterocycles or 5-7 membered heterocycles substituted by 1-5 substituents), wherein the heterocycles contain at least one heteroatom selected from the group consisting of N, O and S; the substitution means one or more hydrogen atoms on the group are replaced by R$_1$ substituents;

while the remaining groups are defined as in the first aspect of the present invention.

In another preferred embodiment, in the steps, R' is selected from the group consisting of: unsubstituted 5-7 membered heterocycles or 5-7 membered heterocycles substituted by 1-5 substituents, C1-C6 alkyl-(unsubstituted 5-7 membered heterocycles or 5-7 membered heterocycles substituted by 1-5 substituents), —NH-(unsubstituted 5-7 membered heterocycles or 5-7 membered heterocycles substituted by 1-5 substituents), —N(CH$_3$)-(unsubstituted 5-7 membered heterocycles or 5-7 membered heterocycles substituted by 1-5 substituents), wherein the heterocycles contain at least one heteroatom selected from the group consisting of N, O and S; the substitution means one or more hydrogen atoms on the group are replaced by tert-butoxycarbonyl substituents.

In another preferred embodiment, the reaction is carried out by catalyzed with p-toluenesulfonic acid, trifluoroacetic acid or camphorsulfonic acid, preferably p-toluenesulfonic acid.

In another preferred embodiment, the inert solvent is selected from the group consisting of NMP, trifluoroethanol, dioxane, or combinations thereof.

In another preferred embodiment, the reaction is performed at 110-130° C.

In another preferred embodiment, the reaction time is 0.1-2 h.

Preferably, the method further includes the following steps:

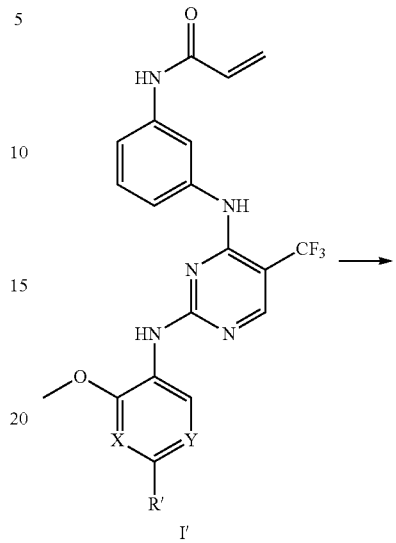

I'

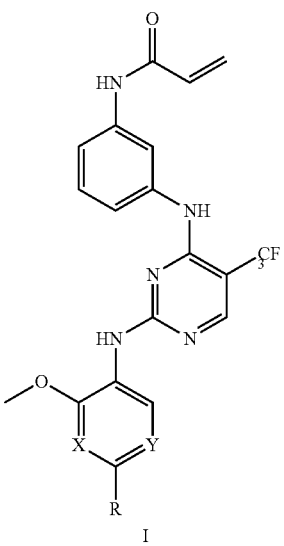

I preparing the compound of formula I from a compound of formula I';

wherein R≠R'.

In another preferred embodiment, in said R', the substituent R$_1$ is tert-butoxycarbonyl.

In another preferred embodiment, the method includes the following steps:

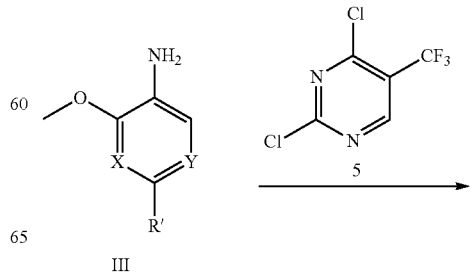

III

-continued

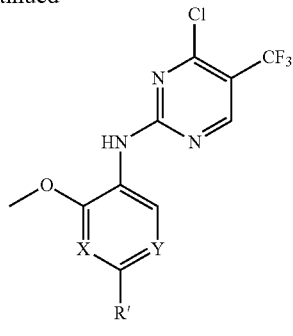

in an inert solvent, reacting compound of formula III with compound of formula 5, thereby obtaining compound of formula II;

wherein R' is defined as in the second aspect of the present invention, and the remaining groups are defined as in the first aspect of the present invention.

In another preferred embodiment, the reaction is performed with the existence of ZnCl$_2$ or ZnBr$_2$.

In another preferred embodiment, the inert solvent is selected from the following group consisting of TEA, DCE, t-BuOH, THF.

In the third aspect of the present invention, a pharmaceutical composition is provided, wherein the pharmaceutical composition comprises: a therapeutically effective amount of one or more of the compound of formula (I) according to the first aspect of the present invention, or pharmaceutically acceptable salts, tautomers, optical isomers, and pharmaceutically acceptable solvates thereof, and optionally pharmaceutically acceptable carriers, excipients, adjuvants, accessories and/or diluents.

In another preferred embodiment, the pharmaceutical composition is used to treat diseases associated with tyrosine kinase overexpression and/or tyrosine kinase hyperactivity.

In the fourth aspect of the present invention, an EGFR inhibitor is provided, wherein the inhibitor comprises an inhibitory effective amount of one or more of the compound of formula I according to the first aspect of the present invention, or pharmaceutically acceptable salts, tautomers, optical isomers, and pharmaceutically acceptable solvates thereof, and optionally pharmaceutically acceptable carriers, excipients, adjuvants, accessories and/or diluents.

In another preferred embodiment, the pharmaceutically acceptable salt is a salt of the compound of formula I, which is selected from the group consisting of inorganic acid salts, organic acid salts, alkyl sulfonates, aryl sulfonates, or combinations thereof. Preferably, the salt is selected from the group consisting of hydrochloride, hydrobromide, nitrate, sulfate, phosphate, formate, acetate, propionate, benzoate, maleate, fumarate, succinate, tartrate, citrate, methanesulfonate, ethylsulfonate, benzenesulfonate, p-toluenesulfonate, or combinations thereof;

The pharmaceutically acceptable solvate refers to a solvate of the compound of formula I with a solvent selected from the group consisting of water, ethanol, isopropanol, diethyl ether, acetone, or combinations thereof.

In the fifth aspect of the present invention, a use of the compound of formula (I) of the first aspect of the present invention is provided, wherein the compound is used in one or more of the following group:

(a) preparing tyrosine kinase inhibitors;
(b) in vitro non-therapeutically inhibiting tyrosine kinase activity;
(d) in vitro non-therapeutic inhibiting tumor cell growth;

In another preferred embodiment, the epidermal growth factor receptor activity-associated disease is selected from the group consisting of abnormal cell proliferation, morphological changes, hyperkinesia, angiogenic diseases, tumor growth, tumor metastatic disease, or the combinations thereof.

In another preferred example, the tumor cell is H1975 cell.

In another preferred example, the IC$_{50}$ value of the inhibition is ≤50 nM.

In the sixth aspect of the present invention, a compound of formula II is provided:

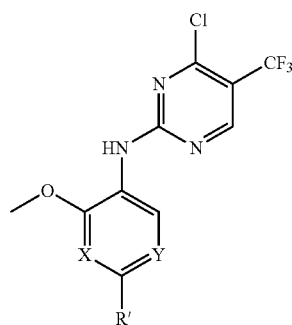

wherein the R' is defined as in the second aspect of the present invention.

In the seventh aspect of the present invention, a compound of formula III is provided:

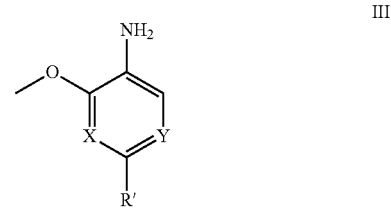

wherein the R' is defined as in the second aspect of the present invention.

In another preferred example, said R' is selected from the group consisting of:

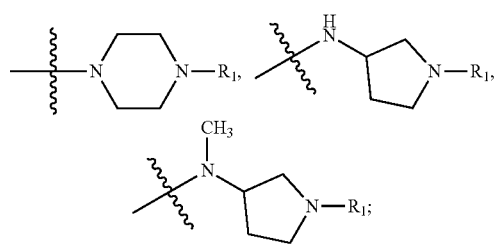

wherein the R1 is defined as in the first aspect of the present invention.

In the eighth aspect of the present invention, a method for treating or preventing diseases associated with EGFR kinase activity and/or expression is provided, wherein comprising: administering to the subject in need with an treatment or prevention effective amount of the compound of formula I.

In the ninth aspect of the present invention, a method for inhibiting EGFR kinase activity and/or tumor cell growth is provided, which comprises: administering to the subject to inhibit with an inhibitory effective amount of the compound of formula (I).

It should be understood that, in the present invention, each of the technical features specifically described above and below (such as those in the Examples) can be combined with each other, thereby constituting new or preferred technical solutions which need not be specified again herein.

DETAILED DESCRIPTION OF THE INVENTION

Figure 1:
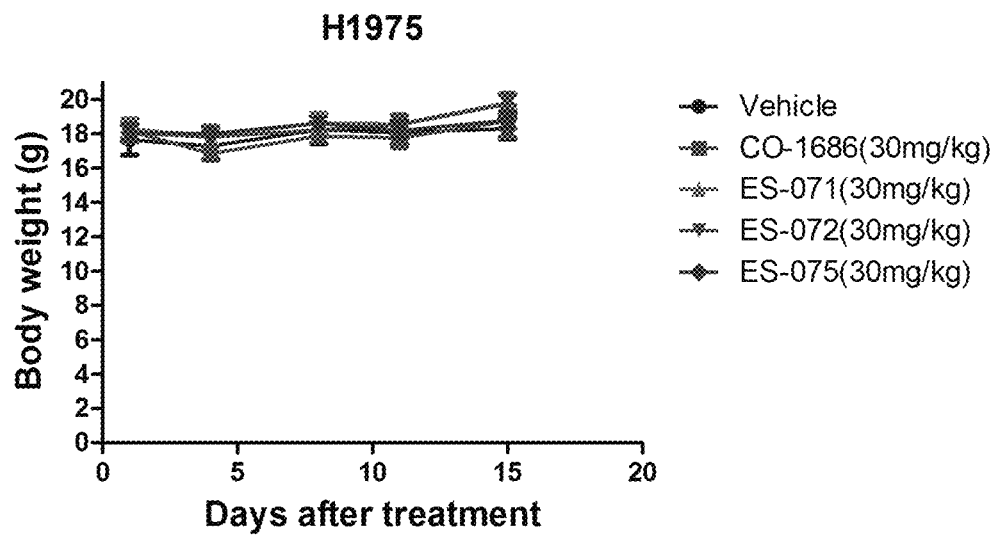
FIG. 1 shows the effect of the drug in Test Example 2 on the body weight of tumor-bearing nude mice.

Through long-term and in-depth studies, the inventors has structurally modificated the EGFR inhibitors, and unexpectedly discover that the activity of the compound is significantly improved after changing the phenyl ring connected to the piperazine ring in the existing EGFR inhibitor to pyridine or pyrimidine. The present invention is completed on this basis.

Terms

In the present invention, the alkyl group includes a linear or branched alkyl group, and the halogen is F, Cl, Br or I, preferably F or Br.

In particular, in the present invention, unless otherwise indicated, atoms mentioned include all isotope forms, for example, when referring to "hydrogen atom", it means hydrogen atom, deuterium atom, tritium atom or combinations thereof. In the present invention, the abundance of various isotopic atoms of an element may be a state in which the element is naturally occurring in nature, or may be an isotopically enriched state.

As used herein, the term "C1-C6 alkyl" refers to a linear or branched alkyl with 1 to 6 carbon atoms, such as methyl, ethyl, propyl, isopropyl, butyl, isobutyl, sec-butyl, tert-butyl, or similar groups.

In particular, unless specifically stated otherwise, in the present invention, when the number of carbon atoms of the group is not defined, it means a group having 1 to 10 carbon atoms, preferably 1 to 4 carbon atoms.

The term "5-7 membered heterocycle" refers to a heterocyclic group having 5 to 7 carbon atoms or heteroatoms (selected from N, O, S) and may be a saturated or partially unsaturated cyclic group, such as tetrahydrogenpyrrolyl, hexahydropyridinyl, or similar groups.

The term "C1~C6 alkoxy" refers to a straight or branched chain alkoxyl group having 1 to 4 carbon atoms, such as methoxy, ethoxy, propoxy, isopropoxy, butoxy, iso-butoxy, sec-butoxy, tert-butoxy, or the like.

The term "alkylacyl group" refers to groups which process "—CO-alkyl" structure, such as methyl acyl, ethyl acyl, propyl acyl, isopropyl acyl, butyl acyl, isobutyl acyl, sec-butyl acyl, tert-butyl acyl, or the like.

The term "ester group" or "oxy-acyl" can be used interchangeably, which refers to groups having the structure of "—O—CO-alkyl", such as methyl ester, ethyl ester, propyl ester, isopropyl ester, butyl ester, isobutyl ester, sec-butyl ester, tert-butyl ester, or the like.

The term "alkyl ester group" or "alkoxy acyl group" can be used interchangeably, which refers to groups having an "alkyl-O—CO-alkyl" structure, such as methyl carbomethoxy, ethyl carbomethoxy, propyl ethoxycarbonyl isopropyl carbomethoxy, or the like.

The term "pharmaceutically acceptable solvate" refers to a solvate of the corresponding compound with water, ethanol, isopropanol, diethyl ether, or acetone.

In the present invention, a "therapeutically effective amount" refers to a dose capable of achieving a desired therapeutic effect in a subject in need without causing excessive negative effects. After the structure of the compound of the present invention is disclosed, the above-mentioned dosage can be generally determined by those skilled in the art according to actual needs.

Compound of Formula I

The present invention provides a compound of the following formula (I):

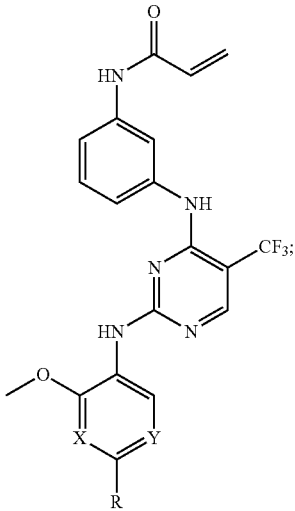

wherein:

X, Y are each independently selected from the group consisting of N, CH; with the proviso that X and Y are not CH at the same time;

R is selected from the group consisting of: unsubstituted 5-7 membered heterocycles or 5-7 membered heterocycles substituted by 1-5 substituents, C1-C6 alkyl-(unsubstituted 5-7 membered heterocycles or 5-7 membered heterocycles substituted by 1-5 substituents), —NH-(unsubstituted 5-7 membered heterocycles or 5-7 membered heterocycles substituted by 1-5 substituents), —N(CH$_3$)-(unsubstituted 5-7 membered heterocycles or 5-7 membered heterocycles substituted by 1-5 substituents), wherein the heterocycles contain at least one heteroatom selected from the group consisting of N, O and S; the substitution means one or more hydrogen atoms on the group are replaced by $R_1$ substituents;

wherein the $R_1$ is selected from the group consisting of: unsubstituted or halogenated C1-C6 alkyl, C3-C8 cycloalkyl, unsubstituted or halogenated C1-C6 alkoxy, C3-C8 cycloalkyloxy, —C(O)—$R_2$, C2-C8 alkylacyl, C2-C8 alkoxyacyl, —S(O)$_2$—$R_2$, —SOR$_2$;

the $R_2$ is selected from the group consisting of unsubstituted or halogenated C1-C6 alkyl, unsubstituted or halogenated C1-C6 alkoxy, C3-C8 cycloalkyl, C3-C8 cycloalkoxy, —CH$_2$—OAc, —NH$_2$, —NH(C1-C6 alkyl), —N(C1-C6 alkyl)$_2$.

In another preferred example, the X is N, and Y is CH.

In another preferred example, said R is selected from the group consisting of:

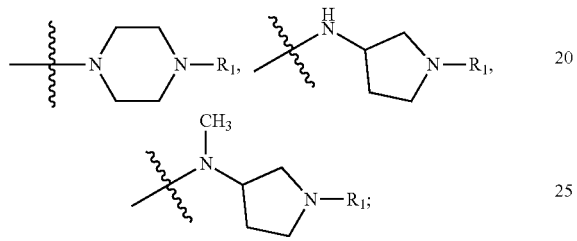

wherein the $R_1$ is selected from the group consisting of: unsubstituted or halogenated C1-C6 alkyl, C3-C8 cycloalkyl, unsubstituted or halogenated C1-C6 alkoxy, C3-C8 cycloalkyloxy, —C(O)—$R_2$, -Boc, —S(O)$_2$—$R_2$, —CH$_2$—OAc;

the $R_2$ is selected from the group consisting of unsubstituted or halogenated C1-C6 alkyl, unsubstituted or halogenated C1-C6 alkoxy, C3-C8 cycloalkyl, C3-C8 cycloalkoxy, —CH$_2$—OAc, —NH$_2$, —NH(C1-C6 alkyl), —N(C1-C6 alkyl)$_2$.

The most preferred compounds of the present invention include the individual compounds listed above and below in the present invention.

The Synthesis of Compound of Formula I

The compounds of formula I can be prepared by conventional methods in the art, for example, by antisynthetic method. After the structures of the compounds of formula I are disclosed in the present invention, the above methods of preparation are within the capabilities of those skilled in the art.

It should be noticed that, unlike the preparation methods of similar compounds in the prior art, the inventors adopt a method different from the prior art to form the core skeleton for preparing the compounds of the present invention.

In the prior art, 2,4-dichloro-5-trifluoromethylpyrimidine is firstly substituted by 3-tert-butoxycarbonylcarboxanilide, then an acryloyl group is attached to the nitrogen on aniline and reacted with the

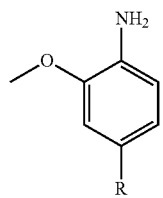

unit so as to build a compound skeleton.

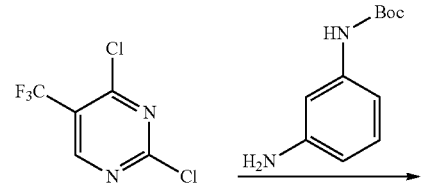

Step 1

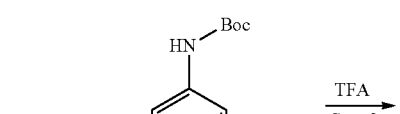

Step 2

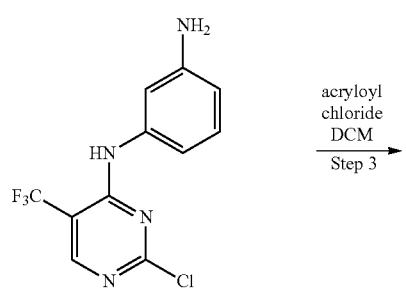

Step 3

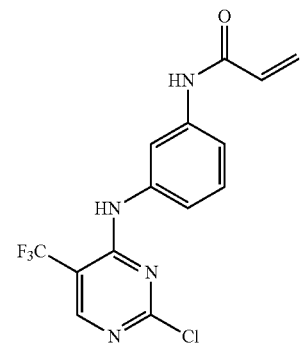

Intermediate 1

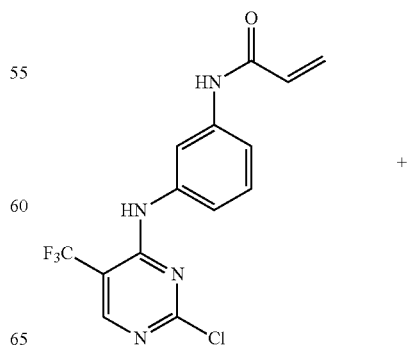

+

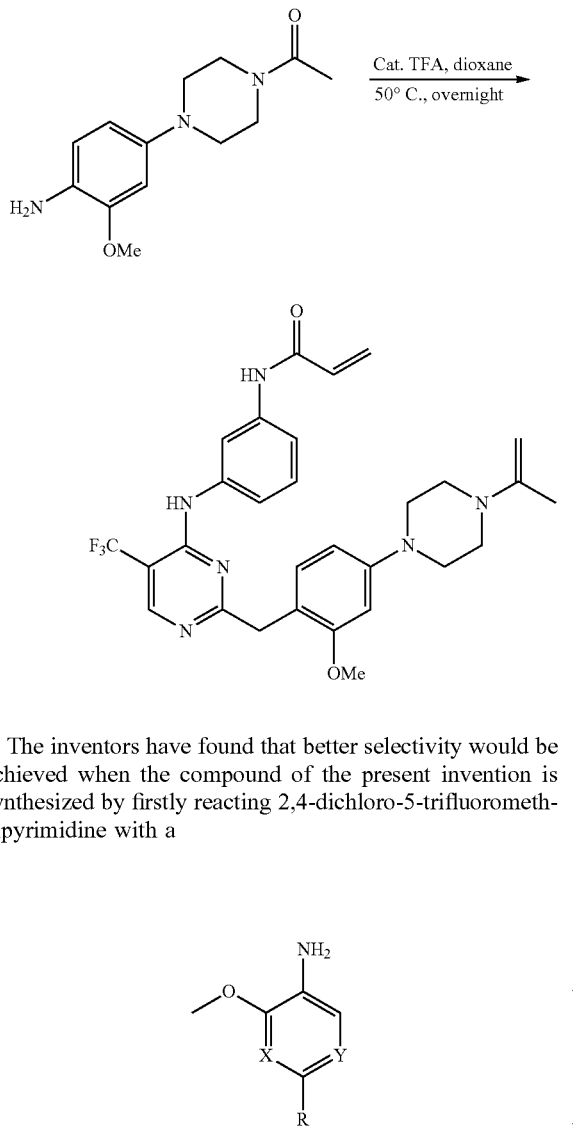

The inventors have found that better selectivity would be achieved when the compound of the present invention is synthesized by firstly reacting 2,4-dichloro-5-trifluoromethylpyrimidine with a

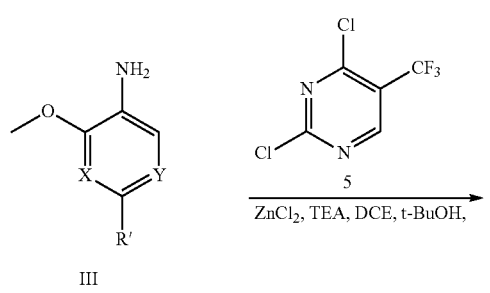

unit, and then reacting with 3-acrylamidoaniline as described in the present invention.

A preferred general synthesis method of the compound of the present invention is as follows:

The specific implementations of each step are as follows:

step 1: in an inert solvent, reacting compound of formula III with compound of formula 5, thus obtaining compound of formula II;

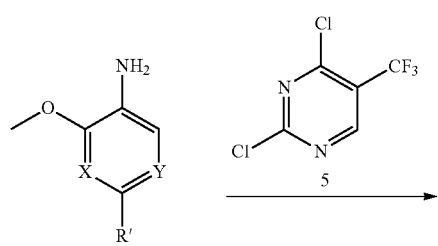

III

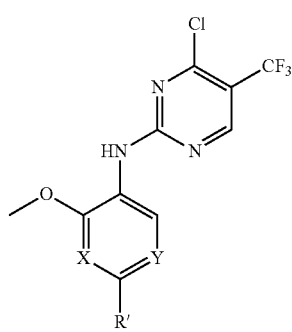

II

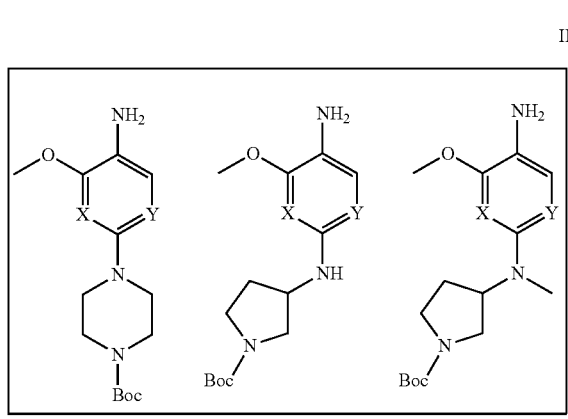

(preferred structures of compound of formula III)

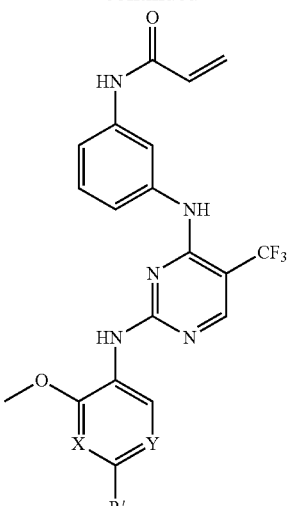

I'

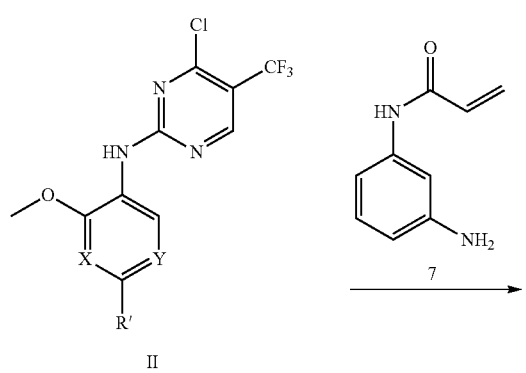

(preferred structures of compound of formula II)

step 2: in an inert solvent, reacting compound of formula II with compound of formula 7, thus obtaining compound of formula I';

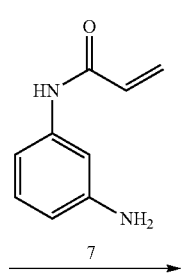

In another preferred example, in step 2, the reaction may be performed by one or more methods selected from the group consisting of:

method 1: in NMP, with the existence of p-TsOH.H$_2$O, reacting compound of formula II with compound of formula 7, thus obtaining compound of formula I';

method 2: in TFE (trifluoroethanol), with the existence of TFA, reacting compound of formula II with compound of formula 7, thus obtaining compound of formula I';

method 3: in dioxane, with the existence of Pd(OAc)$_2$, XantPhos and Cs$_2$CO$_3$, reacting compound of formula II with compound of formula 7, thus obtaining compound of formula I'.

step III. deprotecting the compound of formula I' under acidic conditions to remove t-butyloxycarboryl, and then react with the corresponding reagent under basic conditions to give formula I;

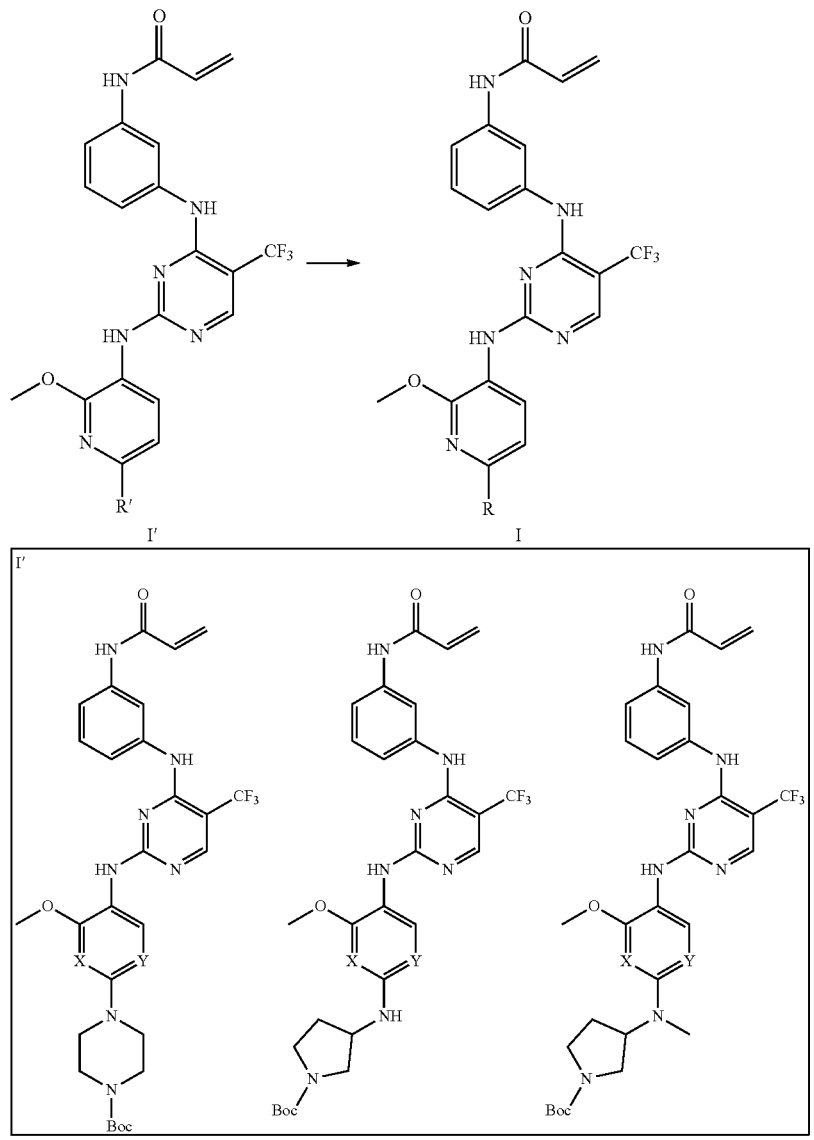

In another preferred embodiment, in step 3, the preparation of compound of formula I (the starting material is formula I' from which tert-butoxycarbonyl is removed, which is usually the corresponding amine) adopts any one selected from the group consisting of the following groups A to G:

A. in DCM, in the presence of TEA, reacting R₂COCl with a compound of formula I' from which tert-butoxycarbonyl is removed to afford the compound of formula I;

B. in DCM, in the presence of TEA, reacting (R₂CO)₂O with a compound of formula I' from which tert-butoxycarbonyl is removed to afford the compound of formula I;

C. in DCM, in the presence of TEA, reacting R₂SO₂Cl with a compound of formula I' from which tert-butoxycarbonyl is removed to afford the compound of formula I;

D. in DMF or the combinations thereof, in the presence of HATU and DIEA, reacting R₂COOH with a compound of formula I' from which tert-butoxycarbonyl is removed to afford the compound of formula I;

E. in DMF, in the presence of DIEA, reacting R₁X with a compound of formula I' from which tert-butoxycarbonyl is removed to afford the compound of formula I;

F. in DMF, in the presence of cesium carbonate, reacting R₁X with a compound of formula I' from which tert-butoxycarbonyl is removed to afford the compound of formula I;

G. in methyl alcohol, in the presence of AcOH, reacting HCHO with a compound of formula I' from which tert-butoxycarbonyl is removed, and then adding sodium cyanoborohydride for further reaction to afford the compound of formula I;

In the above formula, R₂COCl, (R₂CO)₂O, R₂SO₂Cl, R₂COOH or R₁X (X is halogen) is a raw material corresponding to the target compound of formula I.

Pharmaceutically Acceptable Salts and Solvates

Pharmaceutically acceptable forms of the compounds of this invention may include the compound itself or other pharmaceutically acceptable variations, such as optical isomers, cis-trans isomers and the like, or pharmaceutically acceptable salts or solvates.

Preferably, the pharmaceutically acceptable salts include, but are not limited to, inorganic acid salts such as hydrochlorides, hydrobromides, nitrates, sulfates, phosphates, etc.; organic acid salts such as formates, acetates, propionates, benzoates, maleates, fumarates, succinates, tartrates, citrates, etc.; alkyl sulfonates, such as methyl sulfonates, ethyl sulfonates, etc.; aryl sulfonates, such as benzene sulfonates, p-toluene sulfonates, and the like.

Preferably, the pharmaceutically acceptable solvates include, but are not limited to, solvates of the compound formed with water, ethanol, isopropanol, diethyl ether, acetone and the like.

Uses of Compound of Formula I

According to studies, the compound of formula I according to the present invention has an epidermal growth factor receptor (EGFR) inhibitory activity. Therefore, any one or more of the compounds of formula I according to the present invention, or the derivatives, or the tautomers, racemates, enantiomers, diastereomers, diastereomers, pharmaceutically acceptable salts, pharmaceutically acceptable solvates thereof can be used to prepare tyrosine-kinase inhibitor, particularly applicable to prepare EGFR inhibitors.

At the same time, the inhibitors can be used in the preparation of drugs for preventing or treating EGFR related diseases. Specifically, it can be applied to the preparation of a medicament for preventing or treating abnormal cell proliferation, morphological changes, hyperkinesia, angiogenesis, and tumor metastasis associated with EGFR.

In addition, the inhibitors can be applied to the preparation of a medicament for treating or preventing tumor growth and metastasis associated with epidermal growth factor receptor EGFR.

The active ingredient of the inhibitor described in this patent is preferably any one or more of the specific compounds shown in the present invention, or the tautomers, racemates, enantiomers, diastereomers, diastereomers, pharmaceutically acceptable salts, or pharmaceutically acceptable solvates thereof.

Pharmaceutical Composition and Use Thereof

Another aspect of the present invention provides a pharmaceutical composition comprising a therapeutically effective amount of one or more of compounds of general formula (I), or pharmaceutically acceptable salts, enantiomers diastereomers or racemates thereof, and optionally one or more pharmaceutically acceptable carriers, excipients, adjuvants, accessories and/or diluents. The accessories are, for example, odorants, flavoring agents, sweeteners, and the like.

The pharmaceutical composition provided by the present invention preferably contains the active ingredient in a weight ratio of 1 to 99%. Preferably, the compound of the general formula I accounts for 65 wt % to 99 wt % of the total weight as the active ingredient, and the rest are pharmaceutically acceptable carriers, diluents, solutions or salt solutions.

The compounds and pharmaceutical compositions provided by the present invention may be in various forms, such as tablets, capsules, powders, syrups, solutions, suspensions, aerosols, etc., and may be present in suitable solid or liquid carriers or diluents, and in disinfectors suitable for injection or instillation.

Various dosage forms of the pharmaceutical compositions of the present invention can be prepared according to the conventional preparation methods in the pharmaceutical field. The unit dosage of its formulation formula comprises 0.05-200 mg of the compound of formula I, preferably, the unit dosage of the formulation formula contains 0.1 mg-100 mg of the compound of formula I.

The compounds and pharmaceutical compositions of the present invention can be used clinically in mammals, including humans and animals, and can be administered via mouth, nose, skin, lung or gastrointestinal tract. Most preferred is oral. The most preferred daily dose is 0.01-200 mg/kg body weight in one dose, or 0.01-100 mg/kg body weight in divided doses. Regardless of the administering method, the individual's optimal dose should be based on the specific treatment. Usually, it starts with a small dose, which is gradually increased until the most suitable dose is found.

A further aspect of the present invention provides an EGFR inhibitor comprising one or more of the compounds of formula I, the pharmaceutically acceptable salts, isomers or mixtures thereof, and optionally one or more pharmaceutically acceptable carriers, excipients, adjuvants, excipients and/or diluents.

The compounds and compositions of the present invention are useful for the treatment and prevention of metabolic disorder associated with EGFR, including but not limited to diseases such as diabetes, atherosclerosis, obesity, and the like.

Therefore, a further aspect of the present invention provides the compounds of general formula I, the pharmaceutically acceptable salts, isomers, or mixtures thereof for use in the preparation of drugs for treatment of a metabolic disorder associated with EGFR activity, for example: diabetes, atherosclerosis, obesity, and the like.

Yet another aspect of the present invention provides a method of treating metabolic disorders associated with EGFR activity or expression levels, such as diabetes, atherosclerosis, obesity, and the like, which include administering to a patient in need of such treatment with one or more of the compounds of the above general formula I, the pharmaceutically acceptable salts, isomers, or mixtures thereof.

Compared with the Prior Art, the Main Advantages of the Present Invention Include:

(1) It provides a novel structure of a compound with EGFR inhibitory activity which has lower tumor cell inhibitory concentration than the existing approximate compound, for example, compared to the control compound 1686, ES071 (only different in the benzene ring and pyridine ring structure) has a activity significantly increased, and the inhibitory concentration to most tumor cells is only ½ of the former one; and the compounds of the present invention also have extremely unexpected activity improvements when compared with the similar compound in the prior art (such as compound I-4 in CN103269704, I-1 in US2012157426).

(2) The selectivity of some of the compounds of the present invention for some tumor strains is improved when compared to the existing compounds.

(3) The compound of the present invention has different physical properties (eg, water solubility, etc.) from the existing compound, and thus can be prepared as different dosage forms.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

PREPARATION EXAMPLE

Example 1

Preparation of Intermediate II

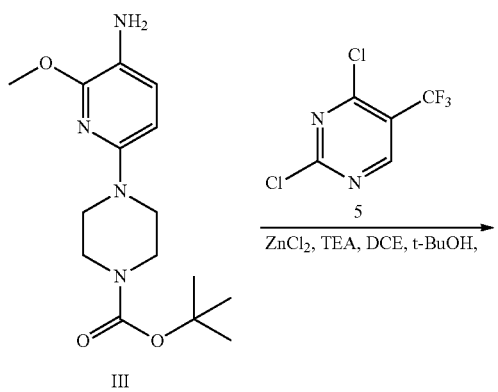

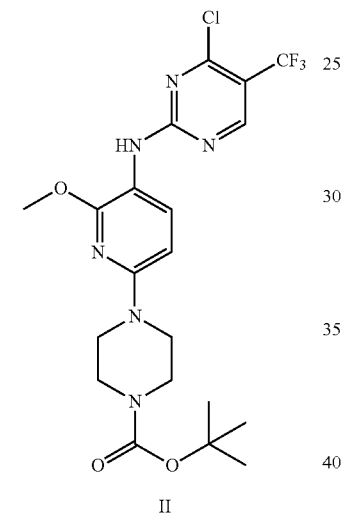

The raw material 2,4-dichloro-5-trifluoromethyl pyrimidine (4.2 g, 19.46 mmol) and 100 mL of mixture of 1,2-dichloroethane and tert-butanol (volume ratio 1:1) were added to a 500 mL reaction flask under argon protection. A 1 mol/L solution of ZnCl$_2$ in ether (42.8 mL, 42.8 mmol) was added dropwise at 0° C. in ice-bath, and the reaction was allowed to be stirred for 1 hour at room temperature after the addition of the solution was completed. The temperature was kept at 0° C., and another raw material III (6.0 g, 19.46 mmol) in 50 mL of mixed solvent of 1,2-dichloroethane and tert-butanol (1:1 by volume), and triethylamine (2.16 g, 21.4 mmol) were added dropwise successively. The mixture was naturally warmed to room temperature and reacted for 10 hours. The reaction solution was diluted with 200 mL of dichloromethane, washed with saturated aqueous sodium chloride solution (100 mL×2), dried over anhydrous sodium sulfate, and the solvent was removed by rotary evaporation. The product II and its isomers were obtained by flash column chromatography (7.61 g, yield: 80%), in which the $^1$H NMR of Compound II (400 MHz, CD$_3$OD): 1.46 (s, 9H), 3.40-3.55 (m, 8H), 3.88 (s, 3H), 6.28 (d, J=8.4 Hz, 1H), 7.86 (d, J=8.4 Hz, 1H), 8.49 (br s, 1H). ESI-MS m/z 488.9 (M+H)$^+$.

Example 2

Preparation of Intermediate I' (ES-070)

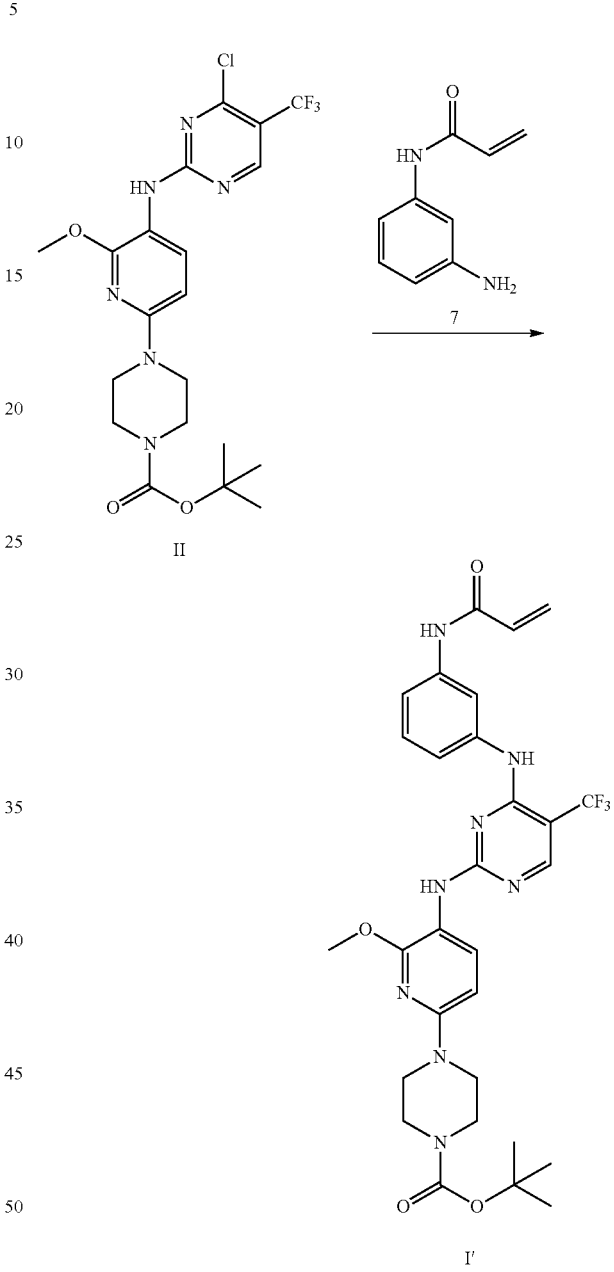

To a 100 mL reaction flask were sequentially added the above-mentioned starting material II and its isomer mixture (5 g, 10.2 mmol), raw material 3-acrylamide aniline (1.65 g, 10.2 mmol), p-toluenesulfonic acid monohydrate (0.07 g, 0.37) and solvent N-methylpyrrolidone (50 mL). The reaction solution was placed in an oil bath preheated to 120° C. and reacted for 30 min under argon. The reaction was stopped and cooled to room temperature, and the reaction was diluted by 200 mL of ethyl acetate, and washed with saturated aqueous sodium chloride solution (100 mL×4), dried over anhydrous sodium sulfate. The solvent was removed by rotary evaporation, and 2.51 g of product I' (ES-070) was obtained by flash column chromatography, yield: 40%. The $^1$H NMR (400 MHz, CD$_3$OD) of compound 8: δ1.42 (s, 9H), 3.30 (br s, 4H), 3.42 (br s, 4H), 3.81 (s, 3H), 5.70 (dd, J=9.2, 2.8 Hz, 1H), 5.90 (br s, 1H), 6.25-6.38 (m, 2H), 7.06 (br s, 1H), 7.26 (t, J=8.0 Hz, 1H), 7.50-7.70 (m, 2H), 7.79 (d, J=8.4 Hz, 1H), 8.13 (s, 1H). ESI-MS m/z 615.4 (M+H)$^+$.

Example 3

Preparation of Intermediate I'

Compound I' could also be prepared by the following method: the corresponding intermediate II prepared according to Example 1 (10.2 mmol), starting material 7 (1.65 g, 10.2 mmol), trifluoroacetic acid (114 mg 1.0 mmol, 0.1 eq.) and trifluoroethanol (60 mL) were added successively to a 100 mL reaction flask. The temperature was raised to 80° C. under argon atmosphere, and the reaction was stirred in an oil bath for 3 h. The reaction was stopped and cooled to room temperature, and diluted with 200 mL of ethyl acetate, washed with aqueous sodium chloride solution (50 mL×4) and dried over anhydrous sodium sulfate. The solvent was removed by rotary evaporation and the products I'-1, I'-2 were obtained by flash column chromatography.

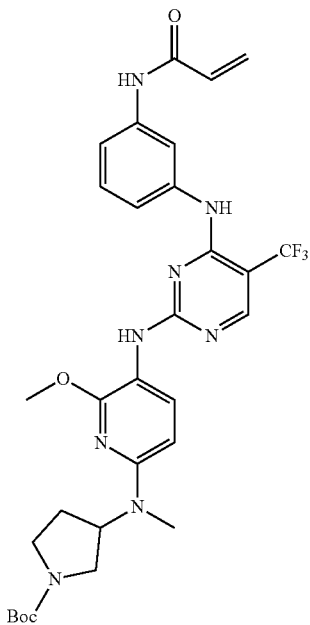

I'-1

Intermediate I'-1, yield 50%. $^1$H NMR (500 MHz, CD$_3$OD) δ (ppm): 1.46 (d, J=10.0 Hz, 9H), 1.86-1.95 (m, 1H), 2.15-2.25 (m, 1H), 3.21-3.24 (m, 1H), 3.39-3.50 (m, 2H), 3.68-3.70 (m, 1H), 3.88 (s, 3H), 4.25-4.35 (m, 1H), 5.74-6.00 (m, 2H), 6.34-6.45 (m, 2H), 7.15-7.25 (m, 1H), 7.30 (t, J=7.5 Hz, 1H), 7.50-7.80 (m, 3H), 8.18 (s, 1H). ESI-MS m/z 615.6 (M+H)$^+$.

I'-2

Intermediate I'-2, yield 50%. $^1$H NMR (400 MHz, CD$_3$OD) δ (ppm): 1.45 (s, 9H), 2.00-2.10 (m, 2H), 2.83 (s, 3H), 3.20-3.35 (m, 2H), 3.48-3.60 (m, 2H), 3.86 (s, 3H), 5.05-5.15 (m, 1H), 5.70-5.90 (m, 2H), 6.30-6.43 (m, 2H), 7.08-7.16 (m, 1H), 7.29 (t, J=7.6 Hz, 1H), 7.55-7.75 (m, 2H), 7.77 (d, J=8.8 Hz, 1H), 8.17 (s, 1H). ESI-MS m/z 629.7 (M+H)$^+$.

Example 4

Preparation of Intermediate I'

Compound I' could also be prepared by the following method: The corresponding intermediate II (1.0 mmol) prepared according to Example 1, starting material 7 (0.16 g, 1.0 mmol, 1.0 eq.), palladium acetate (34 mg, 0.15 mmol, 0.15 eq.), XantPhos (173 mg, 0.3 mmol, 0.30 eq.), cesium carbonate (326 mg, 1.0 mmol, 2.0 eq.) and solvent dioxane (30 mL) were added to a 100 mL reaction flask. The temperature was raised to 100□ under argon atmosphere, and the reaction was stirred in an oil bath for 2 h. The reaction was stopped and cooled to room temperature, and diluted with 200 mL of ethyl acetate, washed with aqueous sodium chloride solution (50 mL×4) and dried over anhydrous sodium sulfate. The solvent was removed by rotary evaporation and the products I' (ES-073, ES-159) were obtained by flash column chromatography.

ES-073

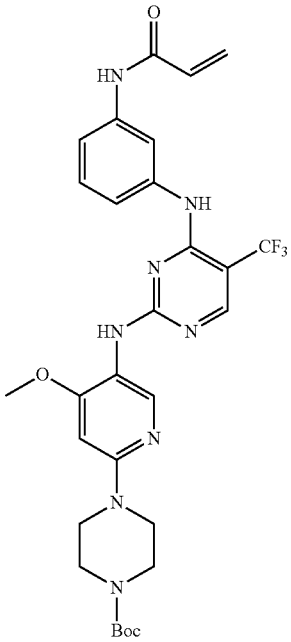

ES-073, yield 50%. ¹H NMR (500 MHz, CD₃OD) δ (ppm): 1.50 (s, 9H), 3.43-3.49 (m, 4H), 3.50-3.58 (m, 4H), 3.84 (s, 3H), 5.77 (dd, J=9.8, 1.9 Hz, 1H), 6.32-6.45 (m, 3H), 7.15-7.28 (m, 2H), 7.46 (d, J=7.8 Hz, 1H), 7.78 (brs, 1H), 8.20 (s, 1H), 8.21 (s, 1H). ESI-MS: m/z 615.6 (M+H)⁺.

ES-159

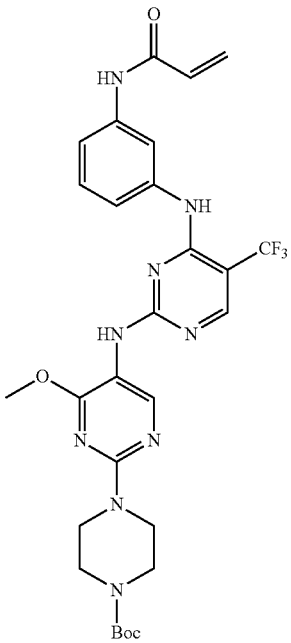

ES-159, yield 60%. ¹H NMR (500 MHz, CD₃OD) δ (ppm): 1.50 (s, 9H), 3.48 (br s, 4H), 3.73 (br s, 4H), 3.88 (s, 3H), 5.77 (dd, J=9.5, 2.0 Hz, 1H), 6.32-6.42 (m, 2H), 7.10-7.30 (m, 2H), 7.45 (d, J=7.5 Hz, 1H), 7.60-7.90 (m, 1H), 8.20 (s, 1H), 8.22 (s, 1H). ESI-MS: m/z 616.5 (M+H)⁺.

Example 5

Preparation of Compound I (ES-071)

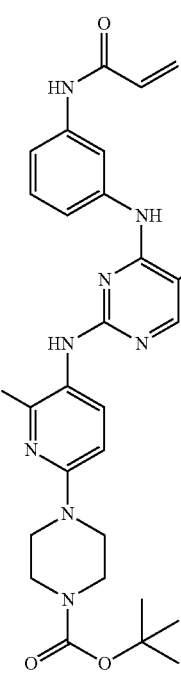

I'

1) TFA, DCM, r.t.
2) Method 1: R₁COCl, TEA, DCM or: Ac₂O, TEA, DCM

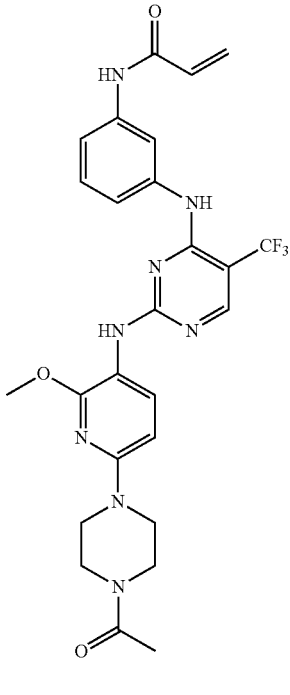

I

The product I' (2 g, 3.25 mmol) obtained above was dissolved in 20 ml of methylene dichloride, and 4 ml of trifluoroacetic acid was added dropwise at room temperature. The reaction was stirred at room temperature for 2 hours and the solvent was removed by rotary evaporation. The residue was diluted with 100 ml of dichloromethane, wash with saturated aqueous sodium bicarbonate solution and saturated sodium chloride, and dried over anhydrous sodium sulfate. The solvent was removed by rotary evaporation, and amine ES-069 was obtained in a yield of 95% by flash column chromatograph. $^1$H NMR (500 MHz, CD$_3$OD) δ (ppm): 3.04 (t, J=5.5 Hz, 4H), 3.49 (br s, 4H), 3.90 (s, 3H), 5.78 (dd, J=9.5, 2.0 Hz, 1H), 6.00 (br s, 1H), 6.34-6.45 (m, 2H), 7.15 (br s, 1H), 7.34 (t, J=8.0 Hz, 1H), 7.60-7.73 (m, 2H), 7.89 (d, J=8.5 Hz, 1H), 8.22 (s, 1H). ESI-MS m/z 515.4 (M+H)$^+$.

This compound could also be used directly in the acylation reaction of the following synthetic of compound ES-071.

Method A: Into a 100 mL reaction flask, the above-obtained amine (1 mmol), triethylamine (202 mg, 2 mmol, 2 eq.) and solvent dichloromethane (40 ml) were successively added. A solution of acetyl chloride (1.2 mmol, 1.2 eq.) in 10 ml of dichloromethane was added dropwise with stirring at room temperature, and after addition the mixture was stirred for another 2 hours at room temperature. The reaction was quenched by adding saturated aqueous sodium bicarbonate solution, separated and dried over anhydrous sodium sulfate. The solvent was removed by rotary evaporation and the final product I (ES-071) was obtained by flash column chromatography.

Method B: The amine was dissolved in 30 ml of dichloromethane, to which triethylamine (1.0 g, 9.9 mmol) was added at room temperature, and acetic anhydride (0.5 g, 4.9 mmol) in 3 ml of dichloromethane was added dropwise. The mixture was reacted at room temperature for 1 h, then the reaction mixture was washed with water (20 mL×3), dried over anhydrous sodium sulfate, and the solvent was removed by rotary evaporation. The product ES-071 was obtained by flash column chromatography (1.54 g, yield: 85%). $^1$H NMR (400 MHz, CD$_3$OD) δ (ppm): 2.13 (s, 3H), 3.35-3.50 (m, 4H), 3.59-3.66 (m, 4H), 3.87 (s, 3H), 5.75 (dd, J=8.8, 2.4 Hz, 1H), 5.95 (br s, 1H), 6.31-6.42 (m, 2H), 7.12 (br s, 1H), 7.31 (t, J=8.0 Hz, 1H), 7.60-7.66 (m, 2H), 7.85 (d, J=8.4 Hz, 1H), 8.19 (s, 1H). $^{13}$C NMR (100 MHz, DMSO): δ (ppm): 21.7, 45.3, 45.6, 53.2, 98.2, 112.3, 116.2, 116.7, 120.5, 127.2, 128.8, 125.3 (q, J=268 Hz), 130.1, 132.4, 135.0, 138.9, 139.5, 154.3, 156.2, 157.5, 161.9, 163.6, 168.8. ESI-MS m/z 557.6 (M+H)$^+$.

Example 6

Preparation of Compound I

The other compounds of formula I could be prepared by removing tert-butoxycarbonyl groups with trifluoroacetic acid according to Example 5 to prepare the corresponding amines, and then selecting the following methods depending on the different reactants:

When the amine was reacted with acyl chloride, it could be prepared by the Method A of Example 5.

When the amine was reacted with anhydride, it could be prepared by the Method B of Example 5.

When the amine was reacted with sulfonyl chloride or sulfinyl chloride, method C could be used: in to a 100 mL reaction flask, the above-obtained amine 8' (1 mmol), triethylamine (202 mg, 2 mmol, 2 eq.) and solvent dichloromethane (40 ml) were successively added. A solution of sulfonyl chloride R$_1$SO$_2$Cl (1.2 mmol, 1.2 eq.) in 10 ml of dichloromethane was added dropwise with stirring at room temperature, and the mixture was stirred to continue the reaction for 2 hours at room temperature after addition. The reaction was quenched by adding saturated aqueous sodium bicarbonate solution, and the organic phase was separated and dried over anhydrous sodium sulfate. The solvent was removed by rotary evaporation and the final product I was obtained by flash column chromatography.

When the amine was reacted with carboxylic acids, Method D could be used: To a 100 mL reaction flask were sequentially added the above-obtained amine 8' (1 mmol), carboxylic acid (1 mmol, 1 eq.), condensation reagent HATU (1.2 mmol, 1.2 eq.) and solvent DMF (20 ml). A solution of DIEA (2 mmol, 2 eq.) in 5 ml of DMF was added dropwise with stirring at room temperature, and after addition the reaction was allowed to react for 2 hours with stirring at room temperature. The reaction mixture was diluted with ethyl acetate (150 m), washed with saturated aqueous sodium chloride (40 mL×4), dried over anhydrous sodium sulfate, and the solvent was removed by rotary evaporation. The final product I was obtained by flash column chromatography.

When the amine was reacted with a halogenated hydrocarbon, method E could be used: To a 100 mL reaction flask, the above-obtained amine 8' (1 mmol), halogenated hydrocarbon R$_1$X (1.5 mmol, 1.5 eq.), DIEA (3 mmol, 3 eq.) and solvent DMF (20 ml) were successively added. The mixture was stirred at 60° C. for 12 hours, cooled to room temperature, diluted with ethyl acetate (150 ml), washed with saturated aqueous sodium chloride (40 mL×4), dried over anhydrous sodium sulfate, and the solvent was removed by rotary evaporation. The final product I was obtained by chromatography.

When the amine was reacted with a halogenated hydrocarbon, method F could be used: To a 100 mL reaction flask, the above-obtained amine 8' (1 mmol), halogenated hydrocarbon R$_1$X (1.5 mmol, 1.5 eq.), cesium carbonate (3 mmol, 3 eq.) and solvent DMF (20 ml) were successively added. The mixture was stirred at room temperature for 12 hours, diluted with ethyl acetate (150 ml), washed with saturated aqueous sodium chloride (40 mL×4), dried over anhydrous sodium sulfate, and the solvent was removed by rotary evaporation. The final product I was obtained by chromatography.

The N-methylation reaction of amine could be conducted by method G: To a 100 mL reaction flask were sequentially added the above-obtained amine 8' (1 mmol), 37% aq HCHO (3 mmol), AcOH (1.1 mmol) and solvent methanol (50 ml), and the mixture was heated at 60° C. for 1 hour to carry out the reaction. After the reaction liquid was cooled to 0° C., 10 ml of dichloromethane was added, sodium cyanoborohydride (1 mmol) was then added in portions, and the mixture was further reacted at 0° C. for 1 hour to complete the reaction. The reaction mixture was diluted with 150 ml of dichloromethane, washed with water, dried over anhydrous sodium sulfate, and the solvent was removed by rotary evaporation, and the final methylated product I was obtained by flash column chromatography.

The structural characterization data for each compound were as follows:

For ES-072:

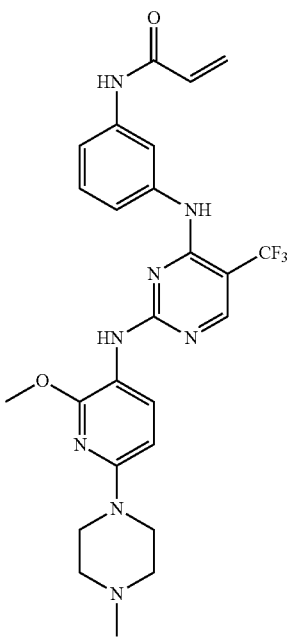
ES-072

The synthesis was conducted according to method G, yield 80%. $^1$H NMR (400 MHz, CD$_3$OD) δ (ppm): 2.32 (s, 3H), 2.51 (t, J=4.8 Hz, 4H), 3.42 (br s, 4H), 3.86 (s, 3H), 5.75 (dd, J=9.2, 2.4 Hz, 1H), 5.95 (br s, 1H), 6.31-6.39 (m, 2H), 7.12 (d, J=5.6 Hz, 1H), 7.31 (t, J=8.0 Hz, 1H), 7.55-7.75 (m, 2H), 7.84 (d, J=8.8 Hz, 1H), 8.18 (s, 1H). $^{13}$C NMR (100 MHz, DMSO) δ (ppm): 45.3, 46.2, 53.1, 54.7, 98.0, 112.0, 116.1, 116.5, 120.6, 125.3 (q, J=268 Hz), 127.3, 128.8, 129.3, 132.3, 138.9, 139.4, 154.6, 156.2, 157.5, 161.9, 163.5, 172.0. ESI-MS m/z 529.6 (M+H)$^+$.

For ES-074:

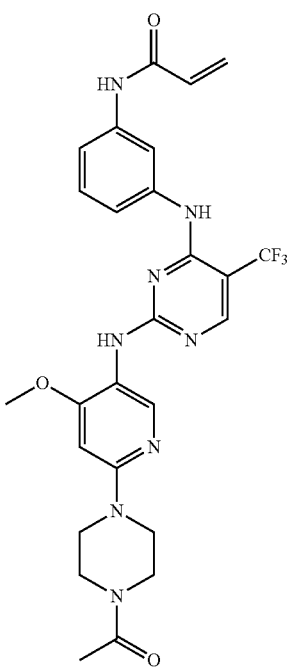
ES-074

The synthesis was conducted according to method B, yield 75%. $^1$H NMR (400 MHz, CD$_3$OD) δ (ppm): 2.14 (s, 3H), 3.42-3.57 (m, 4H), 3.60-3.72 (m, 4H), 3.82 (s, 3H), 5.75 (dd, J=9.6, 1.8 Hz, 1H), 6.26-6.46 (m, 3H), 7.11-7.25 (m, 2H), 7.46 (d, J=7.8 Hz, 1H), 7.74 (br s, 1H), 8.18 (s, 1H), 8.19 (s, 1H). ESI-MS: m/z 557.5 (M+H)$^+$.

For ES-075:

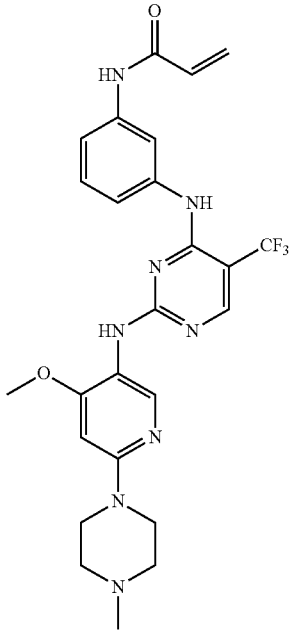
ES-075

The synthesis was conducted according to method G, yield 60%. $^1$H NMR (500 MHz, CD$_3$OD) δ (ppm): 2.57 (s, 3H), 2.77-2.93 (m, 4H), 3.55-3.68 (m, 4H), 3.85 (s, 3H), 5.77 (dd, J=9.9, 1.0 Hz, 1H), 6.32-6.48 (m, 3H), 7.14-7.30 (m, 2H), 7.48 (d, J=8.2 Hz, 1H), 7.76 (br s, 1H), 8.21 (s, 1H), 8.23 (s, 1H). ESI-MS: m/z 529.3(M+H)$^+$.

For ES-123:

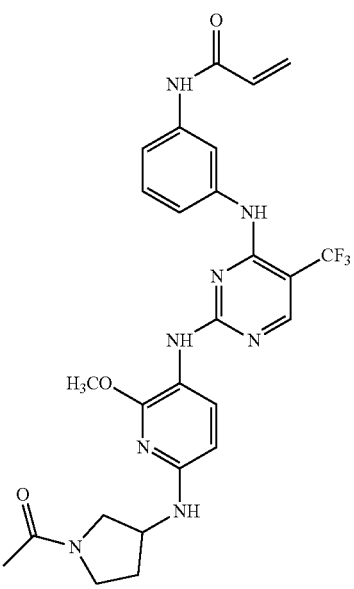
ES-123

The synthesis was conducted according to method B, yield 65%. $^1$H NMR (400 MHz, CD$_3$OD) δ (ppm): 1.87-1.99 (m, 1H), 2.03 (d, J=14.9 Hz, 3H), 2.14-2.31 (m, 1H), 3.35-3.77 (m, 4H), 3.85 (d, J=3.1 Hz, 3H), 4.27-4.40 (m, 1H), 5.67-5.87 (m, 2H), 6.29-6.44 (m, 2H), 7.17 (br s, 1H), 7.27 (t, J=8.0 Hz, 1H), 7.45-7.87 (m, 3H), 8.15 (s, 1H). ESI-MS: m/z 557.6 (M+H)$^+$.

For ES-124:

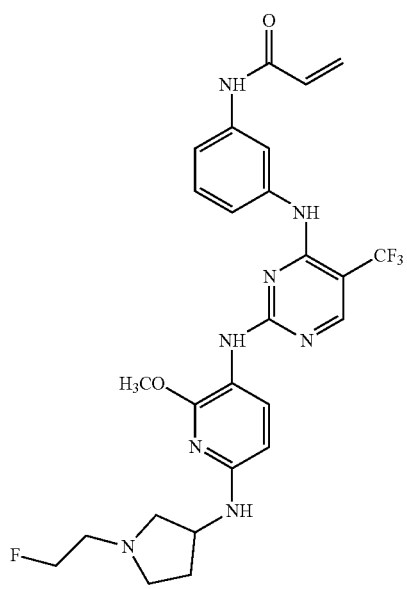

The synthesis was conducted according to method E, yield 40%. $^1$H NMR (400 MHz, CD$_3$OD) δ (ppm): 1.73-1.82 (m, 1H), 2.29-2.38 (m, 1H), 2.72-3.06 (m, 5H), 3.16-3.24 (m, 1H), 3.84 (s, 3H), 4.27-4.38 (m, 1H), 4.54 (t, J=4.8 Hz, 1H), 4.66 (t, J=4.7 Hz, 1H), 5.69-5.80 (m, 2H), 6.29-6.46 (m, 2H), 7.18 (br s, 1H), 7.27 (t, J=7.9 Hz, 1H), 7.47-7.76 (m, 3H), 8.16 (s, 1H). ESI-MS: m/z 561.5 (M+H)$^+$.

For ES-125:

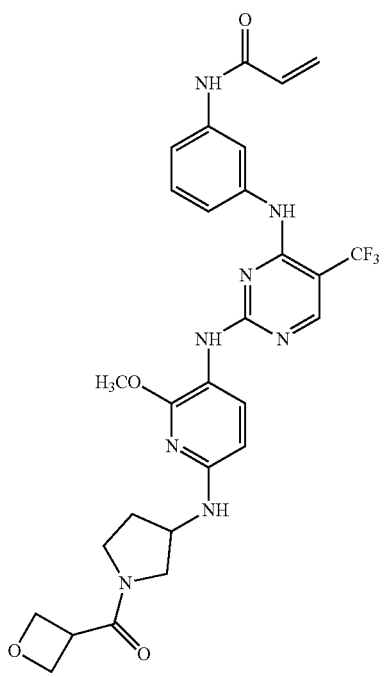

The synthesis was conducted according to method D, yield 60%. $^1$H NMR (400 MHz, CD$_3$OD) δ (ppm): 1.87-2.03 (m, 1H), 2.12-2.27 (m, 1H), 3.34-3.80 (m, 4H), 3.84 (s, 3H), 4.00-4.18 (m, 1H), 4.23-4.40 (m, 1H), 4.68-4.84 (m, 4H), 5.63-5.97 (m, 2H), 6.29-6.46 (m, 2H), 7.17 (brs, 1H), 7.27 (t, J=7.9 Hz, 1H), 7.46-7.76 (m, 3H), 8.16 (s, 1H). ESI-MS: m/z 599.5 (M+H)$^+$.

For ES-130:

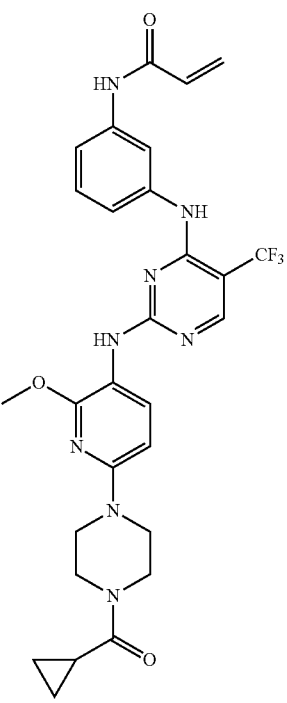

The synthesis was conducted according to method A, yield 70%. $^1$H NMR (500 MHz, CDCl$_3$) δ (ppm): 0.79-0.82 (m, 2H), 1.01-1.03 (m, 2H), 1.75-1.80 (m, 1H), 3.41 (br s, 2H), 3.52 (br s, 2H), 3.75 (br s, 2H), 3.79 (br s, 2H), 3.94 (s, 3H), 5.77 (d, J=10.5 Hz, 1H), 6.01 (br s, 1H), 6.21-6.26 (m, 1H), 6.41-6.47 (m, 1H), 7.21 (br s, 1H), 7.33 (t, J=8.5 Hz, 1H), 7.45-7.90 (m, 2H), 8.15 (br s, 1H), 8.28 (s, 1H). $^{13}$C NMR (100 MHz, CDCl$_3$) δ (ppm): 7.51, 11.0, 41.7, 45.1, 45.7, 45.9, 53.2, 97.7, 113.7, 115.1, 116.5, 119.0, 124.8 (q, J=268 Hz), 127.9, 129.3, 131.0, 138.0, 138.5, 152.6, 153.0, 155.7, 157.4, 160.6, 163.6, 172.2. ESI-MS m/z 583.5 (M+H)$^+$.

For ES-131:

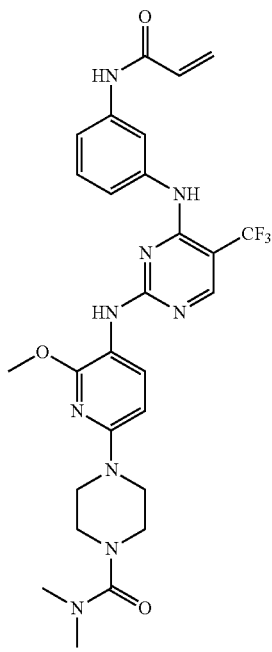

ES-131

The synthesis was conducted according to method A, yield 75%. $^1$H NMR (400 MHz, CDCl$_3$) δ (ppm): 2.85 (s, 6H), 3.25-3.35 (m, 4H), 3.35-3.45 (m, 4H), 3.90 (s, 3H), 5.74 (d, J=10.8 Hz, 1H), 5.97 (br s, 1H), 6.15-6.25 (m, 1H), 6.38-6.45 (m, 1H), 6.84 (br s, 1H), 7.17 (br s, 1H), 7.27-7.40 (m, 2H), 7.45-7.85 (m, 3H), 8.10 (br s, 1H), 8.25 (s, 1H). ESI-MS m/z 586.5 (M+H)$^+$.

For ES-132:

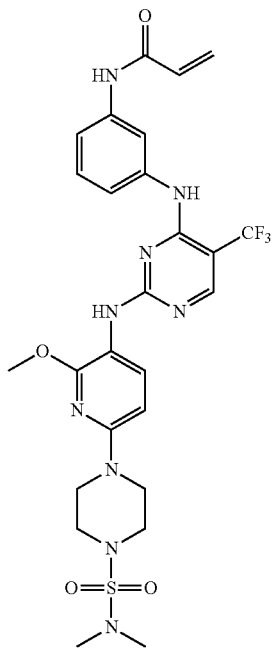

ES-132

The synthesis was conducted according to method C, yield 65%. $^1$H NMR (500 MHz, CDCl$_3$) δ (ppm): 2.87 (s, 6H), 3.30-3.38 (m, 4H), 3.46-3.54 (m, 4H), 3.94 (s, 3H), 5.80 (d, J=10.5 Hz, 1H), 6.00 (br s, 1H), 6.17-6.30 (m, 1H), 6.42-6.48 (m, 1H), 6.86 (br s, 1H), 7.24 (br s, 1H), 7.30-7.40 (m, 3H), 7.45-7.90 (m, 2H), 8.16 (br s, 1H), 8.29 (s, 1H). ESI-MS m/z 622.6 (M+H)$^+$.

For ES-133:

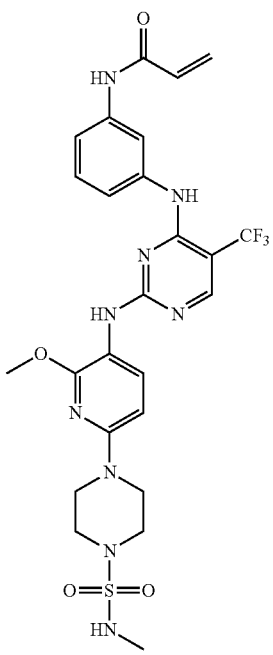

ES-133

The synthesis was conducted according to method C, yield 60%. $^1$H NMR (400 MHz, CDCl$_3$) δ (ppm): 2.78 (d, J=7.2 Hz, 3H), 3.30-3.36 (m, 4H), 3.46-3.54 (m, 4H), 3.94 (s, 3H), 5.80 (d, J=10.5 Hz, 1H), 6.00 (br s, 1H), 6.17-6.30 (m, 1H), 6.42-6.48 (m, 1H), 6.86 (br s, 1H), 7.24 (br s, 1H), 7.30-7.40 (m, 3H), 7.45-7.90 (m, 2H), 8.16 (br s, 1H), 8.29 (s, 1H). ESI-MS m/z 608.6 (M+H)$^+$.

For ES-134:

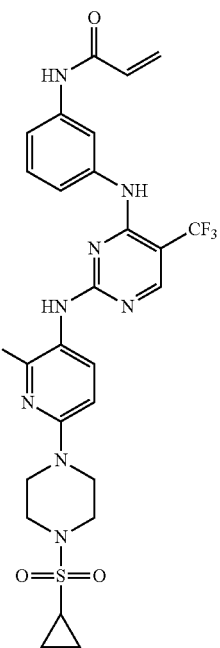

ES-134

The synthesis was conducted according to method C, yield 45%. $^1$H NMR (500 MHz, CDCl$_3$) δ (ppm): 0.99-1.03 (m, 2H), 1.19-1.22 (m, 2H), 2.27-2.30 (m, 1H), 3.40-3.41 (m, 4H), 3.50-3.60 (m, 4H), 3.94 (s, 3H), 5.80 (d, J=10.5 Hz, 1H), 6.05 (br s, 1H), 6.18-6.30 (m, 1H), 6.44-6.47 (m, 1H), 6.86 (br s, 1H), 7.23 (br s, 1H), 7.30-7.40 (m, 3H), 7.45-7.90 (m, 2H), 8.17 (br s, 1H), 8.29 (s, 1H). ESI-MS m/z 619.3 (M+H)⁺.

For ES-135:

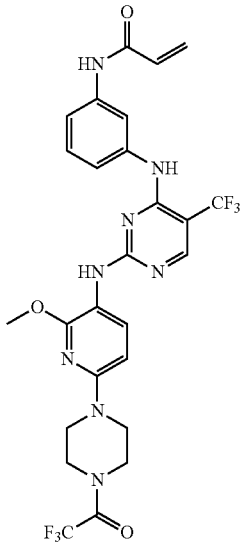

ES-135

The synthesis was conducted according to method B, yield 75%. ¹H NMR (400 MHz, CDCl₃) δ (ppm): 3.45-3.55 (m, 4H), 3.68-3.80 (m, 4H), 3.94 (s, 3H), 5.80 (d, J=10.5 Hz, 1H), 6.05 (br s, 1H), 6.18-6.30 (m, 1H), 6.41-6.42 (m, 1H), 6.86 (br s, 1H), 7.19 (br s, 1H), 7.30-7.40 (m, 3H), 7.45-7.90 (m, 2H), 8.17 (br s, 1H), 8.29 (s, 1H). ESI-MS m/z 611.6 (M+H)⁺.

For ES-136:

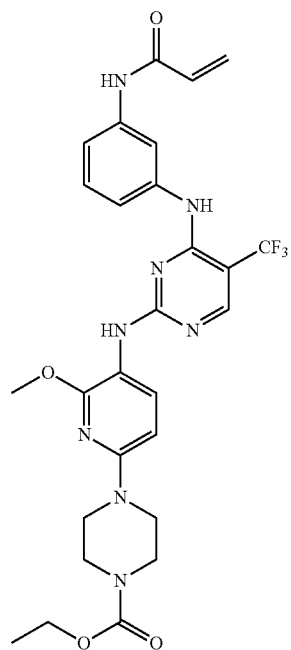

ES-136

The synthesis was conducted according to method A, yield 80%. ¹H NMR (500 MHz, CDCl₃) δ (ppm): 1.30 (t, J=7.0 Hz, 3H), 3.40-3.50 (m, 4H), 3.55-3.65 (m, 4H), 3.95 (s, 3H), 4.18 (q, J=7.0 Hz, 2H), 5.80 (d, J=10.5 Hz, 1H), 5.95-6.30 (m, 2H), 6.44-6.47 (m, 1H), 6.86 (br s, 1H), 7.22 (br s, 1H), 7.31-7.40 (m, 3H), 7.45-8.00 (m, 2H), 8.15 (br s, 1H), 8.30 (s, 1H). ESI-MS m/z 587.5 (M+H)⁺.

For ES-137:

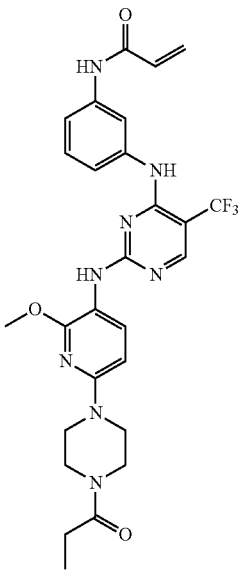

ES-137

The synthesis was conducted according to method A, yield 85%. ¹H NMR (500 MHz, CDCl₃) δ (ppm): 1.19 (t, J=7.0 Hz, 3H), 2.40 (q, J=7.0 Hz, 2H), 3.41 (br s, 2H), 3.47 (br s, 2H), 3.58 (br s, 2H), 3.74 (br s, 2H), 3.95 (s, 3H), 5.80 (d, J=10.5 Hz, 1H), 5.95-6.30 (m, 2H), 6.44-6.47 (m, 1H), 6.87 (br s, 1H), 7.22 (br s, 1H), 7.30-7.40 (m, 3H), 7.45-8.00 (m, 2H), 8.15 (br s, 1H), 8.29 (s, 1H). ¹³C NMR (100 MHz, CDCl₃) δ (ppm): 8.4, 28.7, 40.3, 44.2, 44.7, 45.0, 52.2, 97.1, 112.7, 116.0, 118.0, 123.0, 123.7, 125.1 (q, J=268 Hz), 126.6, 128.1, 130.2, 136.9, 137.9, 146.5, 152.0, 154.3, 156.7, 159.5, 163.6, 172.4. ESI-MS m/z 571.6 (M+H)⁺.

For ES-138:

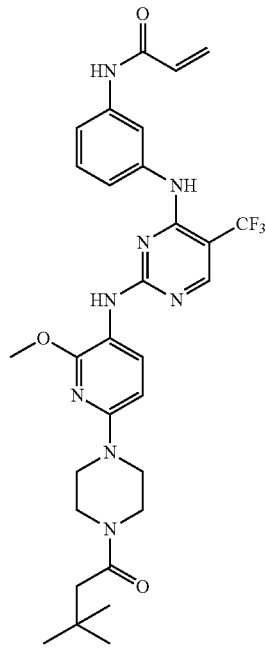

ES-138

The synthesis was conducted according to method A, yield 70%. ¹H NMR (500 MHz, CDCl₃) δ (ppm): 1.08 (s, 9H), 2.32 (s, 2H), 3.41 (br s, 2H), 3.46 (br s, 2H), 3.63 (br s, 2H), 3.76 (br s, 2H), 3.95 (s, 3H), 5.79 (d, J=10.5 Hz, 1H), 5.95-6.30 (m, 2H), 6.44-6.47 (m, 1H), 6.86 (br s, 1H), 7.22 (br s, 1H), 7.30-7.40 (m, 3H), 7.45-8.00 (m, 2H), 8.15 (br s, 1H), 8.29 (s, 1H). ESI-MS m/z 613.7 (M+H)⁺.

For ES-139:

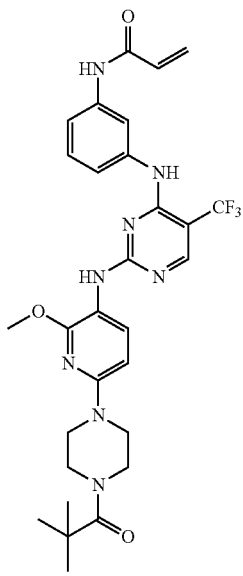

ES-139

The synthesis was conducted according to method A, yield 50%. $^1$H NMR (500 MHz, CDCl$_3$) δ (ppm): 1.33 (s, 9H), 3.43 (br s, 4H), 3.75-3.78 (m, 4H), 3.95 (s, 3H), 5.79 (d, J=10.5 Hz, 1H), 6.05 (br s, 1H), 6.18-6.28 (m, 1H), 6.43-6.48 (m, 1H), 6.86 (br s, 1H), 7.22 (br s, 1H), 7.30-7.40 (m, 2H), 7.45-7.90 (m, 2H), 8.17 (br s, 1H), 8.30 (s, 1H). ESI-MS m/z 599.6 (M+H)$^+$.

For ES-140:

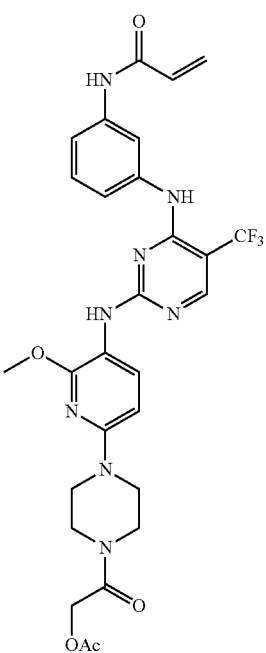

ES-140

The synthesis was conducted according to method A, yield 70%. $^1$H NMR (500 MHz, CDCl$_3$) δ (ppm): 2.21 (s, 3H), 3.44 (br s, 2H), 3.51 (br s, 4H), 3.74 (br s, 2H), 3.94 (s, 3H), 4.78 (s, 2H), 5.80 (d, J=10.5 Hz, 1H), 6.05 (br s, 1H), 6.18-6.28 (m, 1H), 6.43-6.48 (m, 1H), 6.87 (br s, 1H), 7.22 (br s, 1H), 7.30-7.40 (m, 3H), 7.45-7.90 (m, 2H), 8.18 (br s, 1H), 8.30 (s, 1H). ESI-MS m/z 615.5 (M+H)$^+$.

For ES-141:

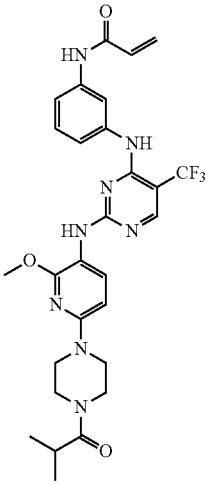

ES-141

The synthesis was conducted according to method A, yield 50%. $^1$H NMR (500 MHz, CDCl$_3$) δ (ppm): 1.17 (d, J=7.0 Hz, 6H), 2.80-2.90 (m, 1H), 3.41 (br s, 2H), 3.48 (br s, 2H), 3.64 (br s, 2H), 3.75 (br s, 2H), 3.95 (s, 3H), 5.79 (d, J=10.5 Hz, 1H), 6.05 (br s, 1H), 6.18-6.28 (m, 1H), 6.43-6.48 (m, 1H), 6.87 (br s, 1H), 7.22 (br s, 1H), 7.30-7.40 (m, 2H), 7.45-7.90 (m, 2H), 8.18 (br s, 1H), 8.29 (s, 1H). ESI-MS m/z 619.6 (M+H)$^+$.

For ES-142:

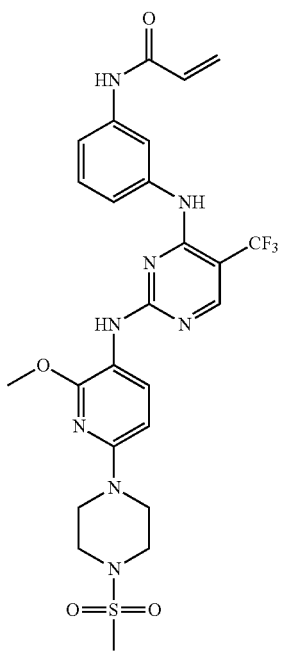

ES-142

The synthesis was conducted according to method C, yield 50%. $^1$H NMR (500 MHz, CDCl$_3$) δ (ppm): 2.82 (s, 3H), 3.32-3.34 (m, 4H), 3.57 (br s, 4H), 3.95 (s, 3H), 5.81

(d, J=10.0 Hz, 1H), 6.05 (br s, 1H), 6.18-6.28 (m, 1H), 6.44-6.48 (m, 1H), 6.87 (br s, 1H), 7.22 (br s, 1H), 7.30-7.40 (m, 2H), 7.45-7.90 (m, 2H), 8.18 (br s, 1H), 8.30 (s, 1H).

For ES-143:

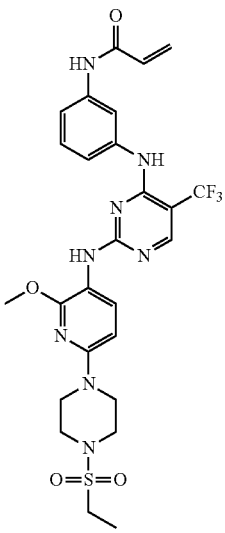

ES-143

The synthesis was conducted according to method C, yield 55%. $^1$H NMR (400 MHz, CDCl$_3$) δ (ppm): 1.38 (t, J=7.6 Hz, 3H), 2.96 (q, J=7.2 Hz, 2H), 3.35-3.38 (m, 4H), 3.51 (br s, 4H), 3.91 (br s, 3H), 5.78 (d, J=10.0 Hz, 1H), 6.00 (br s, 1H), 6.18-6.28 (m, 1H), 6.41-6.45 (m, 1H), 6.84 (br s, 1H), 7.22 (br s, 1H), 7.30-7.40 (m, 2H), 7.45-7.90 (m, 2H), 8.16 (br s, 1H), 8.27 (s, 1H). ESI-MS m/z 607.4 (M+H)$^+$.

For ES-144:

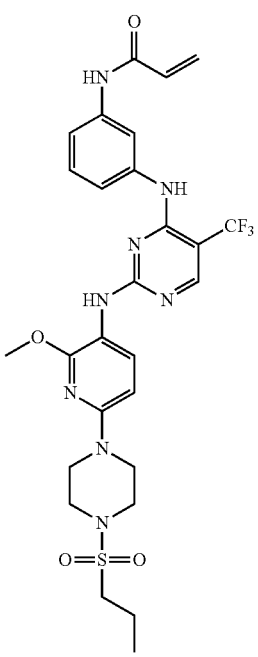

ES-144

The synthesis was conducted according to method C, yield 50%. $^1$H NMR (400 MHz, CDCl$_3$) δ (ppm): 1.05 (t, J=7.6 Hz, 3H), 1.80-1.90 (m, 2H), 2.86-2.90 (m, 2H), 3.34-3.36 (m, 4H), 3.51 (br s, 4H), 3.92 (s, 3H), 5.78 (d, J=10.0 Hz, 1H), 6.00 (br s, 1H), 6.15-6.25 (m, 1H), 6.41-6.45 (m, 1H), 6.84 (br s, 1H), 7.22 (br s, 1H), 7.30-7.40 (m, 2H), 7.45-7.90 (m, 2H), 8.15 (br s, 1H), 8.27 (s, 1H). ESI-MS m/z 621.6 (M+H)$^+$.

For ES-145:

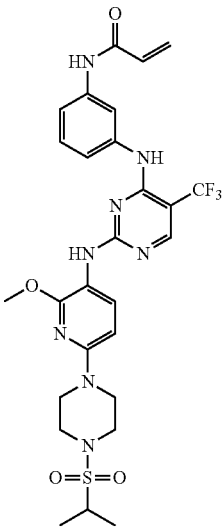

ES-145

The synthesis was conducted according to method C, yield 40%. $^1$H NMR (400 MHz, CDCl$_3$) δ (ppm): 1.35 (d, J=6.4 Hz, 6H), 3.60-3.70 (m, 1H), 3.43-3.47 (m, 8H), 3.92 (s, 3H), 5.78 (d, J=10.0 Hz, 1H), 6.00 (br s, 1H), 6.15-6.25 (m, 1H), 6.41-6.45 (m, 1H), 6.84 (br s, 1H), 7.22 (br s, 1H), 7.30-7.40 (m, 2H), 7.45-7.90 (m, 2H), 8.15 (br s, 1H), 8.27 (s, 1H). ESI-MS m/z 622.3 (M+H)$^+$.

For ES-146:

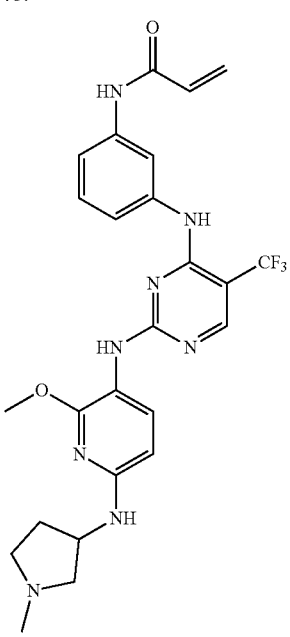

ES-146

The synthesis was conducted according to method E, yield 10%. $^1$H NMR (500 MHz, CD$_3$OD) δ (ppm): 1.99-2.09 (m, 1H), 2.44-2.55 (m, 1H), 2.87 (s, 3H), 3.18-3.30 (m, 2H), 3.43-3.58 (m, 2H), 3.87 (s, 3H), 4.41-4.50 (m, 1H), 5.78 (dd, J=9.9, 2.0 Hz, 1H), 5.87 (br s, 1H), 6.33-6.48 (m, 2H), 7.19 (br s, 1H), 7.31 (t, J=8.0 Hz, 1H), 7.46-7.67 (m, 2H), 7.69 (d, J=10.0 Hz, 1H), 8.19 (s, 1H). ESI-MS: m/z 529.6 (M+H)$^+$.

For ES-147:

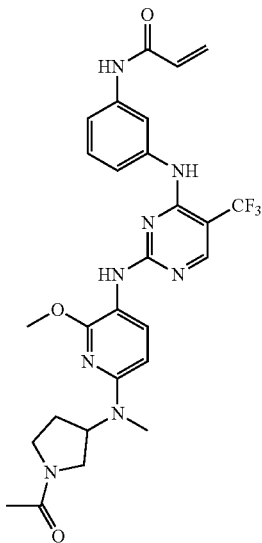
ES-147

The synthesis was conducted according to method B, yield 75%. $^1$H NMR (500 MHz, CD$_3$OD) δ (ppm): 2.07 (d, J=8.4 Hz, 3H), 2.09-2.27 (m, 2H), 2.87 (d, J=10.4 Hz, 3H), 3.36-3.63 (m, 2H), 3.66-3.77 (m, 2H), 3.89 (d, J=3.8 Hz, 3H), 5.11-5.30 (m, 1H), 5.77 (dd, J=9.7, 2.2 Hz, 1H), 5.88 (br s, 1H), 6.31-6.47 (m, 2H), 7.15 (br s, 1H), 7.31 (t, J=8.1 Hz, 1H), 7.54-7.78 (m, 2H), 7.82 (dd, J=8.5, 6.7 Hz, 1H), 8.20 (s, 1H). ESI-MS: m/z 571.6 (M+H)$^+$.

For ES-148:

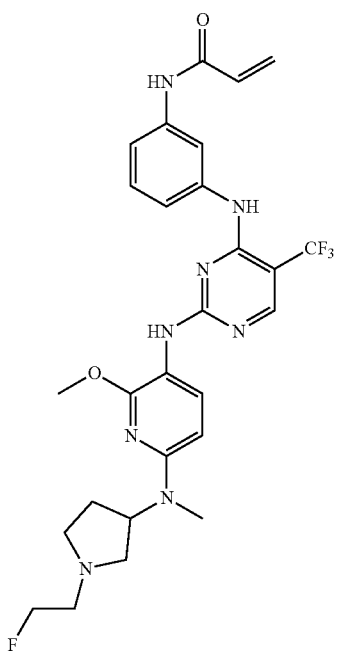
ES-148

The synthesis was conducted according to method E, yield 35%. $^1$H NMR (500 MHz, DMSO) δ (ppm): 1.82-1.90 (m, 1H), 2.10-2.20 (m, 1H), 2.63-3.02 (m, 9H), 3.89 (s, 3H), 4.54 (t, J=5.0, 1H), 4.64 (t, J=5.0, 1H), 5.28-5.39 (m, 1H), 5.77 (dd, J=9.7, 2.2 Hz, 1H), 5.82 (br s, 1H), 6.32-6.46 (m, 2H), 7.16 (br s, 1H), 7.30 (t, J=8.0 Hz, 1H), 7.52-7.74 (m, 2H), 7.77 (d, J=8.5 Hz, 1H), 8.19 (s, 1H). $^{13}$C NMR (100 MHz, CD$_3$OD) δ (ppm): 28.1, 30.3, 52.5, 53.7, 55.0, 55.2, 57.0, 82.8 (d, J=163.4 Hz), 96.5, 109.9, 115.5, 115.9, 120.0, 124.9 (q, J=268.3 Hz), 126.8, 128.3, 131.9, 135.0, 138.5, 138.9, 154.0, 155.7, 157.0, 161.4, 163.1. ESI-MS: m/z 575.5 (M+H)$^+$.

For ES-149:

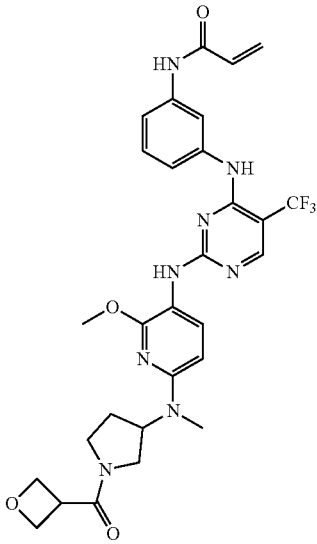
ES-149

The synthesis was conducted according to method D, yield 60%. $^1$H NMR (500 MHz, CD$_3$OD) δ: 2.08-2.22 (m, 2H), 2.84-2.88 (m, 3H), 3.37-3.77 (m, 4H), 3.88 (d, J=2.7 Hz, 3H), 4.09-4.21 (m, 1H), 4.79-4.84 (m, 2H), 4.86-4.90 (m, 2H), 5.12-5.25 (m, 1H), 5.77 (dd, J=9.7, 2.1 Hz, 1H), 5.88 (br s, 1H), 6.32-6.46 (m, 2H), 7.15 (br s, 1H), 7.31 (t, J=8.1 Hz, 1H), 7.55-7.77 (m, 2H), 7.81 (dd, J=8.6, 4.5 Hz, 1H), 8.20 (s, 1H). ESI-MS: m/z 613.4 (M+H)$^+$.

For ES-150:

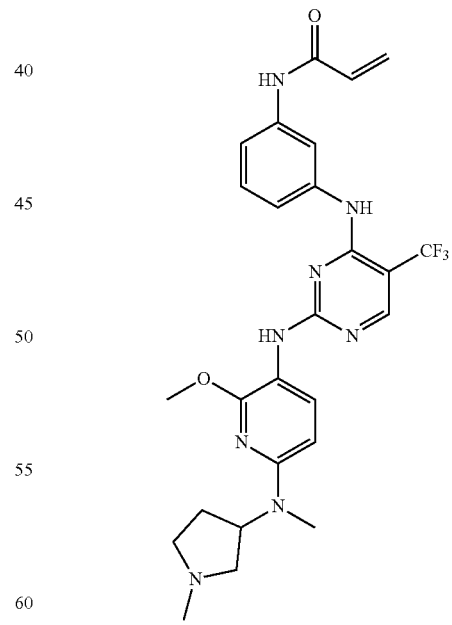
ES-150

The synthesis was conducted according to method F, yield 45%. $^1$H NMR (500 MHz, CD$_3$OD) δ (ppm): 2.03-2.12 (m, 1H), 2.20-2.31 (m, 1H), 2.72 (s, 3H), 2.89 (s, 3H), 2.95-3.02 (m, 1H), 3.06-3.25 (m, 3H), 3.90 (s, 3H), 5.40-5.48 (m, 1H), 5.78 (dd, J=9.8, 2.1 Hz, 1H), 5.88 (br s, 1H), 6.32-6.47 (m, 2H), 7.16 (br s, 1H), 7.31 (t, J=8.1 Hz, 1H), 7.52-7.76 (m, 2H), 7.82 (d, J=8.5 Hz, 1H), 8.20 (s, 1H). ESI-MS: m/z 543.5 (M+H)+.

For ES-151:

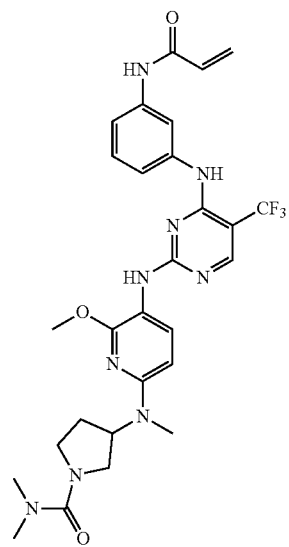

The synthesis was conducted according to method A, yield 70%. ¹H NMR (500 MHz, CD₃OD) δ (ppm): 2.00-2.11 (m, 2H), 2.87 (s, 9H), 3.35-3.43 (m, 1H), 3.46-3.59 (m, 3H), 3.88 (s, 3H), 5.02-5.13 (m, 1H), 5.77 (dd, J=9.7, 2.2 Hz, 1H), 5.87 (br s, 1H), 6.31-6.46 (m, 2H), 7.15 (br s, 1H), 7.31 (t, J=8.1 Hz, 1H), 7.60 (br s, 1H), 7.71 (brs, 1H), 7.80 (d, J=8.5 Hz, 1H), 8.20 (s, 1H). ESI-MS: m/z 600.5 (M+H)+.

For ES-157:

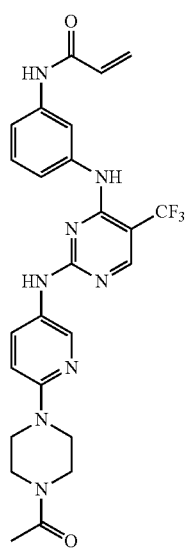

The synthesis was conducted according to method B, yield 80%. ¹H NMR (500 MHz, CD₃OD) δ (ppm): 2.15 (s, 3H), 3.36-3.51 (m, 4H), 3.60-3.72 (m, 4H), 5.78 (dd, J=9.6, 2.2 Hz, 1H), 6.32-6.47 (m, 2H), 6.57 (br s, 1H), 7.15 (br s, 1H), 7.33 (t, J=8.1 Hz, 1H), 7.60 (br s, 1H), 7.74 (br s, 1H), 7.81 (dd, J=9.0, 2.0 Hz, 1H), 8.13 (br s, 1H), 8.23 (s, 1H). ESI-MS: m/z 527.5 (M+H)+.

For ES-158:

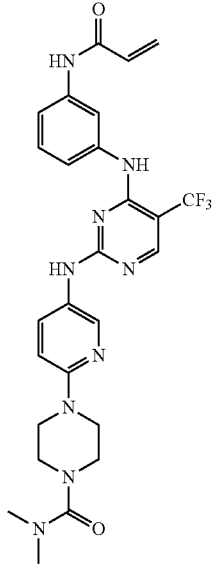

The synthesis was conducted according to method A, yield 80%. ¹H NMR (500 MHz, CD₃OD) δ (ppm): 2.89 (s, 6H), 3.32-3.35 (m, 4H), 3.39-3.44 (m, 4H), 5.78 (dd, J=9.7, 2.1 Hz, 1H), 6.32-6.46 (m, 2H), 6.55 (br s, 1H), 7.16 (brs, 1H), 7.33 (t, J=8.1 Hz, 1H), 7.60 (br s, 1H), 7.75 (br s, 1H), 7.81 (dd, J=9.1, 2.7 Hz, 1H), 8.12 (br s, 1H), 8.23 (s, 1H). ESI-MS: m/z 556.5 (M+H)+.

For ES-160:

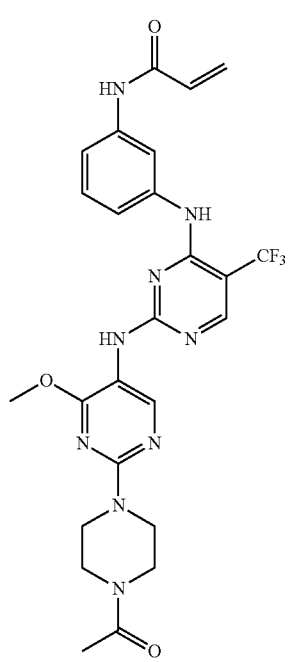

The synthesis was conducted according to method B, yield 85%. ¹H NMR (500 MHz, DMSO) δ (ppm): 2.05 (s, 3H), 3.50 (br s, 4H), 3.66 (br s, 2H), 3.72 (br s, 2H), 3.78 (s, 3H), 5.74 (d, J=9.5 Hz, 1H), 6.21-6.25 (m, 1H), 6.35-6.45 (m, 1H), 7.00-7.40 (m, 3H), 7.65 (br s, 1H), 8.03 (s, 1H), 8.25 (br s, 1H), 8.50 (s, 1H), 10.00 (br s, 1H).

For ES-161:

The synthesis was conducted according to method D, yield 50%. ¹H NMR (400 MHz, CD₃OD) δ (ppm): 3.60-3.80 (m, 8H), 3.90 (s, 3H), 4.20-4.30 (m, 1H), 4.55 (d, J=9.2 Hz, 4H), 5.74 (dd, J=10.0, 2.0 Hz, 1H), 6.28-6.45 (m, 2H), 7.05-7.30 (m, 2H), 7.42 (d, J=7.6 Hz, 1H), 7.60-7.90 (m, 1H), 8.19 (s, 1H). ESI-MS m/z 600.1 (M+H)⁺.

For ES-164:

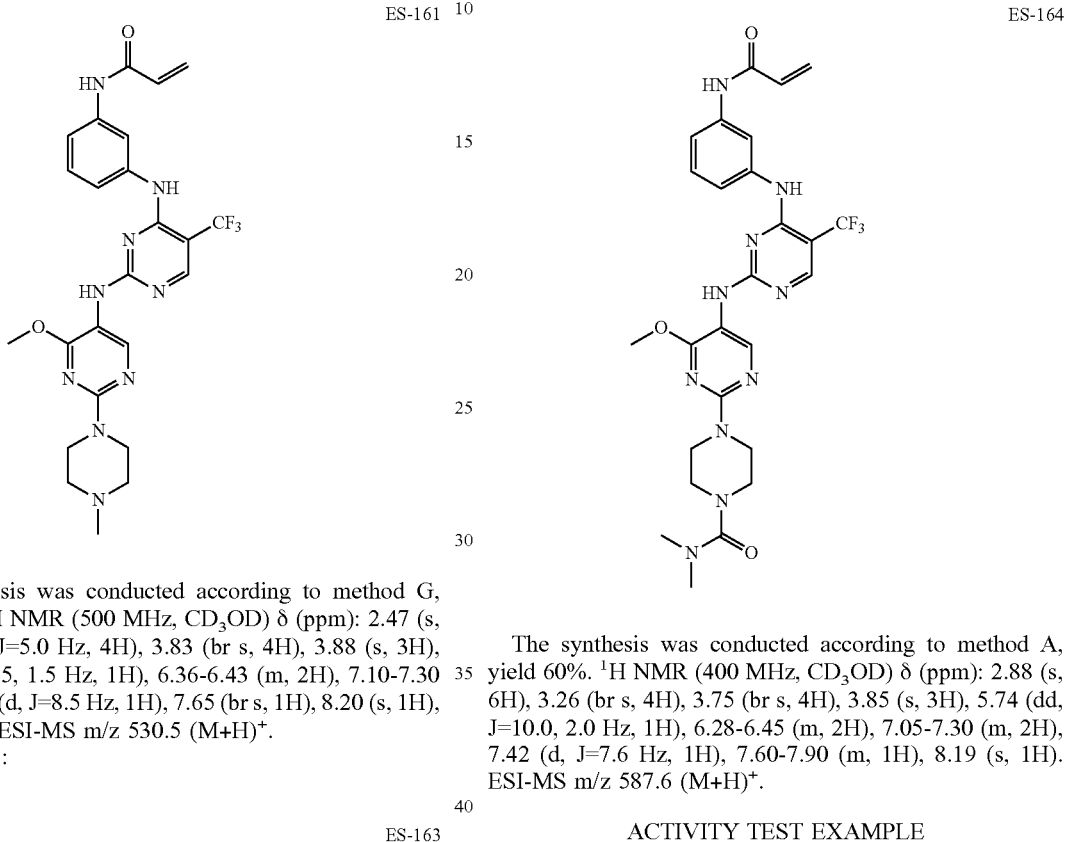

ES-161

ES-164

The synthesis was conducted according to method G, yield 50%. ¹H NMR (500 MHz, CD₃OD) δ (ppm): 2.47 (s, 3H), 2.66 (t, J=5.0 Hz, 4H), 3.83 (br s, 4H), 3.88 (s, 3H), 5.77 (dd, J=9.5, 1.5 Hz, 1H), 6.36-6.43 (m, 2H), 7.10-7.30 (m, 2H), 7.46 (d, J=8.5 Hz, 1H), 7.65 (br s, 1H), 8.20 (s, 1H), 8.23 (s, 1H). ESI-MS m/z 530.5 (M+H)⁺.

For ES-163:

The synthesis was conducted according to method A, yield 60%. ¹H NMR (400 MHz, CD₃OD) δ (ppm): 2.88 (s, 6H), 3.26 (br s, 4H), 3.75 (br s, 4H), 3.85 (s, 3H), 5.74 (dd, J=10.0, 2.0 Hz, 1H), 6.28-6.45 (m, 2H), 7.05-7.30 (m, 2H), 7.42 (d, J=7.6 Hz, 1H), 7.60-7.90 (m, 1H), 8.19 (s, 1H). ESI-MS m/z 587.6 (M+H)⁺.

ACTIVITY TEST EXAMPLE

Test Example 1

The Effect of Compounds to Proliferation of 6 Tumor Cells

Experimental Method:

Human lung cancer cells H1975, H522, human hepatoma cell HepG2, human melanoma cell A375, human epidermal cancer cell A431, and human colon cancer cells COLO205 were cultivated. The cells were collected when they have grown to logarithmic growth phase, and centrifuged at 1000 rpm for 5 min, from which the supernatant was discarded, and the rest was suspended with appropriate amount of medium, and the concentration of cells was adjusted to $2.5\text{-}5.5\times10^4$/ml (once it was $3.0\text{-}5.5\times10^4$/ml). The cell suspension was inoculated into a 96-well cell culture plate with 100 μl per well, and placed in a cell incubator (37° C., 5% CO₂) for 24 hours, and then 100 μl of the drug diluted in the cell culture medium was added to each well of the drug group. Three duplicate wells were set for each drug, and the negative control group was medium containing 0.5% DMSO. After being incubated for 72 hours in the incubator, 20 μl of MTT (5 mg/ml) was added to each well, which was placed under 37° C. for 3 hours. 150 μl of DMSO was added to each well and shaken at 37° C. for 5 mins, and absorbance

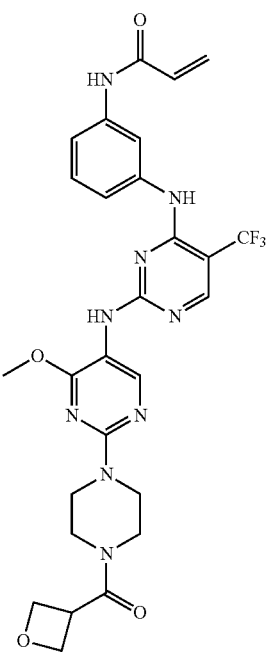

ES-163

(OD) was determined at 492 nm. The Prism Graphpad statistical software was used to calculate IC$_{50}$ values.
The number and structure of each compound are as follows, wherein 1686 is a control compound.
1686
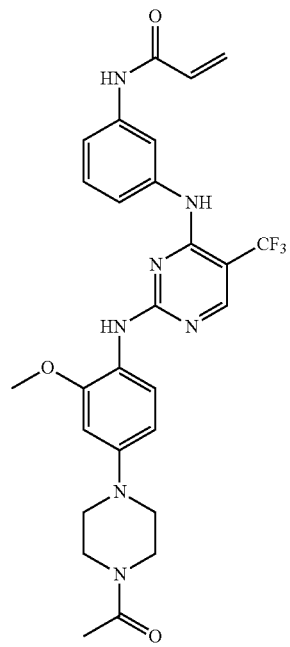
-continued
ES-070
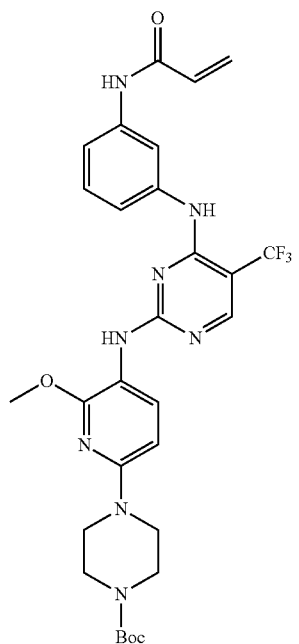
ES-069
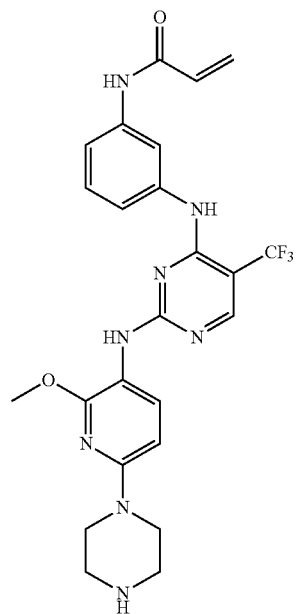
ES-071
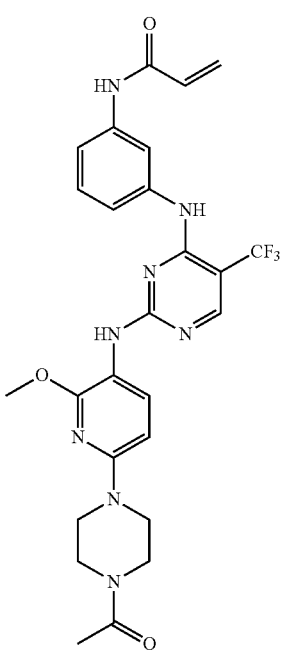

ES-072
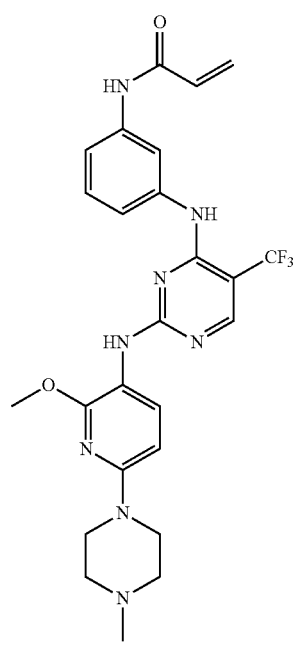
ES-073
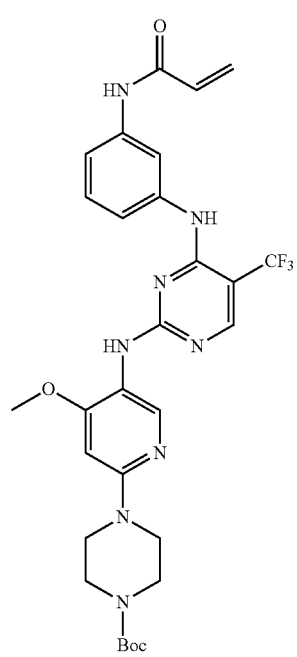
ES-074
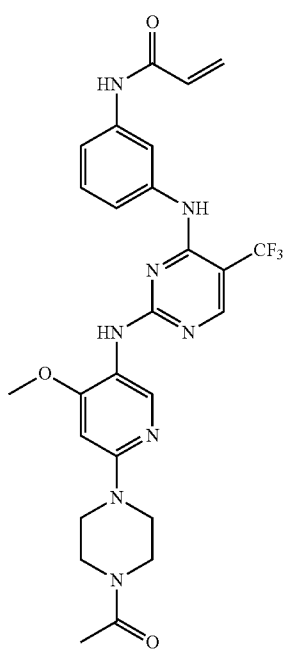
ES-075
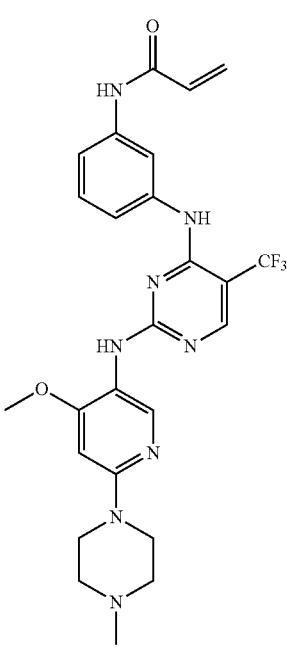

ES-0123
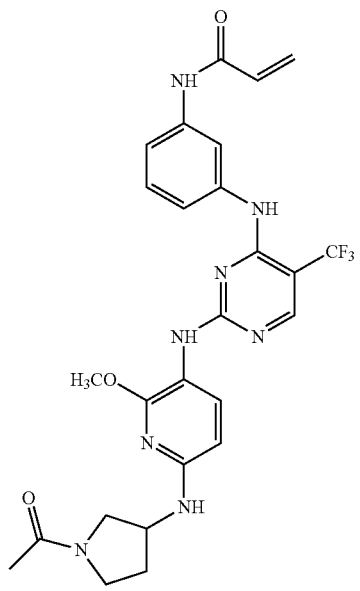
ES-0125
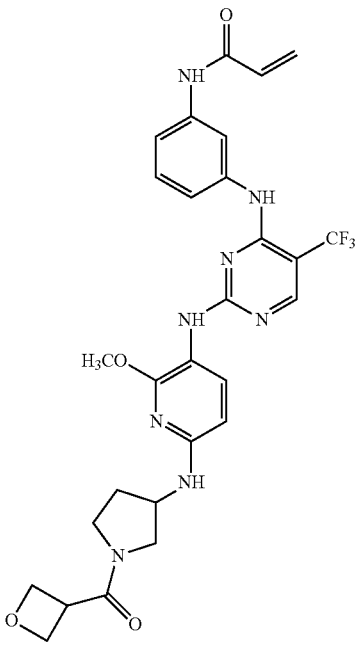
ES-0124
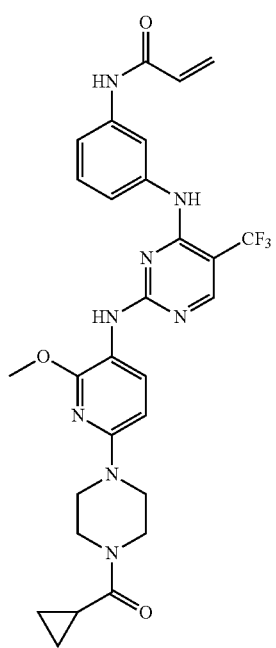
ES-0130

ES-0131
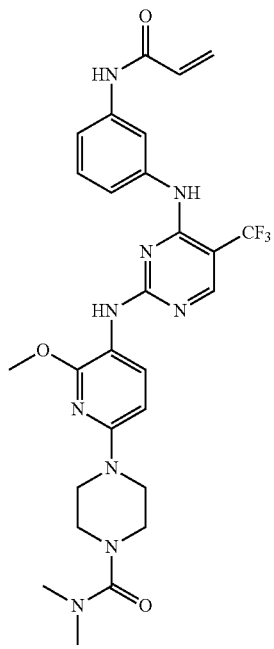
ES-0132
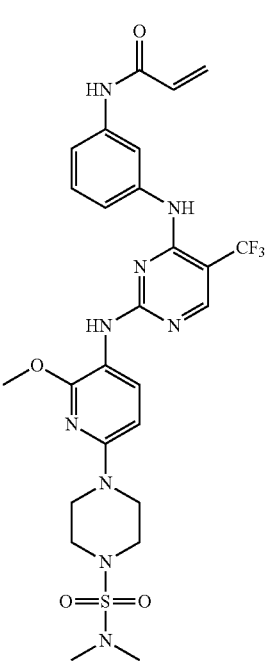
ES-0133
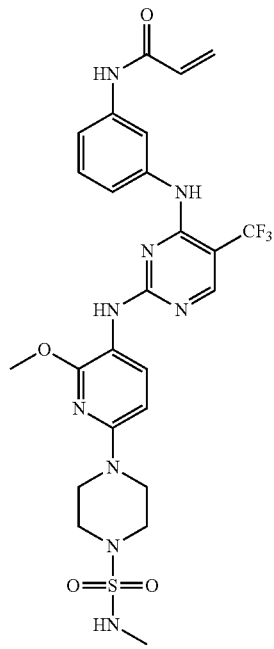
ES-0134
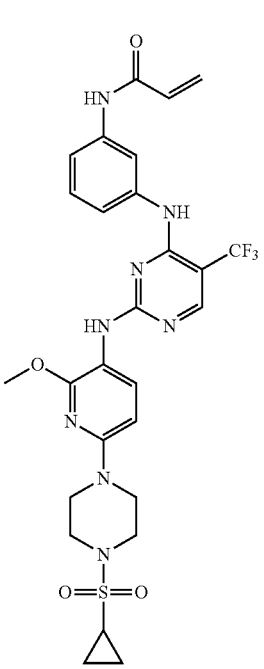

ES-0135
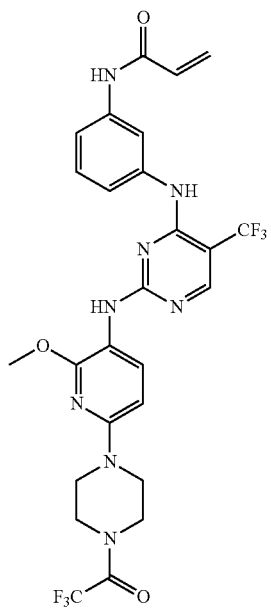
ES-0137
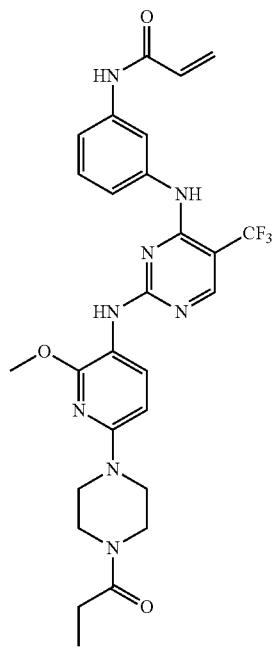
ES-0136
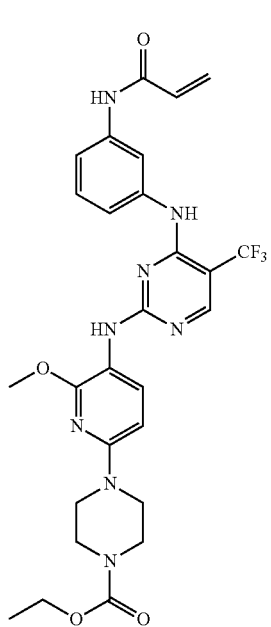
ES-0138
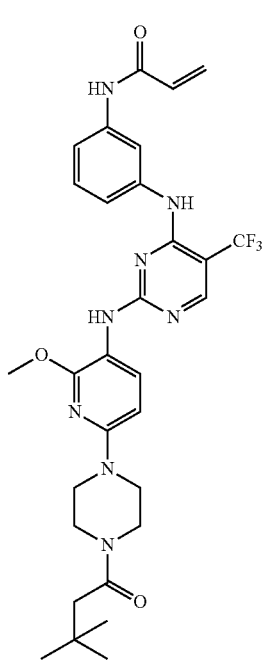

ES-0139
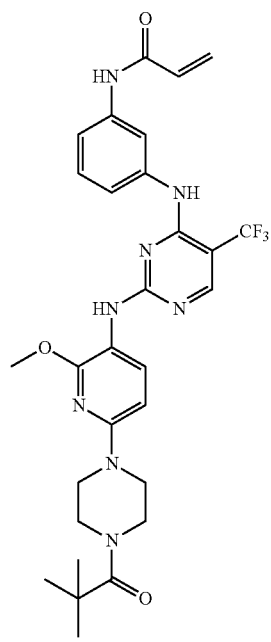
ES-0141
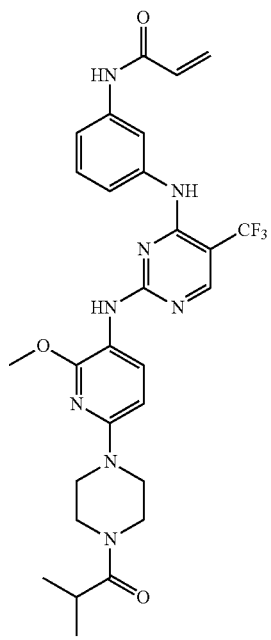
ES-0140
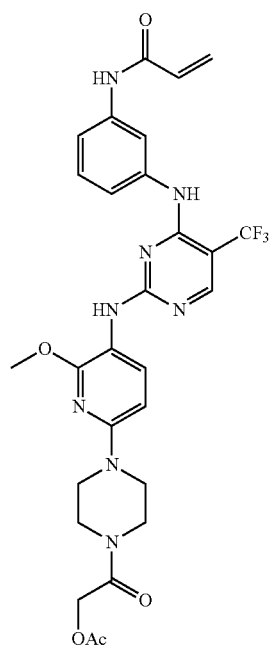
ES-0142
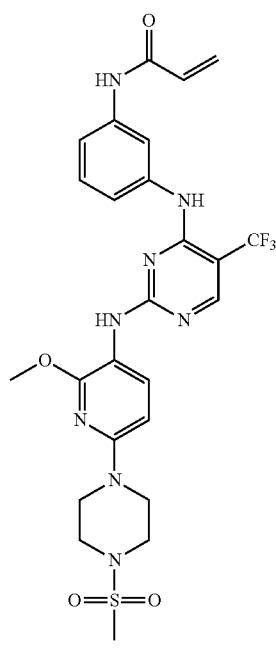

ES-0143
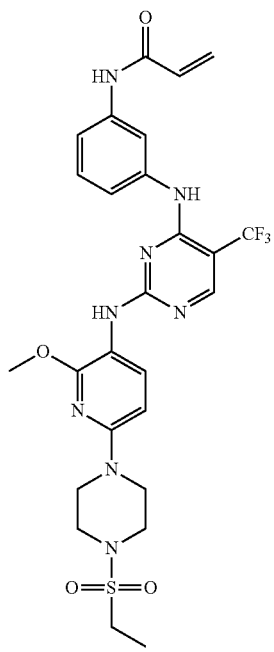
ES-145
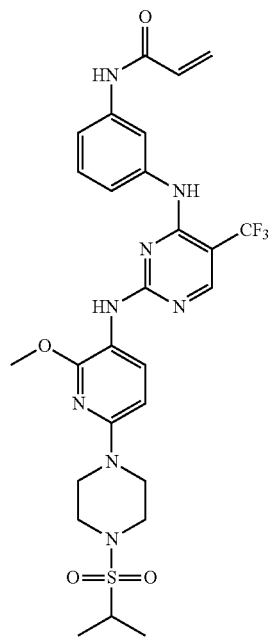
ES-0144
ES-146
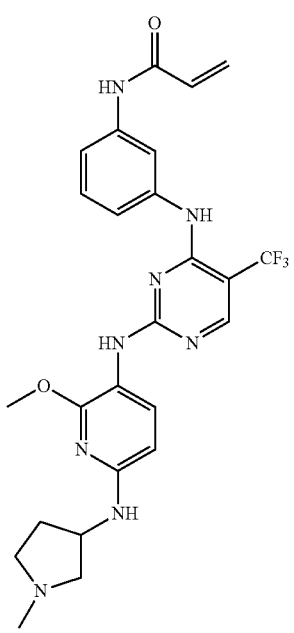

ES-147
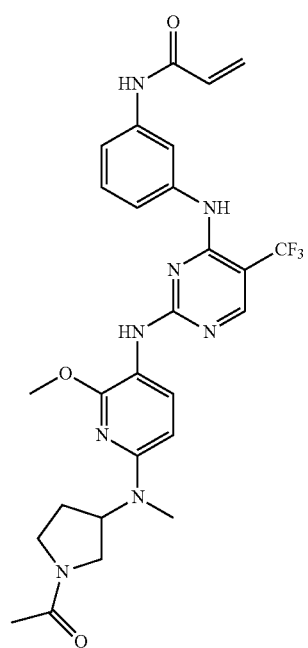
ES-148
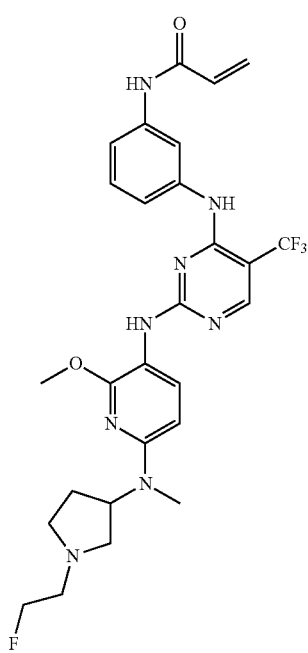
ES-149
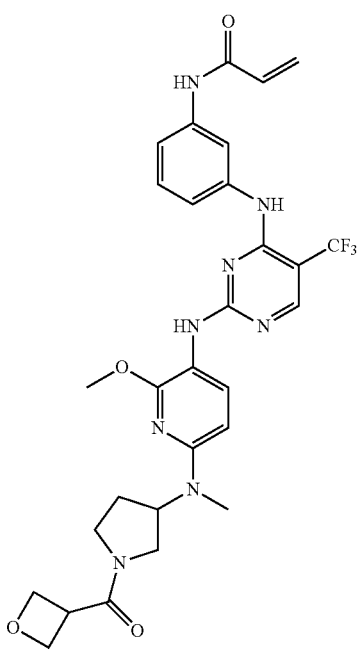
ES-150
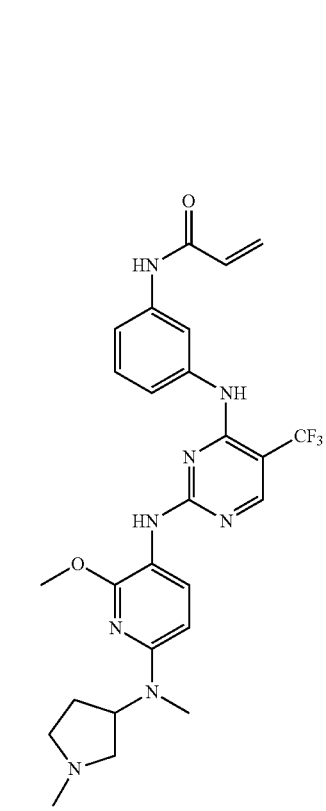

-continued
ES-151
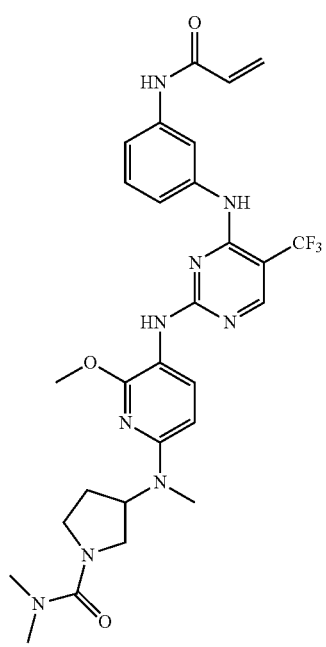
ES-157
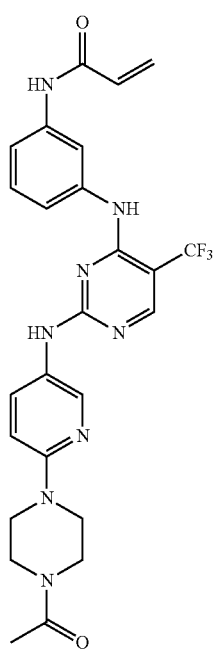
-continued
ES-158
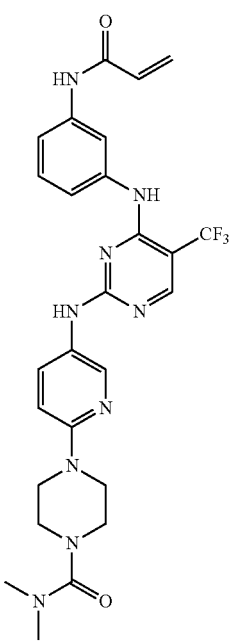
ES-159
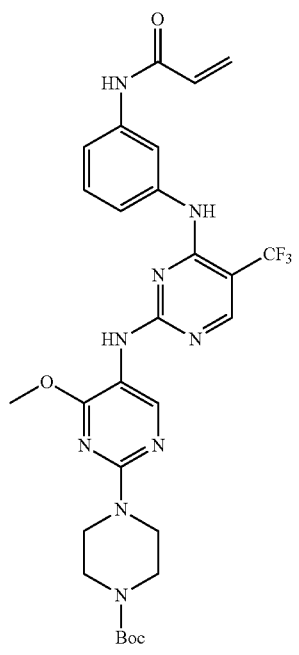

ES-160
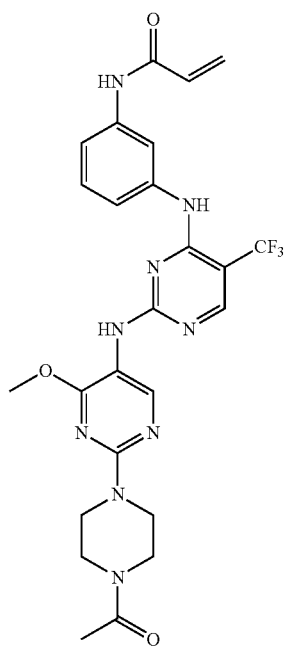
ES-161
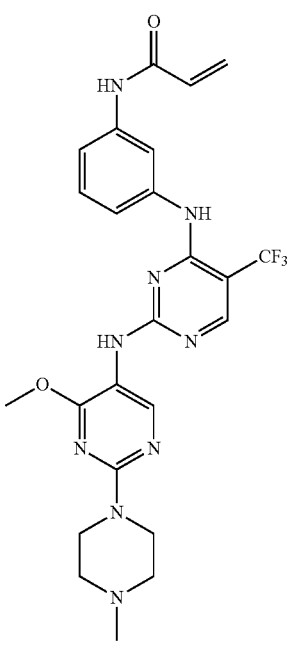
ES-163
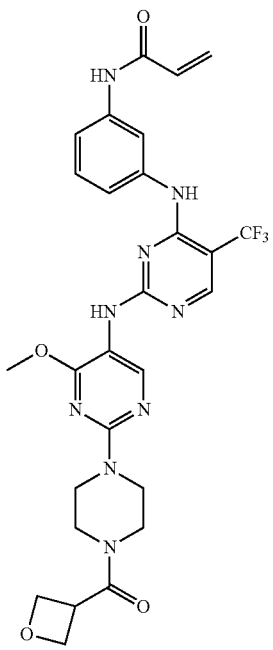
ES-164
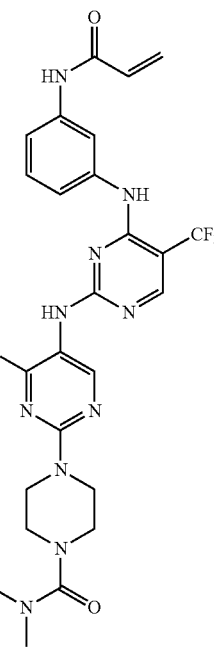
Test Results are Shown in the Following Table:
| Compound No. | IC$_{50}$ (μm) | | | | | |
|---|---|---|---|---|---|---|
| | H1975 | H522 | HepG2 | COLO205 | A375 | A431 |
| 1686 (Control) | 0.0525 | 0.5219 | 1.489 | 4.717 | 3.001 | 1.567 |
| ES-069 | 0.2241 | | 15.83 | | 2.417 | 5.256 |
| ES-070 | 0.111 | | 7.217 | | 4.945 | 1.749 |
| ES-071 | 0.02279 | | 0.968 | | 2.259 | 0.9924 |
| ES-072 | 0.03423 | | 3.312 | | 2.401 | 0.7735 |
| ES-073 | 0.2139 | | 1.95 | | 15.02 | 7.084 |

-continued

| Compound No. | IC$_{50}$ (μm) | | | | | |
|---|---|---|---|---|---|---|
| | H1975 | H522 | HepG2 | COLO205 | A375 | A431 |
| ES-074 | 0.1792 | | 6.875 | | 10.33 | 3.5 |
| ES-075 | 0.03667 | | 3.543 | | 2.745 | 1.266 |
| ES-123 | 0.1505 | 2.694 | 9.199 | 4.623 | 8.937 | 4.624 |
| ES-124 | 0.05567 | 1.252 | 3.733 | 2.206 | 6.257 | 2.092 |
| ES-125 | 0.1488 | 3.963 | 16.78 | 5.559 | 12.18 | 5.045 |
| ES-130 | 0.03557 | 1.768 | 0.7937 | 3.352 | 4.586 | 2.251 |
| ES-131 | 0.0579 | 2.396 | 3.069 | 5.334 | 4.039 | 3.82 |
| ES-132 | 0.2301 | 2.898 | 4.138 | 3.783 | 4.415 | 2.619 |
| ES-133 | 0.4305 | 3.391 | 13.2 | 5.655 | 12.49 | 5.679 |
| ES-134 | 0.0691 | 1.639 | 0.399 | 2.948 | 3.358 | 1.723 |
| ES-135 | 0.11 | 3.247 | 0.329 | 8.868 | 1.496 | 4.429 |
| ES-136 | 0.1752 | 1.588 | 2.046 | 3.591 | 1.039 | 0.7677 |
| ES-137 | 0.02111 | 2.293 | 2.686 | 4.117 | 3.585 | 2.267 |
| ES-138 | 0.2537 | 5.888 | 3.068 | 4.078 | 3.787 | 2.913 |
| ES-139 | 1.645 | 2.71 | 3.861 | 3.604 | 9.473 | 4.544 |
| ES-140 | 0.2698 | 2.277 | 5.869 | 3.16 | 6.455 | 2.081 |
| ES-141 | 0.05518 | 2.341 | 4.052 | 4.255 | 4.505 | 0.7202 |
| ES-142 | 0.08001 | 0.8259 | 1.011 | 2.956 | 4.404 | 1.218 |
| ES-143 | 0.4798 | 1.074 | 0.4008 | 2.147 | 2.022 | >100 |
| ES-144 | 0.1329 | 0.3992 | 0.1007 | 1.46 | 1.507 | 2.181 |
| ES-145 | 0.5425 | 17.98 | 33.3 | 37.65 | 77.85 | 13.53 |
| ES-146 | 0.04598 | 3 | 12.98 | 8.705 | 12.18 | 3.457 |
| ES-147 | 0.4639 | 1.74 | 4.276 | 4.292 | 4.199 | 2.212 |
| ES-148 | 0.03197 | 1.561 | 4.534 | 5 | 5.87 | 2.502 |
| ES-149 | 0.04908 | 3.102 | 5.225 | 5.068 | 6.713 | 3.922 |
| ES-150 | 0.02318 | 1.512 | 3.269 | 5.152 | 6.217 | 2.05 |
| ES-151 | 0.1318 | 3.126 | 4.779 | 6.069 | 4.466 | 6.742 |
| ES-157 | 0.08715 | 0.6546 | 1.378 | 1.795 | 5.455 | 1.806 |
| ES-158 | 0.1072 | 0.735 | 3.423 | 1.932 | 3.76 | 1.071 |
| ES-159 | 0.6486 | 3.133 | 2.227 | 1.86 | 49.86 | 37.04 |
| ES-160 | 0.69 | 3.558 | 5.791 | 5.085 | >100 | 7.206 |
| ES-161 | 0.08684 | 2.748 | 6.244 | 4.144 | 7.863 | 2.324 |
| ES-163 | 0.1682 | 5.114 | 18.88 | 5.486 | 19 | 7.503 |
| ES-164 | 0.07449 | 1.391 | 12.56 | 6.049 | 18.22 | 5.716 |

From the above test results, it can be seen that the compound of the present invention can inhibit the tumor cells in a low inhibitory concentration. Among them, there are differences from the isosteresis theory generally known in the art. Compared with the control compound 1686, ES071 in which there is only one difference in the nitrogen atom of the structure (in the former structure there is a benzene ring, while in the latter there is a pyridine ring, both of which belong to common isosteres in the isosteresis theory) has achieved a significant increase in the activity. For most of the tumor cells, the inhibitory concentration of ES071 is only ½ of the former. This shows that the compounds of the present invention have achieved unexpectedly superior technical effects on the basis of the prior art.

Test Example 2

In Vivo Efficacy Test Report of ES Series Compounds in Inhibiting Human Lung Cancer H1975 Xenograft 1. Experimental Purpose The inhibitory effect of ES series compounds to subcutaneously transplanted lung cancer H1975 tumors in nude mice was evaluated.

2. Material and Method 2.1 Material 2.1.1 Test Sample

ES-071, ES-072 (slightly yellow), and ES-075, white powder, preserved at 4° C. before preparation.

2.1.2 Name of Positive Drug: CO-1686

White powder, preserved at 4° C. before preparation.

2.1.3 Negative Control (Vehicle)

22% hydroxypropyl-β-cyclodextrin, 22 g of hydroxypropyl-β-cyclodextrin was added into 100 ml of pure water.

2.1.4 Experimental Animal

BALB/c nude mice, female, weighing 17-20 g, purchased from Beijing Weitong Lihua Experimental Animal Technology Co., Ltd. (license number: SCXK (Beijing) 2012-0001). Feeding environment: SPF grade animal room, free feeding, 12 h light/12 h dark.

2.1.5 Cell Line

Human lung cancer H1975 cell culture was RPMI 1640 plus 10% FBS, and 1% sodium pyruvate, which was purchased from GIBCO, and serum was from Biosun.

Experimental Method

1. Dosing Regimen: as Shown in Table 1 Below:

TABLE 1

Animal groupings and dosing regimens

| Groups | Number of animals | Dosing concentration (mg/kg) | Dosing volume (ml/10 g) | Route of administration | Dosing frequency |
|---|---|---|---|---|---|
| Negative control group | 6 | — | 0.1 | ig | qd × 14 d |
| CO-1686 group | 6 | 30.0 | 0.1 | ig | qd × 14 d |
| ES-071 group | 6 | 30.0 | 0.1 | ig | qd × 14 d |
| ES-072 group | 6 | 30.0 | 0.1 | ig | qd × 14 d |
| ES-075 Group | 6 | 30.0 | 0.1 | ig | qd × 14 d |

2. Drug Formulation: as Shown in Table 2 Below:

TABLE 2

Drug preparation table

| Groups | dose (mg/kg) | Dosage volume (mL) | Dosage (mg) | Solvent | Solvent volume (mL) |
|---|---|---|---|---|---|
| CO-1686 group | 30.0 | 10.0 | 30.0 | 22% hydroxypropyl-β-cyclodextrin | 10.0 |
| ES-071 group | 30.0 | 10.0 | 30.0 | | 10.0 |
| ES-072 group | 30.0 | 10.0 | 30.0 | | 10.0 |
| ES-075 Group | 30.0 | 10.0 | 30.0 | | 10.0 |

After the drug was dispensed, all were suspensions which precipitated after being placed.

3. Experimental Procedure

Under aseptic conditions, H1975 cells in the proliferation stage were taken, whose cell concentration was adjusted after digestion, and seeded at armpit of nude mice with a volume of 0.1 mL. Tumor diameter was measured with vernier caliper, and after the tumor was grown to about 400 mm$^3$, 30 tumor-bearing mice were selected, which were randomly divided into 5 groups according to the size of the tumors. Each group was dosed according to the set dosing regimen, and the administering day was recorded as D1. The negative control group was given the same amount of vehicle. The longer and shorter diameters of tumor were measured twice a week; meanwhile the body weights of mice were weighed.

Efficacy Evaluation Indicators:

The relevant indicators were observed, measured and recorded on the first day of dosing. During the experiment, the tumor size was measured with a vernier caliper to observe the volume change and growth rate of the tumor mass. Tumor-bearing mice were sacrificed at the end of the experiment and the tumor mass was dissected and weighed.

Efficacy evaluation indicators include: relative tumor proliferation rate and weight, general status and other related toxicity indicators. At the end of the experiment, the tumor growth curve and weight change curve were drawn for each group.

The calculation formula of tumor volume (TV) is: TV=1/2×a×b$^2$, in which a and b respectively represent the longer and shorter diameters of the tumor. The relative tumor volume (RTV) was calculated based on the measured results and the formula was: RTV=$V_t$/$V_0$, in which $V_0$ is the tumor volume measured before dosing, and $V_t$ is the tumor volume at each measurement after dosing.

The evaluation index of anti-tumor activity is relative tumor proliferation rate T/C (%), and the formula is as follows: T/C (%)=($T_{RTV}$/$C_{RTV}$)×100%, $T_{RTV}$: treatment group's RTV; $C_{RTV}$: negative control group's RTV. T/C (%)≤40% and statistical treatment P<0.05 mean effective. The tumor weight (TW) is lower than that of the negative control group and statistical treatment P<0.05 mean effective. Inhibition rate of tumor IR (%)=(1−$T_{TW}$/$C_{TW}$)×100%, $T_{TW}$: treatment group's TW; $C_{TW}$: negative control group's TW.

Statistical Methods:

The data was expressed as Mean±SD, and t-tests were used for comparison between groups.

4. Test Results 4.1 Effect of Drugs on Animal Weight

From the trend analysis of body weight in each treatment group, there was no significant difference in body weight between the compound of the present invention group and the positive drug CO-1686 group and the negative control group (FIG. 1), which indicated that the compound of the present invention had good safety. After 14 days of intragastric administration, the animals were euthanized and an autopsy was performed. No gross abnormalities were observed in all organs.

4.2 Effect of Drugs on Size of Tumor Beared in Animals

Figure 2:
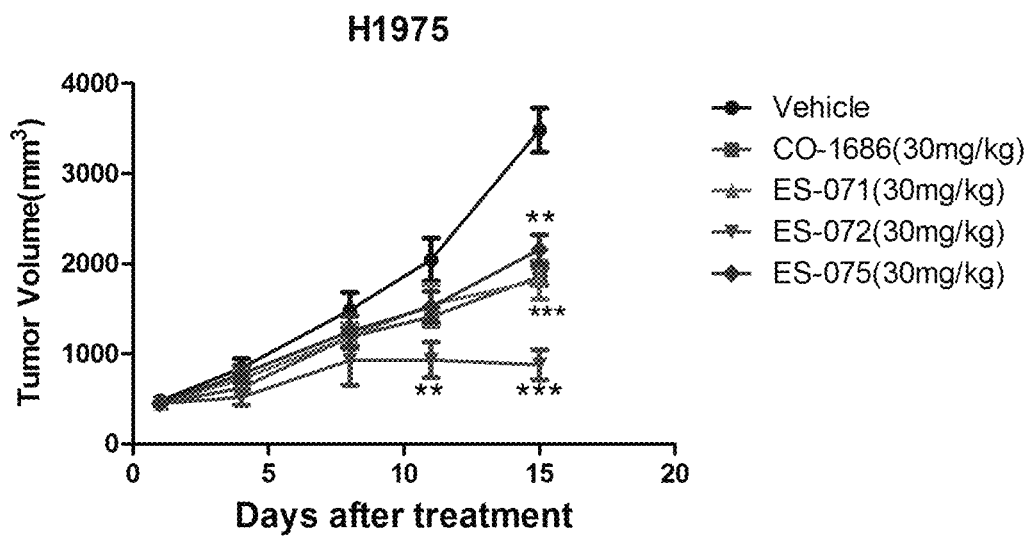
FIG. 2 shows the effect of the drug in Test Example 2 on the tumor volume of tumor-bearing nude mice.
Figure 3:
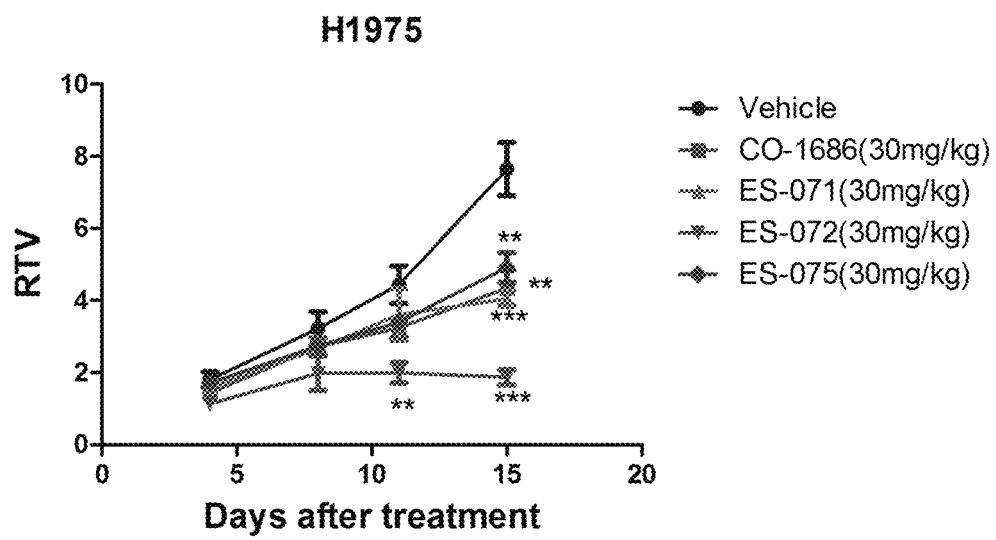
FIG. 3 shows the effect of the drug in Test Example 2 on the relative tumor volume of tumor-bearing nude mice.
Figure 4:
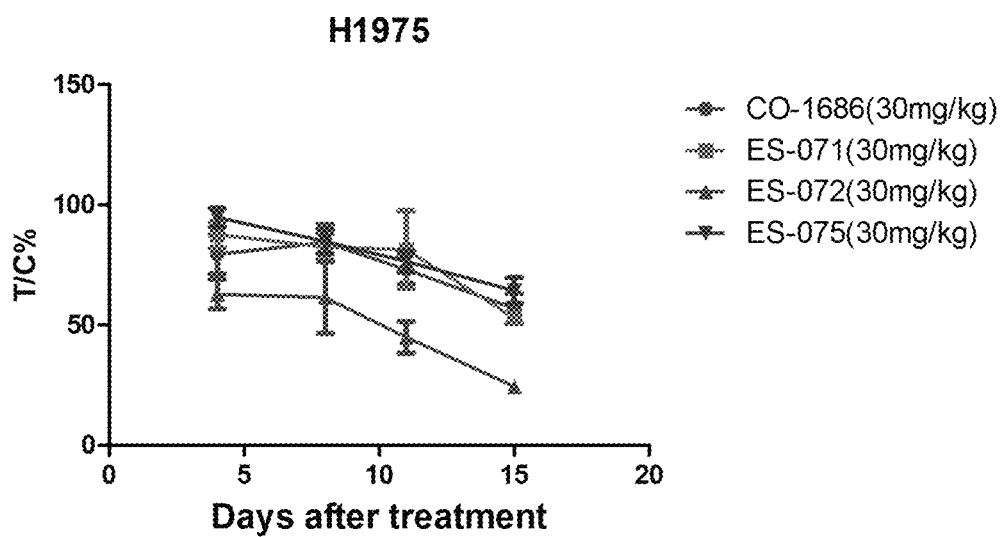
FIG. 4 shows the effect of the drug in Test Example 2 on the relative tumor proliferation rate of tumor-bearing nude mice.

After continuous intragastric administration for 14 days, the volumes of subcutaneous tumors in the ES series compound group animals and positive drug group animals were smaller than that in the negative control group animals, and there was a significant difference compared with the negative control group (see FIG. 2, FIG. 3, and FIG. 4), which indicated that the drug were effective, and the anti-tumor effect of ES-072 was better than that of the positive control group CO-1686.

Figure 5:
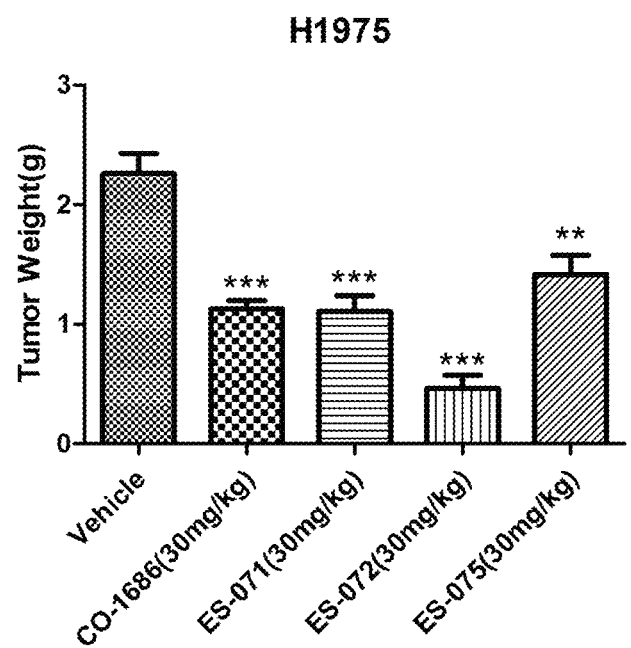
FIG. 5 shows the effect of the drug in Test Example 2 on the tumor weight of tumor-bearing nude mice.
Figure 6:
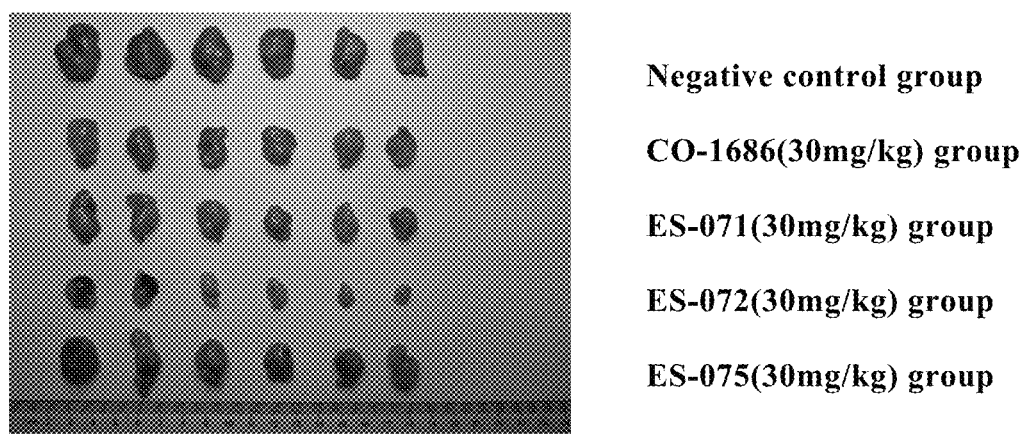
FIG. 6 shows a photograph of the tumor in Test Example 2.

At the end of the experiment, i.e. on day 14 of dosing, animals were euthanized, subcutaneous tumors were dissected and weighed. The tumors of the ES series compound group and positive drug group were significantly smaller than those of the negative control group. The tumor weight was shown in FIG. 5, and the tumor photographs were shown in FIG. 6. The inhibition rate of CO-1686 was 50.09%, and the inhibition rates of ES-071, ES-072 and ES-075 were 50.93%, 79.42%, and 37.27%, respectively. Among them, the ES-072 compound (inhibiting tumor activity in vitro is slightly lower than ES-071) unexpectedly showed significantly better anti-tumor activity than the control compound in in vivo tumor inhibition experiments, which indicated that this compound had better bioavailability than the control compound after being taken, thus being a promising compound.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound of the following formula (I):

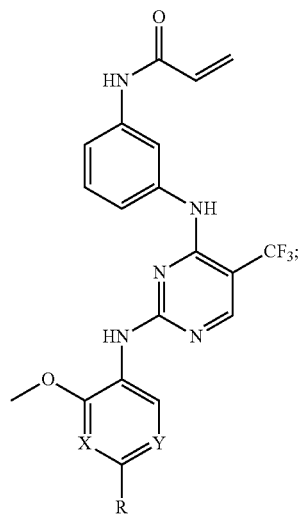

wherein:

X, Y are each independently selected from the group consisting of N, CH; with the proviso that X and Y are not CH at the same time;

R is selected from the group consisting of: unsubstituted 5-7 membered heterocycles, 5-7 membered heterocycles substituted by 1-5 substituents, C1-C6 alkyl-(unsubstituted 5-7 membered heterocycles), C1-C6 alkyl-(5-7 membered heterocycles substituted by 1-5 substituents), —NH-(unsubstituted 5-7 membered heterocycles), —NH-(5-7 membered heterocycles substituted by 1-5 substituents), —N(CH$_3$)-(unsubstituted 5-7 membered heterocycles), —N(CH$_3$)-(5-7 membered heterocycles substituted by 1-5 substituents), wherein the heterocycle contains at least one heteroatom selected from the group consisting of N, O and S;

the substitution means one or more hydrogen atoms on the group are replaced by $R_1$ substituents;

wherein the $R_1$ is selected from the group consisting of: unsubstituted or halogenated C1-C6 alkyl, C3-C8 cycloalkyl, unsubstituted or halogenated C1-C6 alkoxy, C3-C8 cycloalkyloxy, —C(O)—$R_2$, C2-C8 alkylacyl, C2-C8 alkoxyacyl, —S(O)$_2$—$R_2$, —SO$R_2$;

the $R_2$ is selected from the group consisting of unsubstituted or halogenated C1-C6 alkyl, unsubstituted or halogenated C1-C6 alkoxy, C3-C8 cycloalkyl, C3-C8cycloalkoxy, —CH$_2$—OAc, —NH$_2$, —NH(C1-C6 alkyl), —N(C1-C6 alkyl)$_2$.

2. The compound of claim 1, wherein X is N, and Y is CH.

3. The compound of claim 1, wherein the R is selected from the group; consisting of

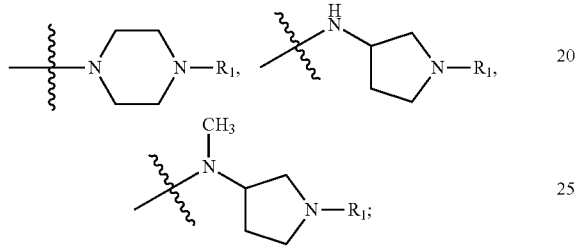

wherein the $R_1$ is selected from the group consisting of: unsubstituted or halogenated C1-C6 alkyl, C3-C8 cycloalkyl, unsubstituted or halogenated C1-C6 alkoxy, C3-C8 cycloalkyloxy, —C(O)—$R_2$, —Boc, —S(O)$_2$—$R_2$, —CH$_2$—OAc;

the $R_2$ is selected from the group consisting of unsubstituted or halogenated C1-C6 alkyl, unsubstituted or halogenated C1-C6 alkoxy, C3-C8 cycloalkyl, C3-C8 cycloalkoxy, —CH$_2$—OAc, —NH$_2$, —NH (C1-C6 alkyl), —N(C1-C6 alkyl)$_2$.

4. The compound of claim herein the compound of formula (I) is selected from the following group:

ES-069

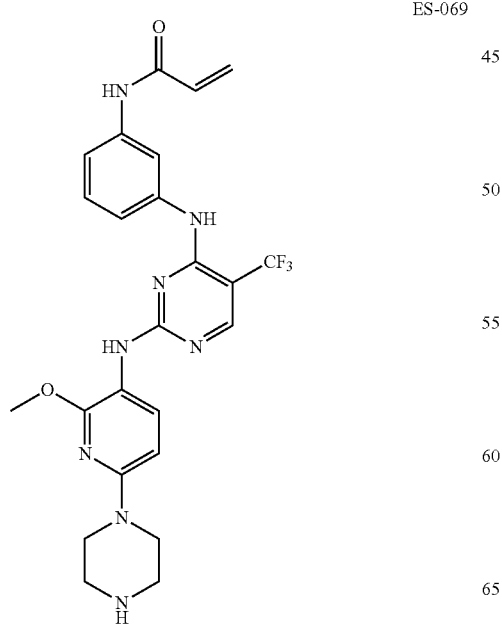

ES-070

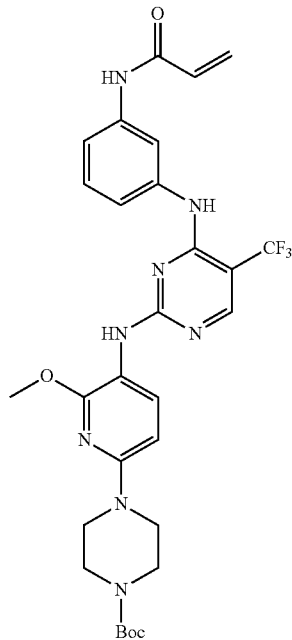

ES-071

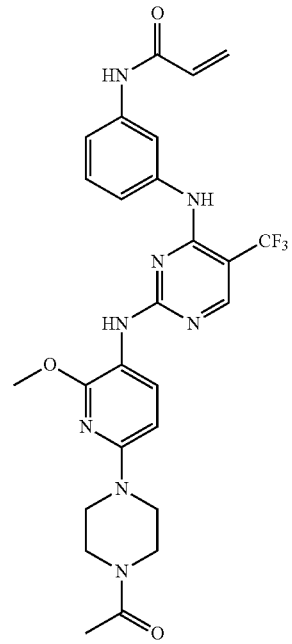

ES-072
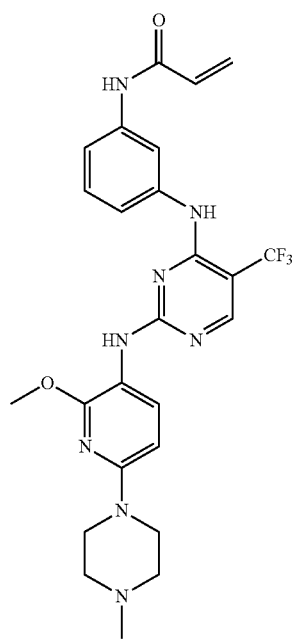
ES-073
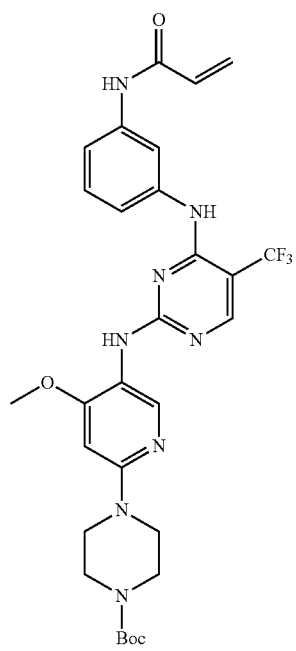
ES-074
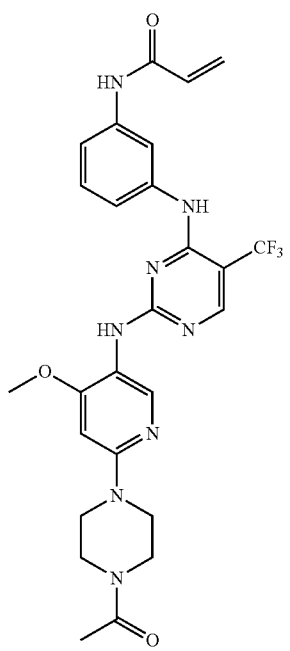
ES-075
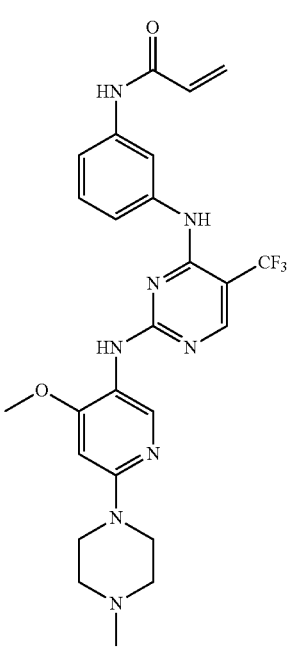

ES-0123
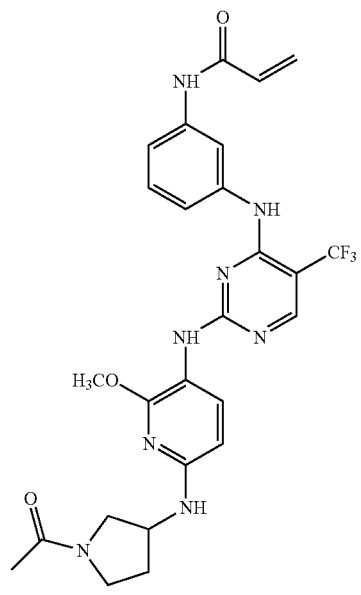
ES-0125
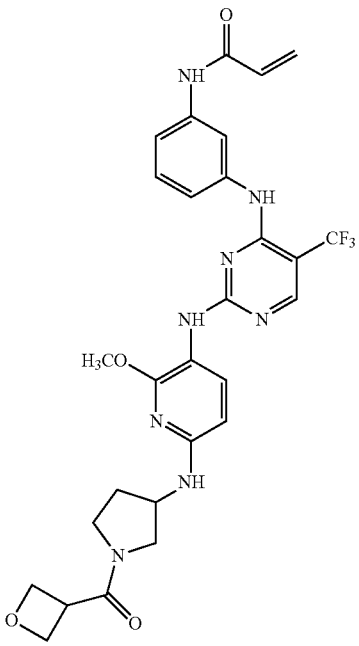
ES-0124
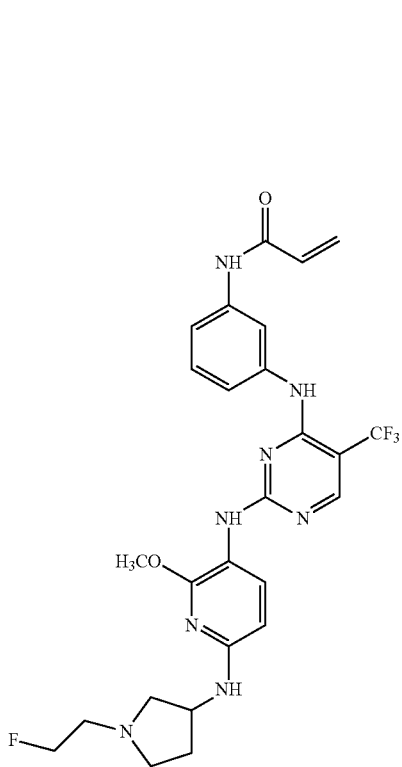
ES-0130
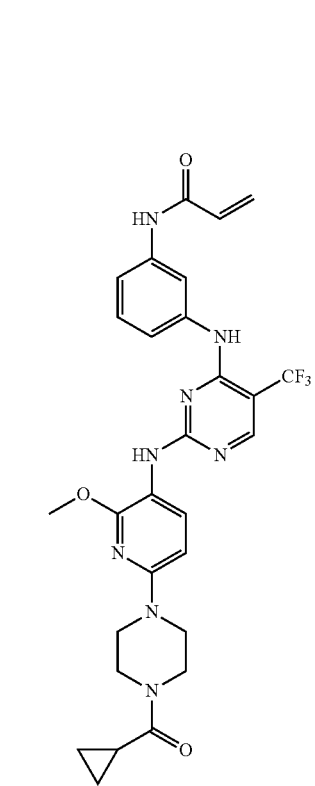

-continued
ES-0131
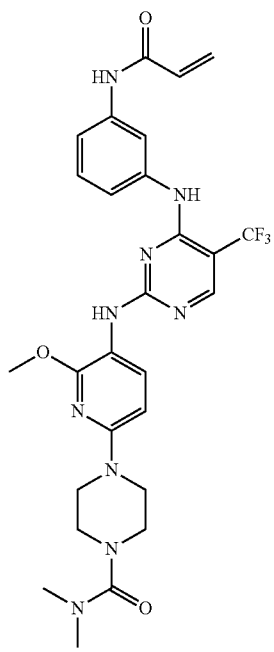
ES-0132
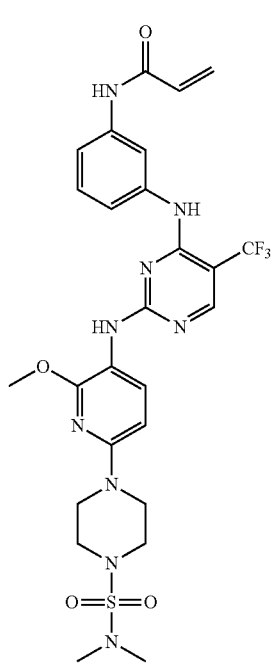
-continued
ES-0133
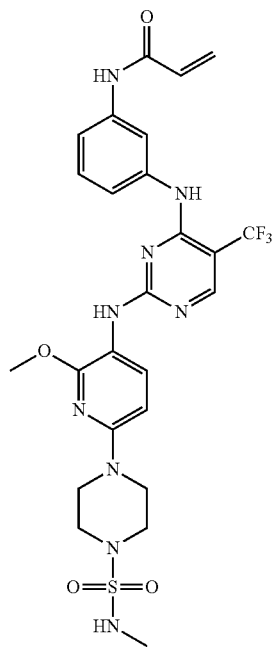
ES-0134
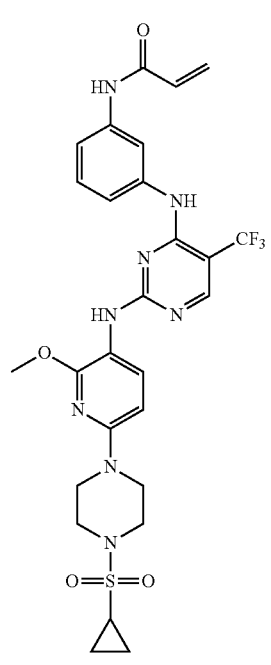

ES-0135
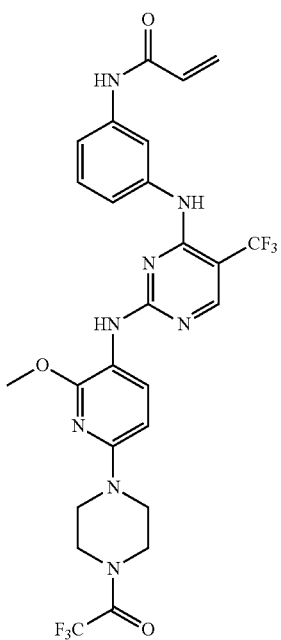
ES-0136
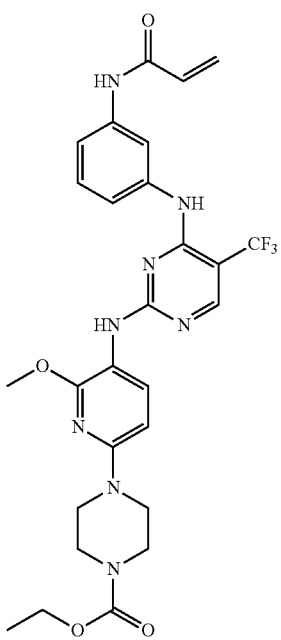
ES-0137
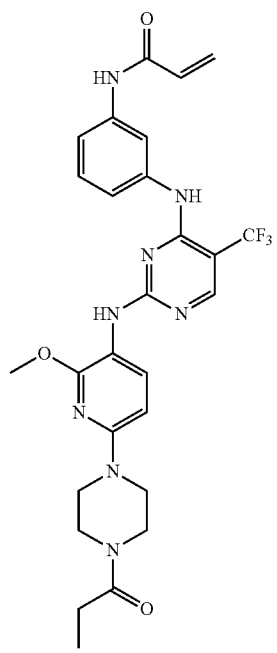
ES-0138
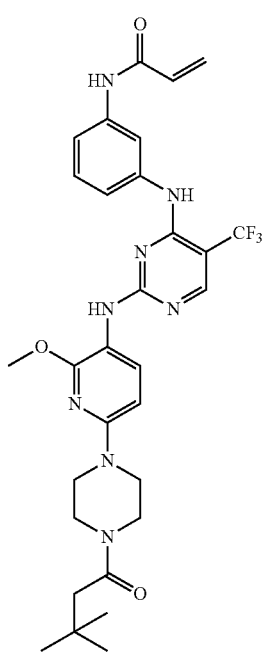

ES-0139
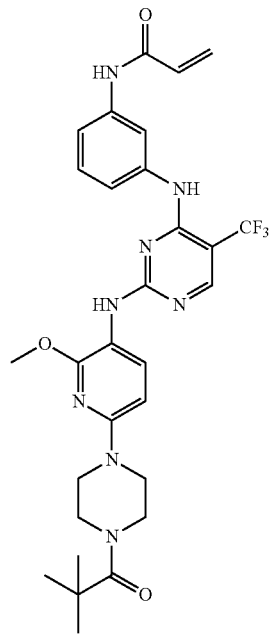
ES-0141
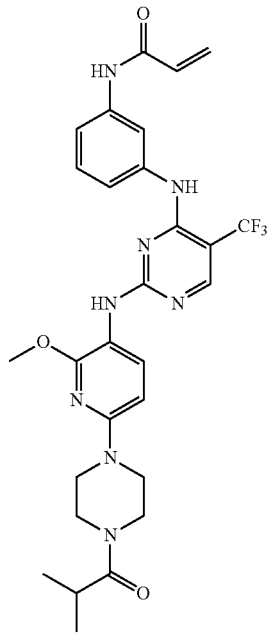
ES-0140
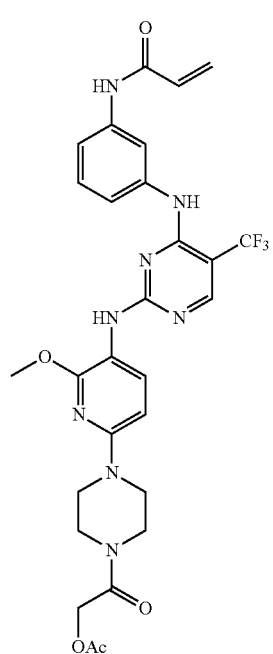
ES-0142
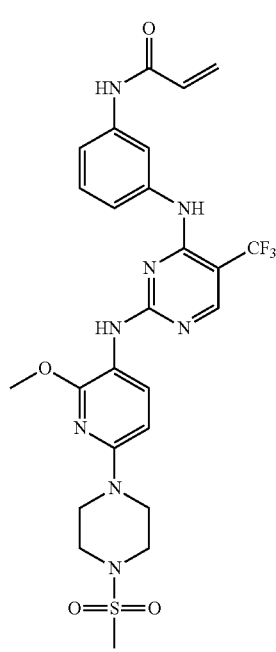

ES-0143
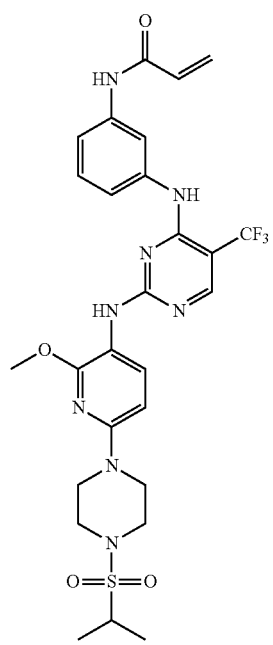
ES-145
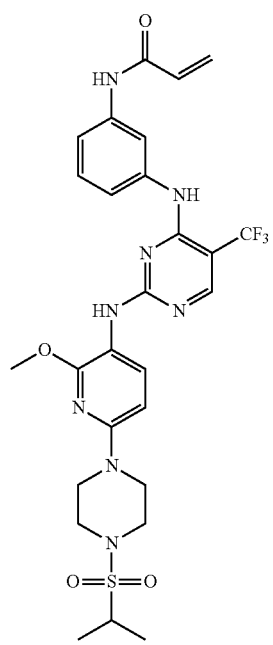
ES-0144
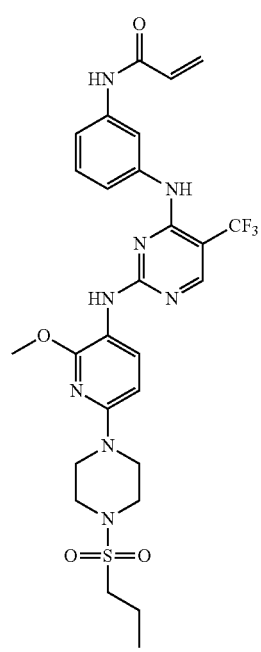
ES-146
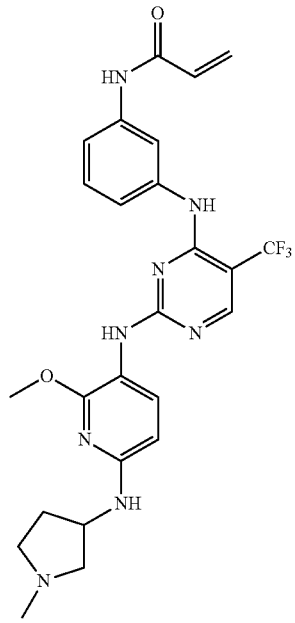

ES-147
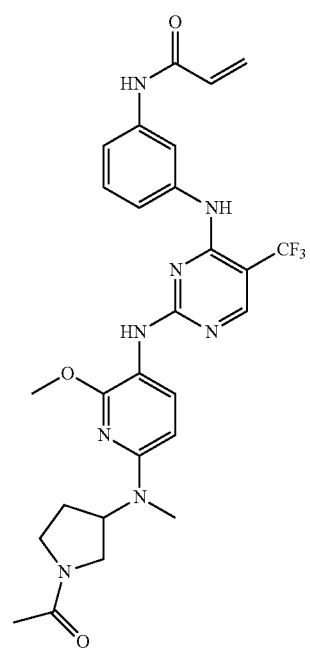
ES-148
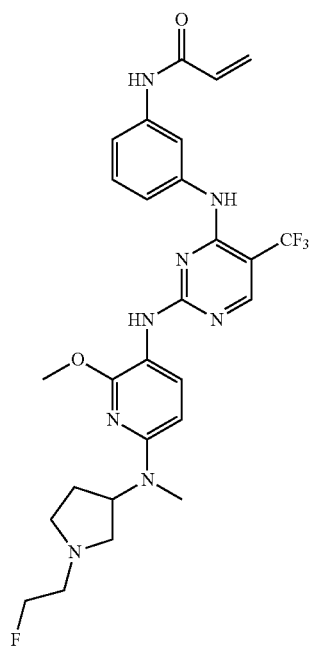
ES-149
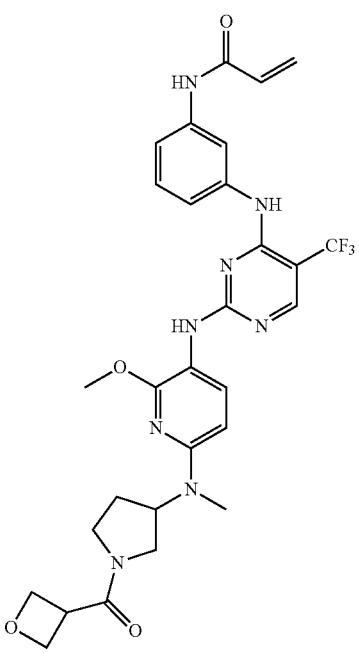
ES-150
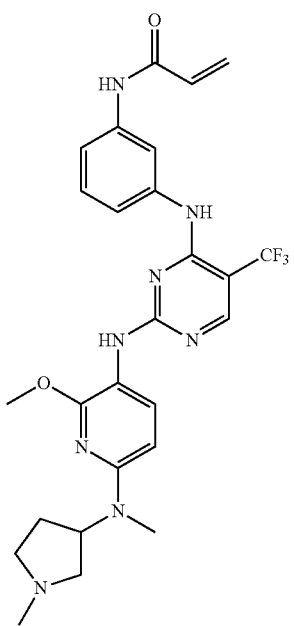

ES-151
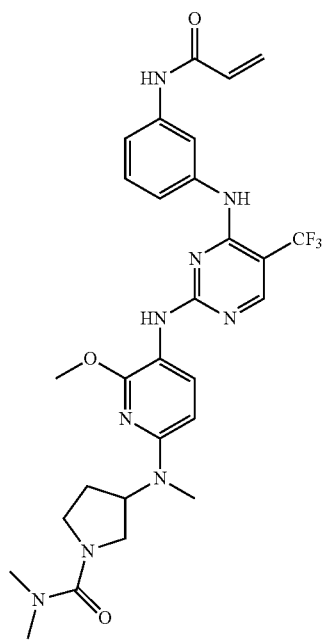
ES-158
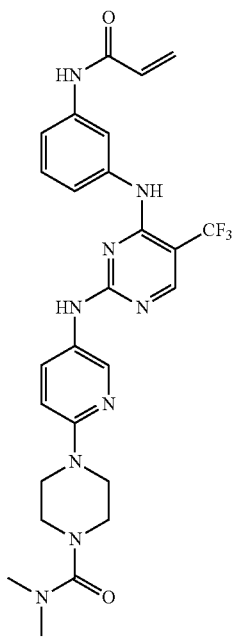
ES-157
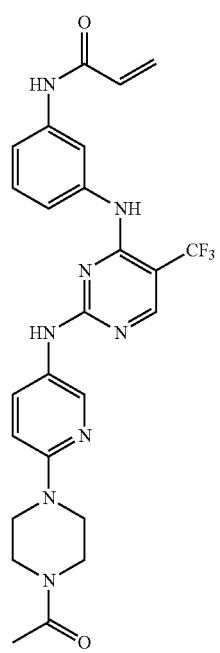
ES-159
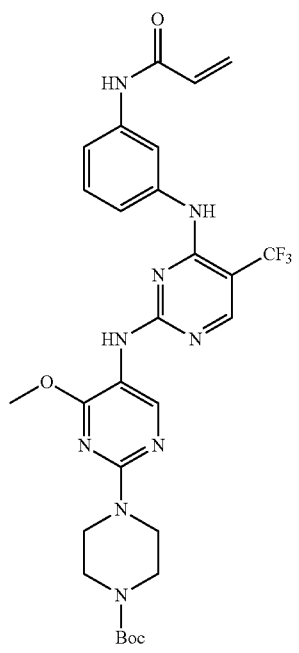

ES-160
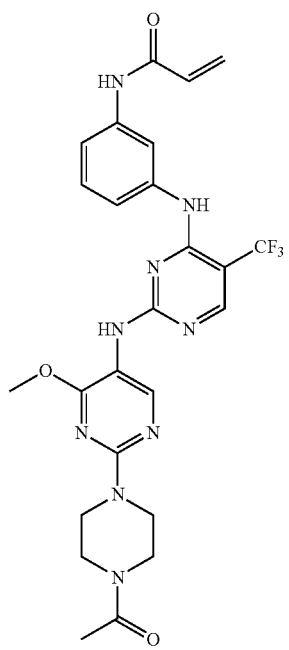
ES-163
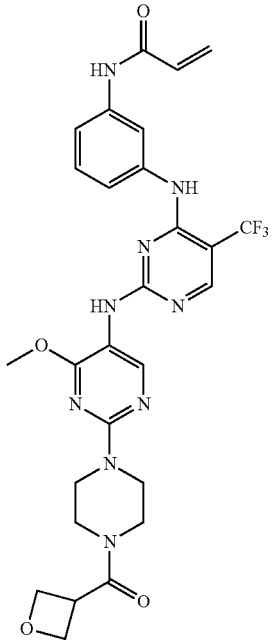
ES-161
ES-164
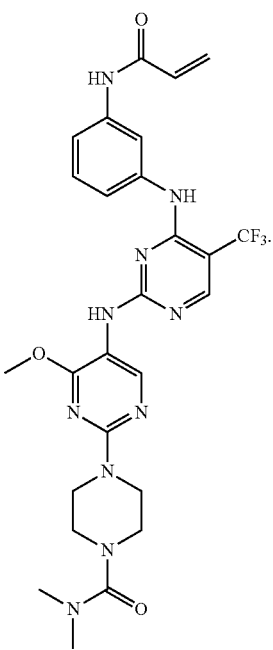
5. The compound of claim 1, wherein the compound of formula (I) is selected from the following group:

ES-071
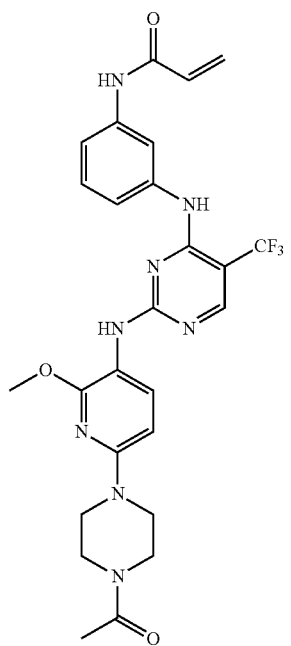
ES-075
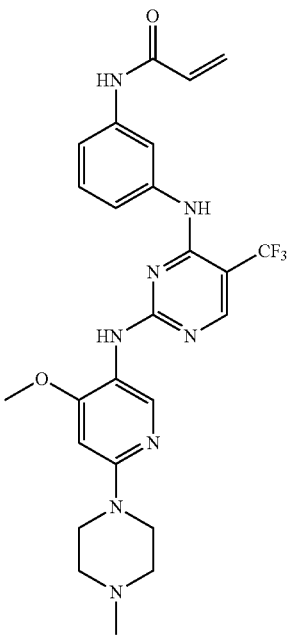
ES-072
ES-0124
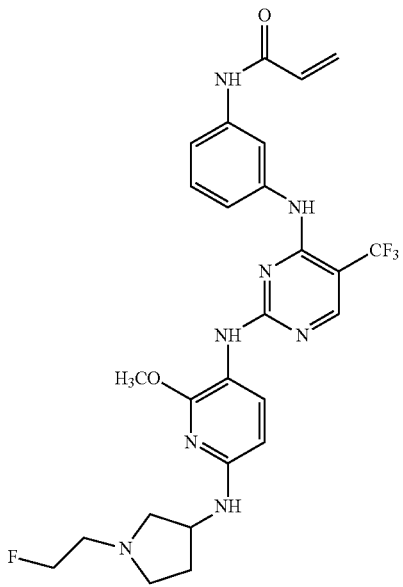

ES-0130
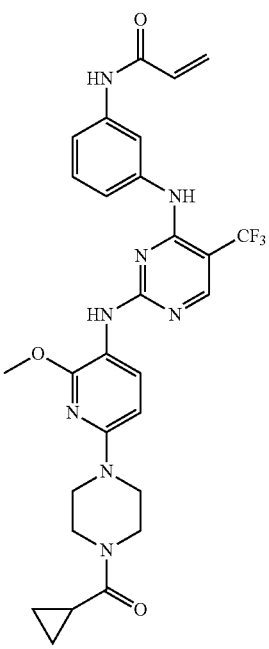
ES-146
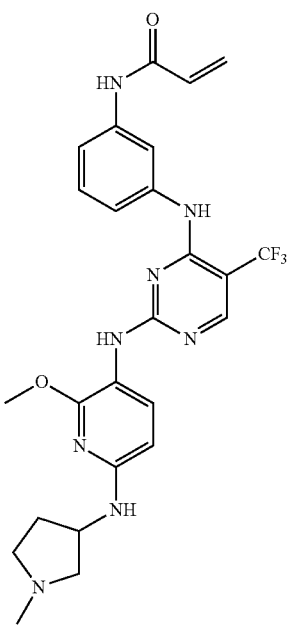
ES-0137
ES-148
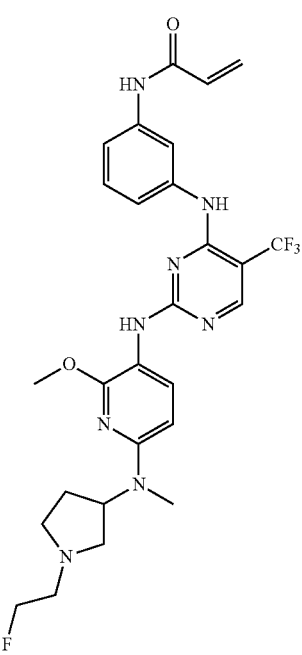

ES-150
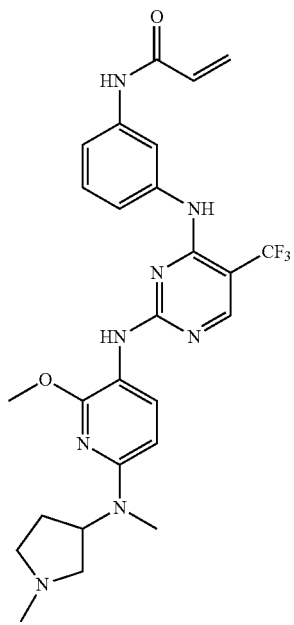
ES-160
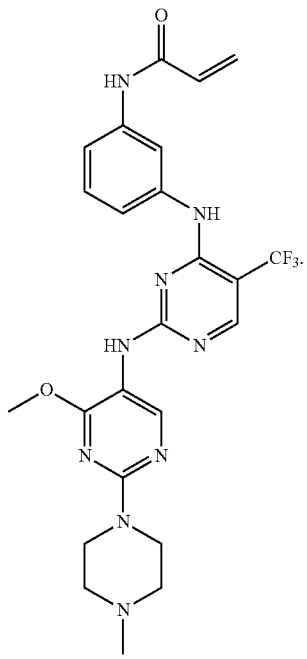
ES-161
6. A preparation method of the compound of claim 1, wherein comprising the following step:
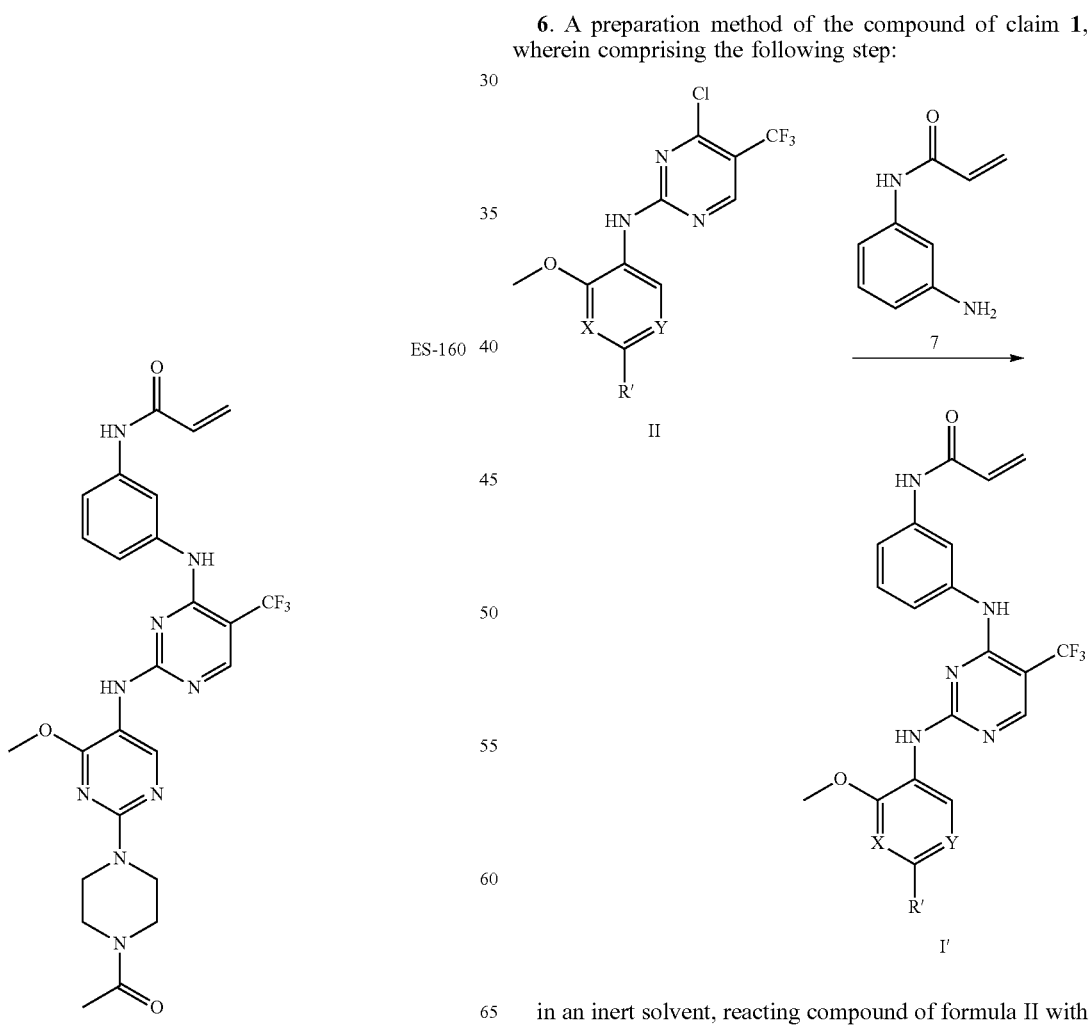
in an inert solvent, reacting compound of formula II with compound of formula 7, thus obtaining compound of formula I':

wherein R' is selected from the group consisting of:
unsubstituted 5-7 membered heterocycles,
5-7 membered heterocycles substituted by 1-5 substituents,
C1-C6 alkyl-(unsubstituted 5-7 membered heterocycles),
C1-C6 alkyl-(5-7 membered heterocycles substituted by 1-5 substituents),
—NH-(unsubstituted 5-7 membered heterocycles),
—NH-(5-7 membered heterocycles substituted by 1-5 substituents),
—N(CH$_3$)-(unsubstituted 5-7 membered heterocycles), and
—N(CH$_3$)-(5-7 membered heterocycles substituted by 1-5 substituents),
wherein the heterocycle contains at least one heteroatom selected from the group consisting of N, O and S; the substitution means one or more hydrogen atoms on the group are replaced by R$_1$ substituents;
while the remaining groups are defined as in claim 1.

7. The preparation method of claim 6, wherein comprising the following step:

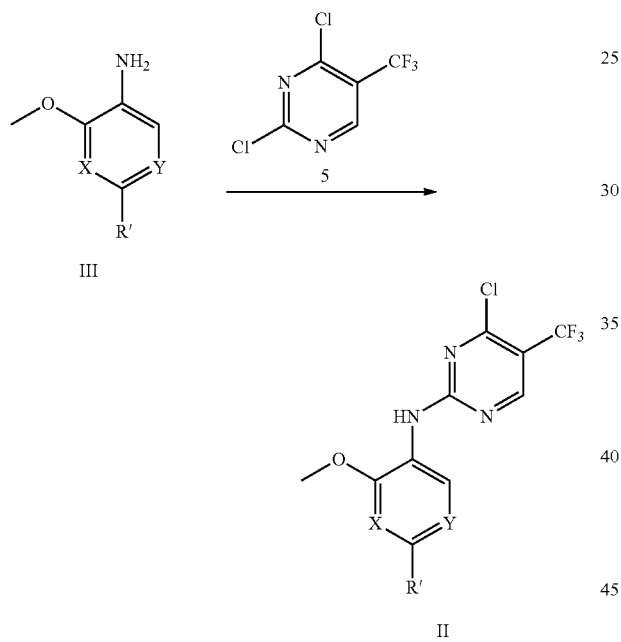

in an inert solvent, reacting compound of formula III with compound of formula 5, thus obtaining compound of formula II;

wherein, R' is as defined in claim 6, and
wherein:
X, Y are each independently selected from the group consisting of N, CH; with the provision that X and Y are not CH at the same time.

8. A pharmaceutical composition, wherein the pharmaceutical composition comprises: a therapeutically effective amount of one or more of the compound of formula (I) of claim 1, or pharmaceutically acceptable salts, tautomers, optical isomers, or pharmaceutically acceptable solvates, and optionally pharmaceutically acceptable carriers, excipients, adjuvants, accessories and/or diluents.

9. A compound of formula II:

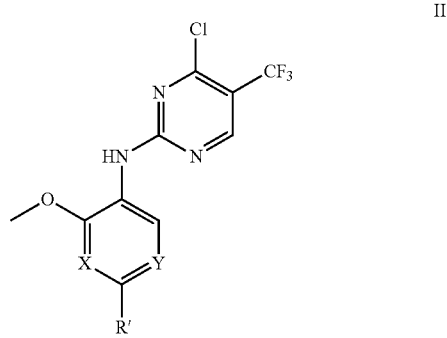

wherein R' is selected from the group consisting of:
unsubstituted 5-7 membered heterocycles,
5-7 membered heterocycles substituted by 1-5 substituents,
C1-C6 alkyl-(unsubstituted 5-7 membered heterocycles),
C1-C6 alkyl-(5-7 membered heterocycles substituted by 1-5 substituents),
—NH-(unsubstituted 5-7 membered heterocycles),
—NH-(5-7 membered heterocycles substituted by 1-5 substituents),
—N(CH$_3$)-(unsubstituted 5-7 membered heterocycles), and
—N(CH$_3$)-(5-7 membered heterocycles substituted by 1-5 substituents),
wherein the heterocycle contains at least one heteroatom selected from the group consisting of N, O and S; the substitution means one or more hydrogen atoms on the group are replaced by R$_1$ substituents, and
wherein X, Y are each independently selected from the group consisting of N, CH; with the provision that X and Y are not CH at the same time.

* * * * *

UNITED STATES PATENT AND TRADEMARK OFFICE
CERTIFICATE OF CORRECTION

PATENT NO. : 10,710,979 B2
APPLICATION NO. : 15/763156
DATED : July 14, 2020
INVENTOR(S) : Dawei Ma et al.

Page 1 of 1

It is certified that error appears in the above-identified patent and that said Letters Patent is hereby corrected as shown below:

In the Claims

Column 97, Lines 39-40, the text "The compound of claim herein the compound of formula (I) is selected from the following group: …" should be corrected to "The compound of claim 1, wherein the compound of formula (I) is selected from the following group: …"

Signed and Sealed this
Twenty-fourth Day of November, 2020

Andrei Iancu
*Director of the United States Patent and Trademark Office*